United States Patent
Ferber et al.

(10) Patent No.: US 9,943,267 B2
(45) Date of Patent: Apr. 17, 2018

(54) SYSTEMS AND METHODS FOR NON-INVASIVE RESPIRATORY RATE MEASUREMENT

(71) Applicant: Spry Health, Inc., Palo Alto, CA (US)

(72) Inventors: Elad Ferber, Woodside, CA (US); Pierre-Jean Cobut, Menlo Park, CA (US); Ramkrishnan Narayanan, San Jose, CA (US); Derya Gol Gungor, Sunnyvale, CA (US)

(73) Assignee: Spry Health, Inc., Palo Alto, CA (US)

( * ) Notice: Subject to any disclaimer, the term of this patent is extended or adjusted under 35 U.S.C. 154(b) by 0 days.

(21) Appl. No.: 15/368,477

(22) Filed: Dec. 2, 2016

(65) Prior Publication Data

US 2017/0156593 A1 Jun. 8, 2017

Related U.S. Application Data

(60) Provisional application No. 62/262,342, filed on Dec. 2, 2015, provisional application No. 62/262,532, filed
(Continued)

(51) Int. Cl.
*A61B 5/08* (2006.01)
*A61B 5/00* (2006.01)
(Continued)

(52) U.S. Cl.
CPC .......... *A61B 5/7221* (2013.01); *A61B 5/0002* (2013.01); *A61B 5/0008* (2013.01);
(Continued)

(58) Field of Classification Search
CPC .... A61B 5/1455; A61B 5/6802; A61B 5/0816
See application file for complete search history.

(56) References Cited

U.S. PATENT DOCUMENTS

| 5,309,916 A | 5/1994 | Hatschek |
|---|---|---|
| 2003/0036685 A1 | 2/2003 | Goodman |

(Continued)

FOREIGN PATENT DOCUMENTS

| WO | 2015107268 | 7/2015 |
|---|---|---|
| WO | 2015116891 | 8/2015 |

OTHER PUBLICATIONS

International Application No. PCT/US2016/064838, International Search Report and Written Opinion dated Mar. 29, 2017.
(Continued)

*Primary Examiner* — Christian Jang
(74) *Attorney, Agent, or Firm* — Sheppard, Mullin, Richter & Hampton LLP

(57) ABSTRACT

Systems and methods for non-invasive respiratory rate measurement are disclosed. In some embodiments, a system comprises a wearable member including an energy transmitter configured to project energy into tissue of a user. An energy receiver generates a multichannel signal based on a first received portion of the energy, the received portion of energy being received through the tissue of the user. A respiratory rate calculation system includes a pre-processing module for filter noise from the signal. A spectrum module determines a spectrum of the signal. A respiratory rate processing module determines a first respiratory rate from the spectrum of the signal. A noise reference and one or more second respiratory rates are obtained. A third respiratory rate is determined based on the first respiratory rate, the noise reference, and the one or more second respiratory rates. A communication module provides a message based on the third respiratory rate.

19 Claims, 23 Drawing Sheets

Related U.S. Application Data on Dec. 3, 2015, provisional application No. 62/262,540, filed on Dec. 3, 2015.

(51) Int. Cl.

| *A61B 5/1455* | (2006.01) |
| *A61B 5/021* | (2006.01) |
| *A61B 5/145* | (2006.01) |
| *A61B 5/024* | (2006.01) |
| *A61B 5/117* | (2016.01) |

(52) U.S. Cl.
CPC .......... *A61B 5/0022* (2013.01); *A61B 5/0064* (2013.01); *A61B 5/021* (2013.01); *A61B 5/024* (2013.01); *A61B 5/02141* (2013.01); *A61B 5/02416* (2013.01); *A61B 5/0806* (2013.01); *A61B 5/117* (2013.01); *A61B 5/1455* (2013.01); *A61B 5/14532* (2013.01); *A61B 5/14535* (2013.01); *A61B 5/14539* (2013.01); *A61B 5/14546* (2013.01); *A61B 5/14551* (2013.01); *A61B 5/4872* (2013.01); *A61B 5/6802* (2013.01); *A61B 5/6816* (2013.01); *A61B 5/6823* (2013.01); *A61B 5/6824* (2013.01); *A61B 5/6829* (2013.01); *A61B 5/721* (2013.01); *A61B 5/7264* (2013.01); *A61B 5/7275* (2013.01); *A61B 5/7435* (2013.01)

(56) References Cited

U.S. PATENT DOCUMENTS

| 2004/0138540 A1 | 7/2004 | Baker, Jr. et al. |
| 2006/0122476 A1 | 6/2006 | Van Slyke |
| 2006/0211942 A1 | 9/2006 | Hoctor et al. |
| 2008/0039731 A1 | 2/2008 | McCombie et al. |
| 2009/0326349 A1 | 12/2009 | McGonigle et al. |
| 2011/0257489 A1 | 10/2011 | Banet et al. |
| 2013/0079657 A1 | 3/2013 | Ochs et al. |
| 2013/0197322 A1 | 8/2013 | Tran |
| 2014/0031652 A1 | 1/2014 | Baker, Jr. et al. |
| 2014/0243633 A1 | 8/2014 | Addison et al. |
| 2014/0316226 A1 | 10/2014 | Ferber et al. |
| 2015/0351699 A1 | 12/2015 | Addison et al. |
| 2016/0242700 A1 | 8/2016 | Ferber et al. |
| 2016/0287110 A1 | 10/2016 | Morris et al. |

OTHER PUBLICATIONS

International Application No. PCT/US2016/064843, International Search Report and Written Opinion dated Apr. 3, 2017.
International Application No. PCT/US2016/064848, International Search Report and Written Opinion dated Mar. 27, 2017.

[2   0.5640  0.2540  0.5825  0.1999  0.4672  0.1777  0.4278  0.1599  0.3389  0.1439  0.2682  0.1286
0.2286  0.1135  0.1836  0.0975  0.1226  0.0794  0.8057  0.5109  0.3123  1.7755  -0.0038 0.7883  0.3677
2.4038  -0.0820 -0.1100 -0.8483 0.0966  -0.2134 -0.3745 0.2508 ]

SYSTEMS AND METHODS FOR NON-INVASIVE RESPIRATORY RATE MEASUREMENT

CROSS-REFERENCE TO RELATED APPLICATIONS

The present application claims the benefit of U.S. Provisional Patent Application Ser. No. 62/262,540, filed Dec. 3, 2015, entitled "Prediction of Blood Pressure from PPG Data," U.S. Provisional Patent Application Ser. No. 62/262,532, filed Dec. 3, 2015, entitled "Validity and Classification for Biological Signal Recognition," and U.S. Provisional Patent Application Ser. No. 62/262,342, filed Dec. 2, 2015, entitled "Respiratory Rate Estimation Using Multispectral Data," which are incorporated herein by reference.

BACKGROUND

Technical Field

Embodiments of the present inventions relate generally to blood metrics measurement. More specifically, embodiments of the present inventions relate to non-invasive respiratory rate measurement.

Description of Related Art

Wearable activity monitoring devices are growing in popularity. These devices aim to facilitate achieving a user's goal such as to lose weight, to increase physical activity, or simply to improve overall health. Many such devices may interface with computer software to allow visualization of the recorded data. Nevertheless, most devices are evolved cousins of pedometers, which measure the number of steps a user takes. Even though additional functions such as tallying the distance a user travels or calculating calorie consumptions may be added, these devices lack the ability to measure blood metrics.

Respiratory rate may be measured along with other vital signs, such as heart rate, blood pressure and body temperature. Respiratory rate may be an indicator of the performance of the various systems of the body, and may be a predictor of adverse events, such as cardiac arrest or sleep apnea. However, the level of recordation of vital signs, especially respiration rate, in many environments (e.g., hospitals) may be poor or even non-existent.

SUMMARY

An exemplary system comprises an energy transmitter, an energy receiver, and an analyzer. The energy transmitter may project energy at a first wavelength and a second wavelength into tissue of a user, the first wavelength and the second wavelength being associated with at least one nutrient of a set of nutrients in blood of the user. The energy receiver may generate a composite signal based on a fraction of the energy at the first wavelength and the second wavelength, the fraction of the energy being received through the tissue of the user. The analyzer may separate the composite signal into a first signal corresponding to the first wavelength and a second signal corresponding to the second wavelength, and detect, in the blood of the user, a concentration of the at least one nutrient of the set of nutrients based on the first signal and the second signal.

The fraction of the energy may be received by the energy receiver after the fraction of the energy is reflected by the tissue of the user. The system may comprise a wearable member. The energy transmitter and the energy receiver may be secured to the wearable member such that the energy transmitter and the energy receiver are in contact or in proximity with the tissue. The analyzer may be further configured to determine a set of blood metrics based on the first signal and the second signal, the concentration of at least one nutrient of the set of nutrients being determined based on the determined set of blood metrics. The system may further comprise a user interface configured to display at least some of the set of blood metrics. The analyzer may be further configured to compare a blood metric of the set of blood metric to a threshold and to generate an alert if the blood metric exceeds the threshold. The set of blood metrics may comprise a blood glucose concentration.

The analyzer may be further configured to determine a first AC component and a first DC component of the first signal, to determine a second AC component and a second DC component of the second signal, wherein the concentration of a nutrient of the set of nutrients is detected based on the first AC component, the first DC component, the second AC component, and the second DC component. The system may further comprise a motion detector configured to measure a level of motion, and the analyzer is configured to compare the level of motion to a threshold and to discount a measurement of the composite signal when the level of motion exceeds the threshold. A nutrient of the set of nutrients may comprise glucose.

An exemplary method may comprise projecting energy at a first wavelength and a second wavelength into tissue of a user, the first wavelength and the second wavelength being associated with at least one nutrient of a set of nutrients in blood of the user, generating a composite signal based on a fraction of the energy at the first wavelength and the second wavelength, the fraction of the energy being received through the tissue of the user, separating the composite signal into a first signal corresponding to the first wavelength and a second signal corresponding to the second wavelength, and detecting, in the blood of the user, a concentration of the at least one nutrient of the set of nutrients based on the first signal and the second signal.

Another exemplary system may comprise an energy transmitter, an energy receiver, and an analyzer. The energy transmitter may be configured to project energy at a first wavelength and a second wavelength into tissue of a user, the first wavelength and the second wavelength being associated with, in blood of the user, at least one component. The at least one component being at least one of one of glucose, hemoglobin, triglycerides, cholesterol, bilirubin, protein, albumin, blood pH, Hematocrit, cortisol, and/or electrolytes. The energy receiver may be configured to generate a composite signal based on a fraction of the energy at the first wavelength and the second wavelength, the fraction of the energy being received through the tissue of the user. The analyzer may be configured to separate the composite signal into a first signal corresponding to the first wavelength and a second signal corresponding to the second wavelength, and to detect, in the blood of the user, a concentration of the at least one component based on the first signal and the second signal.

Other features and aspects of various embodiments will become apparent from the following detailed description, taken in conjunction with the accompanying drawings, which illustrate, by way of example, the features of such embodiments.

Typically, blood pressure is measured non-invasively with a sphygmomanometer. However, such devices are often uncomfortable and do not permit continuous blood pressure measurement. Some embodiments described herein include systems and methods for non-invasive continuous blood pressure measurement. For example, a blood metrics measurement apparatus may generate multichannel signals (e.g., PPG signals) which may be provided to a blood pressure calculation system to calculate arterial blood pressure values (e.g., systolic blood value pressure and/or diastolic blood pressure value). More specifically, the blood pressure calculation system (or the blood pressure measurement apparatus) may filter the multichannel signals (e.g., to remove noise from the signals), select (or, "extract") subsets of "high quality" waves from the multichannel signals, select (or, "extract") sets of features from each of the high quality waves, and generate sets of feature vectors based on the selected sets of features. In some embodiments, an empirical blood pressure model is used to calculate arterial blood pressure values based on the sets of feature vectors.

In various embodiments, a system comprises a wearable member and a blood pressure calculation system. The wearable member may include an energy transmitter configured to project energy at a first wavelength and energy at a second wavelength into tissue of a user, and an energy receiver configured to generate a first signal based on a first received portion of the energy at the first wavelength and a second signal based on a second received portion of the energy at the second wavelength, the first received portion of energy and the second received portion of energy each being received through the tissue of the user. The blood pressure calculation system may include a pre-processing module configured to filter noise (e.g., motion related noise) from the first signal and the second signal, and a wave selection module configured to identify a first subset of waves from a first set of waves of the first signal and a second subset of waves from a second set of waves of the second signal, each of the first subset of waves representing a separate approximation of an average of the first set of waves over a predetermined amount of time and each of the second subset of waves representing a separate approximation of an average of the second set of waves over the predetermined amount of time. The blood pressure calculation system may further include a feature extraction module configured to generate a first set of feature vectors and a second set of feature vectors, the first set of feature vectors generated from the first subset of waves, the second set of feature vectors generated from the second subset of waves, wherein each of the feature vectors of the first set of feature vectors and the second set of feature vectors include measurement values and metric values, the measurement values corresponding to amplitude or location points of a particular wave, the metric values generated from metric functions that use at least one of the measurement values. The blood pressure calculation system may additionally include a blood pressure processing module configured to calculate an arterial blood pressure value based on the first set of feature vectors, the second set of feature vectors, and an empirical blood pressure calculation model, the empirical blood pressure calculation model configured to receive the first set of feature vectors and the second set of feature vectors as input values. The blood pressure calculation system may further include a communication module configured to provide a message including or being based on the arterial blood pressure value.

The pre-processing module may be configured to filter noise from the first signal and second signal using an adaptive filter configured to remove motion noise from the first and second signals. The energy transmitter may include a first light source and a second light source, the first light source configured to project the energy at the first wavelength, the second light source configured to project the energy at the second wavelength.

In some embodiments, the first light source and the second light source are spaced at a predetermined distance from each other, and each of the first and second light sources are associated with a different corresponding photodiode energy receiver. The measurement values may comprise a transit time determined based on a time for blood to transit the predetermined distance between the first and second light sources. The measurement values may include any of wave peak locations or amplitudes, or wave valley locations or amplitudes.

In some embodiments, the measurement values include any of an associated wave's first or higher order derivative peak locations or amplitudes, the associated wave's first or higher order derivative valley locations or amplitudes, or first or higher order moments of the associated wave. The metric functions may include one or more particular metric functions that calculate a distance between two measurement values.

The energy projected by the first light source and the energy projected by second light source may each have the same wavelength. In related embodiments, the feature extraction module is further configured to determine a phase shift between the first signal and the second signal; calculate, based on the phase shift, any of a pulse wave velocity or a pulse transit time based on the predetermined distance; and the blood pressure calculation module is further configured to calculate the arterial blood pressure value based on first set of feature vectors, the second set of feature vectors, any of the pulse wave velocity or the pulse transit time, the empirical blood pressure calculation model, the empirical blood pressure calculation model further configured to receive the first set of feature vectors, the second set of feature vectors, and any of the pulse wave velocity or the pulse transit time as input. The first signal and the second signal each comprise a photoplethysmogram (PPG) signal An example method may comprise projecting, at an energy transmitter, energy at a first wavelength and energy at a second wavelength into tissue of a user; generating, at the energy transmitter, a first signal based on a first received portion of the energy at the first wavelength and a second signal based on a second received portion of the energy at the second wavelength, the first received portion of energy and the second received portion of energy each being received through the tissue of the user; filtering, at a blood pressure calculation system, noise from the first signal and second signal; identifying, at the blood pressure calculation system, a first subset of waves from a first set of waves of the first signal and a second subset of waves from a second set of waves of the second signal, each of the first subset of waves representing a separate approximation of an average of the first set of waves over a predetermined amount of time and each of the second subset of waves representing a separate approximation of an average of the second set of waves over the predetermined amount of time; generating, at the blood pressure calculation system, a first set of feature vectors and a second set of feature vectors, the first set of feature vectors generated from the first subset of waves, the second set of feature vectors generated from the second subset of waves, wherein each of the feature vectors of the first set of feature vectors and the second set of feature vectors include measurement values and metric values, the measurement values corresponding to amplitude or location points of a particular wave, the metric values generated from metric functions that use at least one of the measurement values; calculating, at the blood pressure calculation system, an arterial blood pressure value based on the first set of feature vectors, the second set of feature vectors, and an empirical blood pressure calculation model, the empirical blood pressure calculation model configured to receive the first set of feature vectors and the second set of feature vectors as input values; and providing, from the blood pressure calculation system, a message including or being based on the arterial blood pressure value.

In some embodiments, the filtering noise from the first signal and second signal comprises filtering noise from the first signal and second signal using an adaptive filter configured to remove motion noise from the first signal and the second signal.

The energy transmitter may include a first light source and a second light source, the first light source configured to project the energy at the first wavelength, the second light source configured to project the energy at the second wavelength. In related embodiments, the first light source and the second light source are spaced at a predetermined distance from each other, and each of the first and second light sources are associated with a different corresponding photodiode energy receiver. The measurement values may comprise a transit time determined based on a time for blood to transit the predetermined distance between the first and second light sources.

In some embodiments, the measurement values include any of wave peak locations or amplitudes, or wave valley locations or amplitudes. The measurement values may include any of an associated wave's first or higher order derivative peak locations or amplitudes, the associated wave's first or higher order derivative valley locations or amplitudes, or first or higher order moments of the associated wave. The metric functions may include one or more particular metric functions that calculate a distance between two measurement values.

In some embodiments, the energy projected by the first light source and the energy projected by second light source each have the same wavelength. The feature extraction module may be further configured to determine a phase shift between the first signal and the second signal, calculate (based on the phase shift) any of a pulse wave velocity or a pulse transit time based on the predetermined distance. The blood pressure calculation module may be further configured to calculate the arterial blood pressure value based on first set of feature vectors, the second set of feature vectors, any of the pulse wave velocity or the pulse transit time, the empirical blood pressure calculation model, the empirical blood pressure calculation model further configured to receive the first set of feature vectors, the second set of feature vectors, and/or any of the pulse wave velocity or the pulse transit time as input.

An example system comprises a communication interface, a pre-processing module, a wave selection module, a feature extraction module, a blood pressure processing module, and a communication module. The communication interface may be configured to receive a first signal and a second signal, the first signal being based on a first received portion of energy having been previously projected at a first wavelength into tissue of a user, the second signal being based on a second received portion of energy having been previously projected at a second wavelength into the tissue of the user. The pre-processing module may be configured to remove noise from the first signal and the second signal. The wave selection module may be configured to identify a first subset of waves from the first set of waves of a first signal and a second subset of waves from a second set of waves of the second signal, each of the first subset of waves representing a separate approximation of an average of the first set of waves over a predetermined amount of time and each of the second subset of waves representing a separate approximation of an average of the second set of waves over the predetermined amount of time. The feature extraction module may be configured to generate a first set of feature vectors and a second set of feature vectors, the first set of feature vectors generated from the first subset of waves, the second set of feature vectors generated from the second subset of waves, wherein each of the feature vectors of the first set of feature vectors and the second set of feature vectors include measurement values and metric values, the measurement values corresponding to amplitude or location points of a particular wave, the metric values generated from metric functions that use at least one measurement value. The blood pressure processing module may be configured to calculate an arterial blood pressure value based on the first set of feature vectors, the second set of feature vectors, and an empirical blood pressure calculation model, the empirical blood pressure calculation model configured to receive the first set of feature vectors and the second set of feature vectors as input values. The communication module may be configured to provide a message including or being based on the arterial blood pressure value.

An example system comprises a processor; and memory storing instructions that, when executed by the processor, cause the processor to: receive a first signal and a second signal, the first signal being based on a first received portion of energy having been previously projected at a first wavelength into tissue of a user, the second signal being based on a second received portion of energy having been previously projected at a second wavelength into the tissue of the user; filter noise (e.g., motion related noise) from the first signal and the second signal; identify a first subset of waves from a first set of waves of the first signal and a second subset of waves from a second set of waves of the second signal, each of the first subset of waves representing a separate approximation of an average of the first set of waves over a predetermined amount of time and each of the second subset of waves representing a separate approximation of an average of the second set of waves over the predetermined amount of time; generate a first set of feature vectors and a second set of feature vectors, the first set of feature vectors generated from the first subset of waves, the second set of feature vectors generated from the second subset of waves, wherein each of the feature vectors of the first set of feature vectors and the second set of feature vectors include measurement values and metric values, the measurement values corresponding to amplitude or location points of a particular wave, the metric values generated from metric functions that use at least one of the measurement values; calculate an arterial blood pressure value based on the first set of feature vectors, the second set of feature vectors, and an empirical blood pressure calculation model, the empirical blood pressure calculation model configured to receive the first set of feature vectors and the second set of feature vectors as input values; and provide a message including or being based on the arterial blood pressure value.

Another example system comprises a wearable member including an energy transmitter configured to project energy into tissue of a user, an energy receiver, a respiratory rate calculation system, a spectrum module, a respiratory rate processing module, and a communication module. The energy receiver may be configured to generate a multichannel signal based on a first received portion of the energy, the received portion of energy being received through the tissue of the user. The respiratory rate calculation system may include a pre-processing module configured to filter noise from the multichannel signal. The spectrum module may be configured to determine a spectrum of the multichannel signal. The respiratory rate processing module may be configured to determine a first respiratory rate from the spectrum of the multichannel signal, obtain a noise reference, obtain one or more second respiratory rates, and determine a third respiratory rate based on the first respiratory rate, the noise reference, and the one or more second respiratory rates. The communication module may be configured to provide a message including or being based on the third respiratory rate.

In some embodiments, the energy transmitter includes a first light source and a second light source, the first light source configured to project the energy at a first wavelength, and the second light source configured to project the energy at a second wavelength.

The pre-processing module may be configured to filter noise from the multichannel signal using a trained respiratory rate classifier configured to determine filter parameters for the pre-processing module. In related embodiments, the trained respiratory rate classifier comprises a respiratory rate classifier trained using ground truth data and one or feature vectors generated from the multichannel signal. The one or more features vectors may include a set of features extracted from the multichannel signal, the set of features including any of optical ratio features, heart rate, signal level and range features, and signal metric features.

In some embodiments, the spectrum module determines the spectrum of the multichannel signal based on a spectral density of the multichannel signal. The one or more second respiratory rates may comprise one or more previously obtained respiratory rates associated with the user. The energy projected by the first light source and the energy projected by second light source may each have the same wavelength. The multichannel signal may comprise a multichannel photoplethysmogram (PPG) signal.

In various embodiments, a method comprises projecting, by a wearable member, energy into tissue of a user; generating, by the wearable member, a multichannel signal based on a first received portion of the energy, the received portion of energy being received through the tissue of the user; filtering, by a respiratory calculation system, noise from the multichannel signal; determining, by the respiratory calculation system, a spectrum of the multichannel signal; determining, by the respiratory calculation system, a first respiratory rate from the spectrum of the multichannel signal; obtaining, by the respiratory calculation system, a noise reference; obtaining, by the respiratory calculation system, one or more second respiratory rates; and determining, by the respiratory calculation system, a third respiratory rate based on the first respiratory rate, the noise reference, and the one or more second respiratory rates; and providing, by the respiratory calculation system, a message including or being based on the third respiratory rate.

The energy may be projected using a first light source and a second light source, the first light source configured to project the energy at a first wavelength, and the second light source configured to project the energy at a second wavelength. The noise may be filtered from the multichannel signal using a trained respiratory rate classifier configured to determine filter parameters for the pre-processing module. In related embodiments, the trained respiratory rate classifier comprises a respiratory rate classifier trained using ground truth data and one or feature vectors generated from the multichannel signal. In related embodiments, the one or more features vectors include a set of features extracted from the multichannel signal, the set of features including any of optical ratio features, heart rate, signal level and range features, and signal metric features.

The spectrum may be determined based on a spectral density of the multichannel signal. In some embodiments, the one or more second respiratory rates comprises one or more previously obtained respiratory rates associated with the user. The energy projected by the first light source and the energy projected by second light source each have the same wavelength. In some embodiments, the multichannel signal comprises a multichannel photoplethysmogram (PPG) signal.

DETAILED DESCRIPTION

Biometrics including blood metrics may be measured by minimally invasive procedures to address medical conditions such as diabetes or in the diagnosis and discovery of diseases. Minimal-invasive procedure based devices may have the advantages of reducing costs and decreasing the need for invasive methods, thereby increasing the comfort and well-being of users and patients. Even though these devices have revolutionized patient care, they have only been described in, and approved for, medical purposes. Minimal-invasive procedure based devices are usually out of reach for the general public because they are designed for medical uses rather than non-medical purposes such as fitness, well-being, and quality of life.

Personal devices such as sphygmomanometers or pulse oximeters measure blood pressure or oxygen levels, respectively, on a per-request basis. They usually cannot measure blood metrics real time or periodically. Real-time blood metrics data (e.g., high resolution measurements, or measurements over long periods of time) may allow these devices to facilitate users monitoring and controlling their energy levels and/or metabolism. Nutritionists, people suffering from obesity, people desiring to eat healthier, fitness enthusiasts, semi-professional athletes, people likely to have hypoglycemia, or the vast majority of the general population can benefit from these devices.

In various embodiments, a multispectral blood metric measurement apparatus monitors blood metrics, fitness, and/or metabolism levels of various users in a non-invasive manner. The multispectral blood metric measurement apparatus may be, for example, wearable technology. The multispectral blood metric measurement apparatus may measure any number of blood metrics. Blood metrics may include, for example, various nutrient blood concentrations. Blood metrics may be, for example, monitored, stored, tracked, and/or analyzed.

Figure 1:
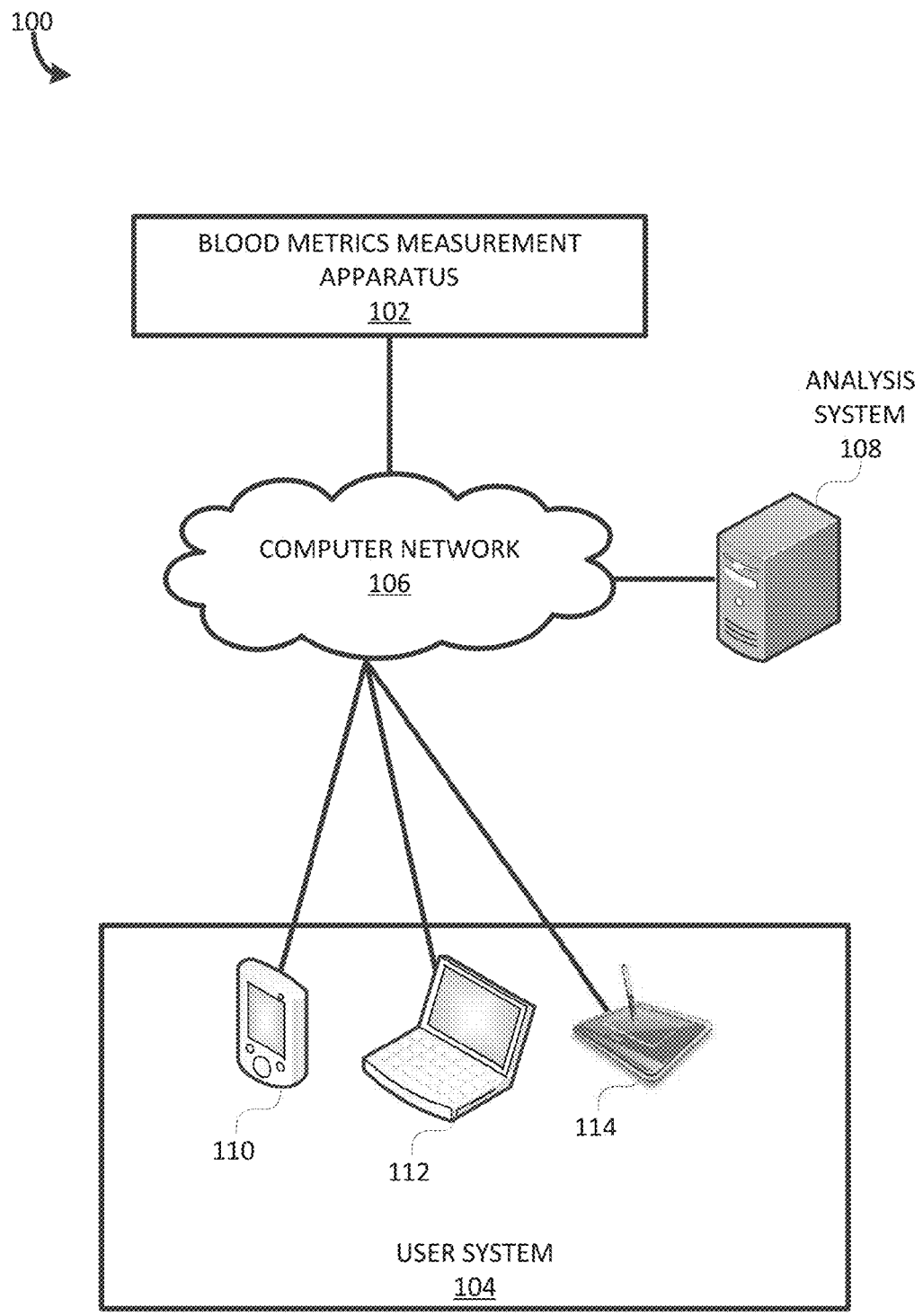
FIG. 1 is a block diagram illustrating an example environment utilizing a multispectral blood metrics measurement apparatus in accordance with various embodiments.

FIG. 1 is a block diagram illustrating an example environment 100 utilizing a multispectral blood metrics measurement apparatus 102 in accordance with various embodiments. As shown in FIG. 1, the example environment 100 may comprise a multispectral blood metrics measurement apparatus 102, one or more user systems 104, an optional analysis system 108, and a computer network 106 communicatively coupling together each of the multispectral blood metrics measurement apparatus 102, one or more user devices 110, 112, and 114 (depicted as user system 104), and/or the analysis system 108. As shown, a user system 104 may include a smartphone 110 (e.g., iPhone®), a computer 112 (e.g., a personal computer), and/or a tablet 114 (e.g., iPad®), through the computer network 106 (e.g., a Bluetooth® 4.0 personal area network), can either interact directly or indirectly with the blood metrics measurement apparatus 102.

The multispectral blood metrics measurement apparatus 102 may measure health or metabolism predictors non-invasively. The multispectral blood metrics measurement apparatus 102 may measure blood metrics such as concentrations of various nutrients over time, deliver energy into tissues of various body parts of a user, track a user's behavior pattern, detect motion, communicate various blood metric measurements, and/or receive a user's instructions. For instance, through the computer network 106, the multispectral blood metrics measurement apparatus 102 may transmit one or more blood metric measurements to, or receive instructions from, the user system 104 or the multispectral blood measurement system 108 such as which health or metabolism predictor to measure.

In some embodiments, the multispectral blood metric 102 measurement apparatus may project energy into tissue of a user and detect energy reflected from and/or transmitted through tissue of the user (e.g., the wearer of the multispectral blood metric measurement apparatus 102). The projected energy may be at multiple wavelengths that are associated with the blood metrics of interest to a user. The detected energy may be a fraction of the energy that is projected into the tissue. Energy at different wavelengths may be absorbed at a different rate that is related to a user's body state. The user's body state (e.g., heart rate, blood pressure, nutrient level, or the like) determines the amount of absorbed energy. Accordingly, energy at different wavelengths may be absorbed at different levels by a user's body. The fraction of energy received (e.g., that is reflected by the tissue or transmitted through the tissue) may be used to generate signals (e.g., composite signals) at different levels. These signals may provide information of the user's body state. This information may be obtained by analyzing waveforms of the signal in the time domain and/or the frequency domain.

In various embodiments, the multispectral blood metric measurement apparatus 102 may measure many metrics, including, but not limited to, skin conductivity, pulse, oxygen blood levels, blood pressure, blood glucose level, glycemic index, insulin index, Vvo2max, fat body composition, protein body composition, blood nutrient level (e.g., iron), body temperature, blood sodium levels, and/or naturally-produced chemical compound level (e.g., lactic acid). Nutrients may be determined based on the blood metrics to be measured. Nutrients may be measured may include, but are not limited to, glucose, hemoglobin, triglycerides, cholesterol, bilirubin, protein, albumin (i.e., egg white), and/or electrolytes (e.g., sodium, potassium, chloride, bicarbonate, etc.)

It will be appreciated that the user's body state may change dynamically and energy at a wavelength may be absorbed differently by a user over the time. By monitoring and tracking detected energy from the user's body, a user's health or condition may be more tracked. Systems and methods described herein may monitor and store blood metrics including concentrations of various nutrients. A user's history health records may be generated by using blood metrics measured at different times. In some embodiments, blood metrics measured a given time point may be compared to the history health records to detect any abnormal health conditions. The multispectral blood metric measurement apparatus may comprise a user interface where a user may input blood metrics of interest, be presented with various health reports, and/or be alerted with abnormal health conditions.

A user may comfortably wear a multispectral blood metric measurement apparatus 102 over time. The multispectral blood metric measurement apparatus 102 may comprise lightweight components. The multispectral blood metric measurement apparatus 102 may be made of hypoallergenic materials. The multispectral blood metric measurement apparatus 102 may be flexibly built so that it could fit various body parts (e.g., wrist, earlobe, ankle, or chest) of a user.

In accordance with some embodiments, the computer network 106 may be implemented or facilitated using one or more local or wide-area communications networks, such as the Internet, WiFi networks, WiMax networks, private networks, public networks, personal area networks ("PAN"), and the like. In some embodiments, the computer network 106 may be a wired network, such as a twisted pair wire system, a coaxial cable system, a fiber optic cable system, an Ethernet cable system, a wired PAN constructed with USB and/or FireWire connections, or other similar communication network. Alternatively, the computer network 106 may be a wireless network, such as a wireless personal area network, a wireless local area network, a cellular network, or other similar communication network. Depending on the embodiment, some or all of the communication connections with the computer network 106 may utilize encryption (e.g., Secure Sockets Layer [SSL]) to secure information being transferred between the various entities shown in the example environment 100.

Although FIG. 1 depicts a computer network 106 supporting communication between different digital devices, it will be appreciated that the multispectral blood metrics measurement apparatus may be directly coupled (e.g., over a cable) with any or all of the user devices 110, 112, and 114.

The user devices 110-114 may include any digital device capable of executing an application related to measuring blood metrics, presenting an application user interface through a display and/or communicating with various entities in the example environment 100 through the computer network 106. For instance, through the computer network 106, the user device 110 may receive one or more blood metric measurements from the multispectral blood metrics measurement apparatus 102, track and store the blood metric measurements, analyze the blood metric measurements, and/or provide recommendations based on the blood metric measurements. An application user interface may facilitate interaction between a user of the user system 104 and an application running on the user system 104.

In various embodiments, any of user devices 110-114 may perform analysis of the measurements from the multispectral blood metrics measurement apparatus 102, display results, provide reports, display progress, display historic readings, track measurements, track analysis, provide alerts, and/or the like.

The analysis system 108 may be any form of digital device capable of executing an analysis application for analyzing and/or measuring blood metrics. In some embodiments, the analysis system 108 may generate reports or generate alerts based on analysis or measurement of blood metrics. For instance, through the computer network 106, the analysis system 108 may receive one or more blood metric measurements from the multispectral blood metrics measurement apparatus 102, track and store blood metric measurements, analyze blood metric measurements, and/or provide recommendations based on the analysis. An application programming interface may facilitate interaction between a user, the user devices 110-114, and/or the multispectral blood metrics measurement apparatus 110 with the analysis system 108.

Computing devices (e.g., digital devices) may include a mobile phone, a tablet computing device, a laptop, a desktop computer, personal digital assistant, a portable gaming unit, a wired gaming unit, a thin client, a set-top box, a portable multi-media player, or any other type of network accessible user device known to those of skill in the art. Further, the analysis system 108 may comprise of one or more servers, which may be operating on or implemented using one or more cloud-based services (e.g., System-as-a-Service [SaaS], Platform-as-a-Service [PaaS], or Infrastructure-as-a-Service [IaaS]).

It will be understood that for some embodiments, the components or the arrangement of components may differ from what is depicted in FIG. 1.

Each of the multispectral blood metrics measurement apparatus 102, one or more user devices 110, 112, and 114, and the analysis system 108 may be implemented using one or more digital devices. An exemplary digital device is described regarding FIG. 8.

Figure 2:
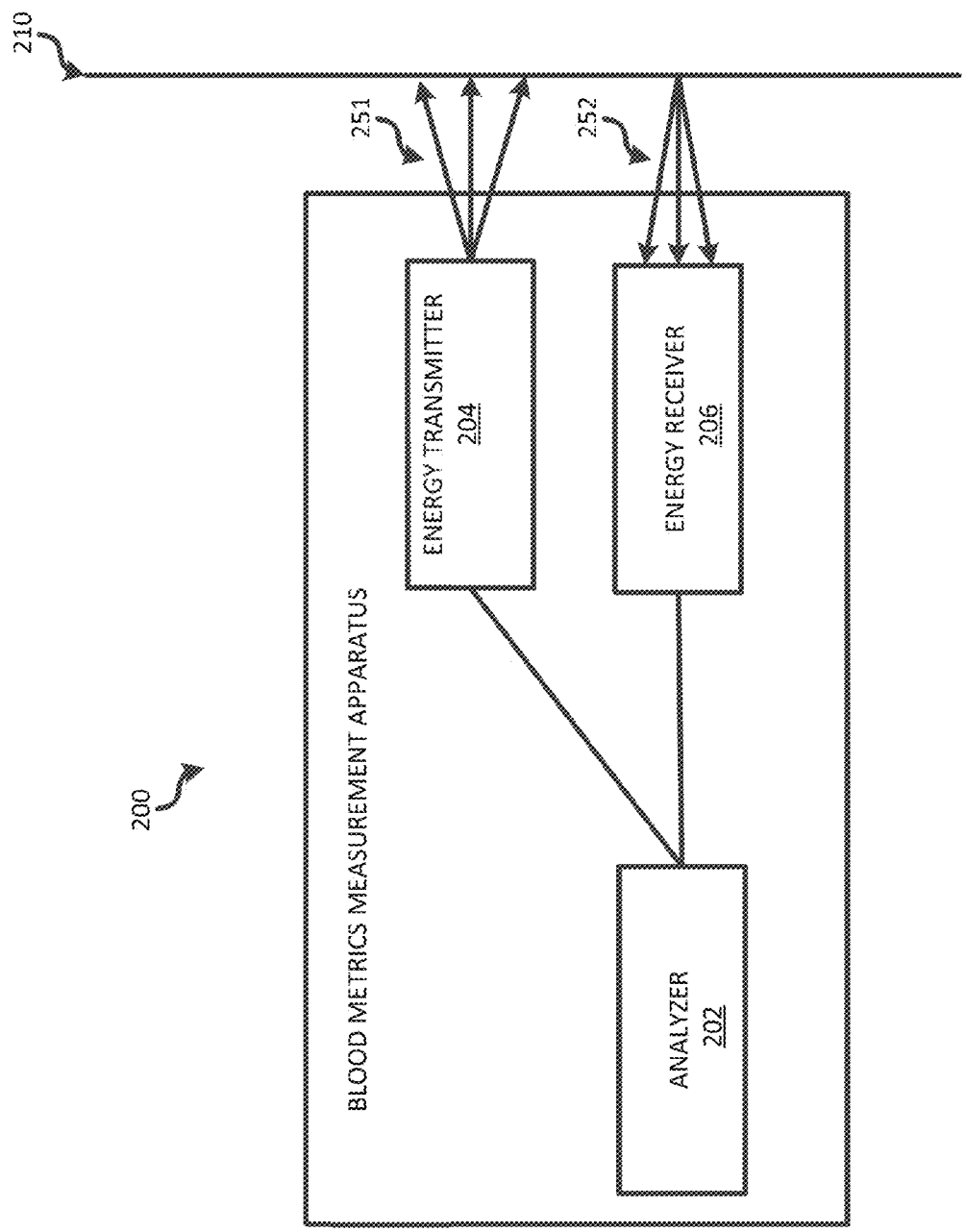
FIG. 2 is a block diagram illustrating an exemplary multispectral blood metrics measurement apparatus, such as the multispectral blood metrics measurement apparatus illustrated in FIG. 1.

FIG. 2 is a block diagram illustrating an exemplary multispectral blood metrics measurement apparatus 200, such as the multispectral blood metrics measurement apparatus 102 illustrated in FIG. 1. The multispectral blood metrics measurement apparatus 200 comprises an analyzer 202, an energy transmitter 204, and an energy receiver 206. Various embodiments may comprise a wearable member. The wearable member may include, for example, a bracelet, glasses, necklace, ring, anklet, belt, broach, jewelry, clothing, or any other member of combination of members that allow the multispectral blood metrics measurement apparatus 200 to be close to or touch a body of the wearer.

The energy transmitter 204 and the energy receiver 206 may be secured to the wearable member such that the energy transmitter and the energy receiver may make contact or be in proximity with tissues (e.g., skin) of a user. The analyzer 202 may be coupled to the energy transmitter 204 and the energy receiver 206. In further embodiments, the multispectral blood metrics measurement apparatus 200 may comprise a communication module (not shown). The communication module may be coupled to the analyzer 202. The blood metrics measurement apparatus 200 may further comprise a driver (not shown) and a power source (not shown). The driver may be coupled to the energy transmitter 204 and the analyzer 202. The analyzer 202 may be coupled to the energy transmitter 204 via the driver. The power source may be coupled to the energy transmitter 204 via the driver. The blood metrics measurement apparatus 200 may further comprise an Analog-to-Digital Converter ("ADC") (not shown). The ADC may be coupled to the energy receiver 206 and the analyzer 202. In some embodiments, the blood metrics measurement apparatus 200 may comprise a motion sensor (e.g., an accelerometer, gyroscope, global positioning system, or the like) (not shown). The motion sensor may be coupled to the analyzer 202.

In various embodiments, the energy transmitter 204 emits energy including, but not limited to, light, into the body of the user. The energy produced by the energy transmitter may be in the direction of entering tissues. For example, the energy produced by the energy transmitter 204 is in a direction 251 entering the tissue 210. In some embodiments, the energy transmitter 204 emits energy or light at different wavelengths. The energy transmitter 204 may comprise any number of light emission diodes ("LEDs"). In some embodiments, the energy transmitter 204 comprises at least two LEDs. Each LED may be configured to emit energy at one or more wavelengths. In another example, each LED may emit light with a peak wavelength centered around a wavelength. In one example, the energy transmitter 204 may emit light with a peak wavelength centered around 500 nm to 1800 nm.

Each wavelength may correspond to one or more blood metrics of interest and/or one or more nutrients. It will be appreciated that different components of the blood and/or different nutrients may absorb energy at different wavelengths. In various embodiments, a controller, driver, analyzer 202, or the like may receive a blood metric or nutrient of interest (e.g., from a user of the multispectral blood metrics measurement apparatus 200 and/or a user device not shown). The controller, driver, analyzer 202 or the like may associate the blood metric and/or nutrient of interest with one or more wavelengths and configure one or more of the LEDs to emit energy of at least one of the one or more wavelengths. For example, the analyzer 202 may command the driver to deliver electric power to one LED that is configured to emit light at the desired wavelength.

The energy receiver 206 may detect energy associated with the energy provided by the LEDs from tissues (e.g., skin) of the user. In this example, received and/or detected energy is in the direction 252 that leaves from the tissue 210. In various embodiments, the energy receiver 206 may detect energy from the body of the user that is a fraction of the energy produced by the energy transmitter 204.

The energy transmitter 204 and the energy receiver 206 may be configured such that the energy receiver 206 detects reflected energy from tissues of the user of the multispectral blood metrics measurement apparatus 200. For example, the energy transmitter 204 and the energy receiver 206 may be configured to be disposed on one surface or side of a user's tissue. The energy transmitter 204 and the energy receiver 206 may be configured such that the energy receiver 206 detects energy from the energy transmitter 204 that passes through or reflects from the user's tissues. In some embodiments, the energy transmitter 204 and the energy receiver 206 may be configured to be disposed on different (e.g., opposite) surfaces or sides of a users' tissue.

Energy detected from tissues of a user may be detected by the energy receiver 206. The energy receiver 206 may be configured to generate a signal in response to the detected energy. In some embodiments, the energy receiver 206 may be triggered by the energy received to generate an output which may be dependent or partially dependent upon the amount of energy received. The energy receiver 206 may be configured to generate a signal (e.g., an electric current, or an electric voltage) in response to the energy received from the tissues.

The signal generated by the energy receiver 206 may be associated with one or more blood metrics and/or nutrients of interest. Energy at different wavelengths may be absorbed at a different rate that is related to a user's body state. The user's body state (e.g., heart rate, blood pressure, nutrient level, or the like) may determine the amount of energy absorbed by the body. Accordingly, energy from the user's body at different wavelengths may be detected at different levels thereby causing different responses of the energy receiver 206. The energy receiver 206 may, for example, output signals based on the level of the energy received.

The energy receiver 206 may provide information associated with the user's body state. Blood metric information may be determined (e.g., by the analyzer 202) from the output signal of the energy receiver 206.

The energy receiver 206 may comprise a set of photodetectors (e.g., a photo diode, or a photo transistor) which are configured to output a signal dependent upon photons or the like from the energy transmitter 204 that passed through tissues of the user.

In various embodiments, the output signal of the energy receiver 206 is a composite of multiple signals. Each signal of the composite may be associated with energy at a wavelength which may be a portion (or fraction) of the total energy emitted by the energy transmitter 204.

The energy transmitter 204 may be configured to generate energy at a set of wavelengths. In some embodiments, the energy transmitter 204 is configured to generate energy such that energy at different wavelengths is generated sequentially and/or periodically. The energy transmitter 204 may be configured to generate energy at each particular wavelength until energy at all wavelengths of the set is generated. The period of time for the energy transmitter 204 to generate energy at all wavelengths is a generation period. Subsequent to completion of the generation period, the energy transmitter 204 may start a new generation period thereby allowing multiple measurements.

In some embodiments, the blood metrics measurement apparatus 200 may be or include the blood metrics measurement apparatus 102 described with regard to FIG. 1.

Figure 3:
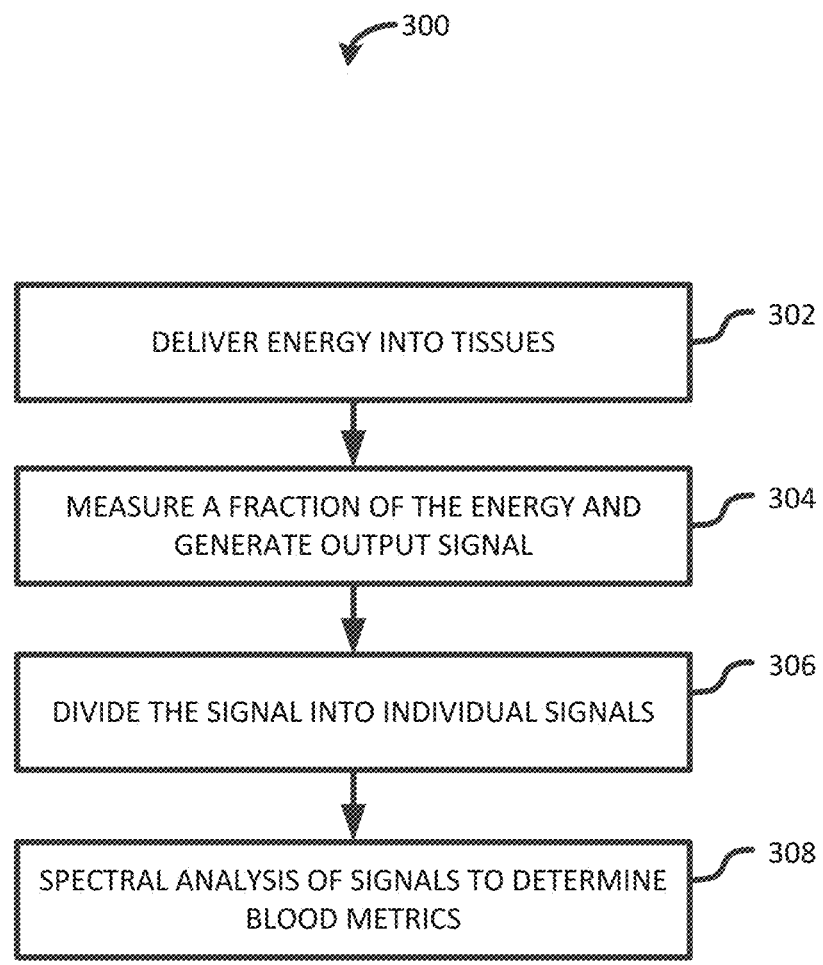
FIG. 3 illustrates an exemplary flow diagram of a method of measuring blood metrics in accordance with an embodiment of the present application.

FIG. 3 illustrates an exemplary flow diagram of a method 300 of measuring blood metrics in accordance with an embodiment of the present application. At step 302, energy transmitter 204 generates and delivers energy at different wavelengths into tissues (e.g., skin) of a user. Different wavelengths may be associated with any number of nutrients, which may be associated with the blood metrics to be measured.

In some embodiments, a user may define various blood metrics and/or nutrients to be measured. Referring back to FIG. 1, a list of blood metrics and/or nutrients may be selected from a user interface (e.g., displayed on an interface of the multispectral blood metrics measurement apparatus 102, on a user device 110-114, or through the analysis system 108). The user may select one or more blood metrics and/or nutrients to be measured.

In some embodiments, a user may define a set of blood metrics to be measured on the user system 104; the multispectral blood metrics measurement apparatus 102 may provide the blood metrics to be measured to the user system 104. For example, on any device of the user system 104, a user may define one or more blood metrics by selecting one or more blood metrics from a list of blood metrics provided, for example, via the user interface.

As discussed herein, the multispectral blood metrics measurement apparatus 200 may measure, but is not limited to, skin conductivity, pulse, oxygen blood levels, blood pressure, blood glucose level, glycemic index, insulin index, Vvo2max, fat body composition, protein body composition, blood nutrient level (e.g., iron), body temperature, blood sodium levels, or naturally-produced chemical compound level (e.g., lactic acid). Nutrients may be determined based on the blood metrics to be measured. The multispectral blood metrics measurement apparatus 200 may measure nutrients, but is not limited to, glucose, hemoglobin, triglycerides, cholesterol, bilirubin, protein, albumin (i.e., egg white), or electrolytes (e.g., sodium, potassium, chloride, bicarbonate, or the like). The multispectral blood metrics measurement apparatus 200 may also measure oxygen, cortisol, and Hematocrit, for example (e.g., blood components).

In various embodiments, one or more wavelengths may be associated with a nutrient or a combination of blood components or molecules. In some embodiments, a number of wavelengths generated by the energy transmitter 204 are the number of blood components or molecules to be measured plus one. For example, when a total number of five (5) blood components and/or molecules are to be measured, a total number of six (6) wavelengths may be determined based on the blood components and/or molecules to be measured. Similarly, it will be appreciated that one or more wavelengths may be associated with a nutrient or a combination of nutrients. In some embodiments, a number of wavelengths generated by the energy transmitter 204 are the number of nutrients to be measured plus one. For example, when a total number of three (3) nutrients are to be measured, a total number of four (4) wavelengths may be determined based on the nutrients to be measured.

In some embodiments, the multispectral blood metrics measurement apparatus 200, user devices 110-114, and/or analysis system 108 may comprise a reference table of blood components, molecules, and/or nutrients and wavelengths corresponding to the blood components, molecules, and/or nutrients. A wavelength may be unique to or more generally associated with a nutrient. A reference wavelength may be unique to or more generally associated with a combination of nutrients to be measured. As such, wavelength(s) may be determined by looking up each blood components, molecules, and/or nutrients that is to be measured. Energy at the determined wavelengths may be transmitted by the energy transmitter 204 into the body.

In various embodiments, in a predetermined time duration, energy at all desired wavelengths may be generated. For each wavelength, the corresponding energy may be generated for a time period equal to a predetermined time duration divided by the number of wavelengths. For example, four (4) wavelengths may be determined and the predetermined time duration is two (2) seconds. Accordingly, energy for each wavelength may be generated for a duration of half (0.5) second.

At step 304, the energy receiver 206 detects a fraction of the energy transmitted into the user's tissue by the energy transmitter 204. The energy receiver 206 may generate a signal based on the fraction of energy detected (e.g., based on the amount of the energy detected). In one example, energy detected at step 304 may be a fraction of the energy generated at step 302 reflected by the tissue. Energy detected at step 302 may be a fraction of the energy generated at step 302 that passes through the tissue (e.g., other undetected energy may be absorbed by tissue and/or otherwise blocked). The output signal of the energy receiver 206 may be an electric current or an electric voltage, of which the amplitude may be related to the amount of the energy detected. In various embodiments, steps 302 and 304 are performed simultaneously. That is, energy generation and detection may be performed approximately simultaneously.

In various embodiments, the output signal generated by the energy receiver 206 is a composite signal of multiple signals, each of which corresponds to one or more wavelengths. The output signal produced at step 306 may be divided into individual signals, each of which is may be associated with one or more wavelengths.

In various embodiments, analysis of the signals from the energy receiver 206 may identify abnormal measurements. For example, each of the measurement may be compared to a predetermined value. If the difference between the measurement and the predetermined value is above (or below) a threshold, then the measurement may be determined to be abnormal. An abnormal value may trigger additional analysis or an alert. In some embodiments, an abnormal value is ignored (e.g., as possibly effected by noise caused by movement of the energy transmitter 204 and/or the energy receiver 206). In various embodiments, the abnormal value may be discounted (e.g., the weight of the value reduced). The degree of discount may be based, for example, on information from an accelerometer (e.g., a large acceleration may indicate that the abnormal value should be significantly discounted) and/or based on historical values. It will be appreciated that the degree of discount may be based on any number of factors.

In some embodiments, measurements may be averaged over a period of time. A Kalman filer (e.g., a nonlinear, unscented Kalman filter) may be applied to any number of measurements or averaged measurements. A motion measurement (e.g., a measurement by an accelerometer) may be considered. Upon determining a measurement is abnormal, the motion measurement for that time point may be inspected. A large measurement may indicate large vibrations or accelerations that corroborate that the measurement may be abnormal. Measurements collected in such situations are likely to have significant electrical noises.

At step 308, the analyzer 202 may analyze signals from the energy receiver 206 analyzed in the frequency domain to determine blood metrics. Concentration of a nutrient in the blood may subsequently be determined. In some embodiments, signals may be provided to a bandpass filter that separates AC components from DC components. An AC component may represent signal variation at the cardiac frequency and a DC component may represent the average overall transmitted light intensity. In some embodiments, a heart rate and/or oxygen saturation, $SpO_2$ may be determined. The heart rate may be determined, for example, by averaging the maximum frequency to determine the rate of cardiac beats in a predetermined amount of time. The oxygen saturation $SpO_2$ may be determined according to Equation (1):

$$S_pO_2 = 110 - 25 \times R \tag{1}$$

where R is the ratio of a red and infrared normalized transmitted light intensity. R may be determined according to Equation (2):

$$R = \frac{AC_R/DC_R}{AC_{IR}/DC_{IR}}, \tag{2}$$

where the $AC_R$ is the AC component of the detected energy corresponding to a wavelength (e.g., red light), $DC_R$ is the DC component of the detected energy corresponding to the wavelength (e.g., red light), $AC_{IR}$ is the AC component of the detected energy corresponding to a different wavelength (e.g., infrared light), and $DC_{IR}$ is the DC component of the detected energy corresponding to the different wavelength (e.g., infrared light). In some embodiments, the AC component may be selected as the highest spectral line in the cardiac frequency band. Waveform analysis may be performed to determine the R-R interval defined by two successive AC components, an elapsed interval and the perturbation, if there is any.

It will be appreciated that analysis may be performed by the analyzer 202 and/or any other digital device (e.g., any of users devices 110-114 or analysis system 108).

At step 308, state space estimation and progression may be performed to determine blood metrics. A system may be modeled according to Equation (3):

$$x(n+1) = f[x(n)] + u(n)$$
$$y(n) = h[x(n)] + v(n) \quad (3)$$

where x(n) represents the state of the system, u(n) is process noise, y(n) is the vector of the observed signals, and v(n) is the measurement noise.

Table 1 lists one or more parameters for x(n) as well as their initial value in some embodiments:

TABLE 1

| Parameter | Symbol | Initial Value |
|---|---|---|
| Cardiac frequency | $f_{HR}$ | 1 Hz |
| Cardiac phase | $\theta_{HR}$ | 0 |
| Cardiac harmonic amplitude | $I_{Harmonic}^{HR}$ | 0 |
| Cardiac Pulse Pressure | $P_{HR}$ | 1 |
| Point Blood Pressure | $P_{Point}$ | 1 |
| Respiratory frequency | $f_{Resp}$ | 0.3 Hz |
| Respiratory phase | $\theta_{Resp}$ | 0 |
| Wavelength i = 1 ... N AC peak amplitude | $I_{\lambda_i}^{AC}$ | 0.5 max_value |
| Wavelength i = 1 ... N AC peak location | $pos_{\lambda_i}^{AC}$ | Corresponding FFT bin to 1 Hz |
| Wavelength i = 1 ... N DC | $I_{\lambda_i}^{DC}$ | 0.5 max_value |
| Wavelength i = 1 ... N p2p amplitude | $I_{\lambda_i}^{p2p}$ | 1 ADC read |
| Wavelength i = 1 ... N rise time | $\tau_{\lambda_i}^{rise}$ | 0.1 sec |
| Wavelength i = 1 ... N Significance coefficient | $c_{\lambda_i}$ | 1 |
| Wavelength i = 1 ... N HRV | $T_{\lambda_i}^{HRV}$ | 1 sec |
| Best Ratio pH | $BR_{pH}$ | 2 |
| Best Ratio pCO2 | $BR_{pCO2}$ | 3 |
| Best Ratio pHCO3− | $BR_{pHCO3-}$ | 4 |
| Acceleration magnitude | $I_{move}$ | 0 |
| GPS velocity | $|v|_{GPS}$ | 0 |
| GPS altitude | $|alt|_{GPS}$ | 0 |
| GPS acceleration | $|a|_{GPS}$ | 0 |
| GPS incline | $|incline|_{GPS}$ | 0 |
| Restfulness | Rest | 0 |
| Hydration | Hyd | 0 |
| Systolic Blood Pressure | SBP | 120 mmHg |
| Diastolic Blood Pressure | DBP | 80 mmHg |
| End tidal CO2 | ETCO2 | 40 mmHg |
| Blood Carbon Monoxide | SpCO | 0% |

Table 2 lists one or more parameters for y(n) as well as their initial value in some embodiments:

TABLE 2

| Parameter | Symbol | Initial |
|---|---|---|
| Blood pH | pH | 7.35 |
| Blood PCO2 | $pCO_2$ | 24 mmol |
| Blood PO2 | $pO_2$ | 24 mmol |
| Blood PHCO3− | $pHCO_3^-$ | 24 mmol |
| Blood Glucose | $pC_6H_{12}O_6$ | 3 mmol |
| Cardiac Frequency | $f_{HR}$ | 1 |
| Point Blood Pressure | $P_{Point}$ | 1 |
| Respiratory Frequency | $f_{Resp}$ | 0.3 Hz |
| GPS velocity | $|v|_{GPS}$ | 0 |
| GPS altitude | $|alt|_{GPS}$ | 0 |
| GPS acceleration | $|a|_{GPS}$ | 0 |
| GPS incline | $|incline|_{GPS}$ | 0 |

Table 3 lists the state space model F(X(n)) between the parameters listed in Table 1 and Table 2 in some embodiments, where the energy wavelengths comprise 880 nm, 631 nm, 1450 nm, and 1550 nm:

TABLE 3

| Name | Symbol | Equation |
|---|---|---|
| Cardiac frequency | $f_{HR}$ | $bin\_to\_freq\left(\dfrac{\sum c_{\lambda_i} pos_{\lambda_i}^{AC}}{\sum c_{\lambda_i}}\right)$ |
| Cardiac phase | $\theta_{HR}$ | $\theta_{HR}(n-1) + f_s^{-1} * \omega^*$, where $\omega^* \in [\omega\_min, \omega\_max]$ |
| Cardiac harmonic amplitude | $I_{Harmonic}^{HR}$ | $\dfrac{\sum c_{\lambda_i} I_{\lambda_i}^{p2p}}{\sum c_{\lambda_i}}$ |
| Cardiac Pulse Pressure | $P_{HR}$ | $\left(\dfrac{\sum c_{\lambda_i} \tau_{\lambda_i}^{rise}}{\sum c_{\lambda_i}}\right)^\wedge -1$ |
| Point Blood Pressure | $P_{Point}$ | $\tau_{\lambda,1}^{rise-1}$ |
| Respiratory frequency | $f_{Resp}$ | |

3) Respiratory and Heart Rate State Models: The fluctuations in the respiratory rate $\omega_r(n)$ and fluctuations in the heart rate $\omega_{ca}(n)$ that are not due to RSA are both modeled as a first-order autoregressive process with a mean and mild nonlinearity that limit the frequencies to know physiologic ranges $$\omega_r(n+1) = \overline{\omega}_r + \alpha_r\{s_r[\omega_r(n)] - \overline{\omega}_{cr}\} + u_{\omega_r}(n) \quad (15)$$

$$\omega_{ca}(n+1) = \overline{\omega}_c + \alpha_c\{s_c[\omega_{ca}(n)] - \overline{\omega}_r\} + u_{\omega_{ca}}(n) \quad (16)$$

where $\overline{\omega}_r$ and $\overline{\omega}_c$ are the a priori estimates of the expected respiratory and cardiac frequencies, respectively; $\alpha_r$ and $\alpha_c$ control the bandwidth of the frequency fluctuations; and $u_{\omega_r}(n)$ and $u_{\omega_{ca}}(n)$ are white noise processes that model the random variation in the respiratory and cardiac frequencies, respectively.

The instantaneous respiratory and heart rates in units of Hz are then $$f_r(n) = \dfrac{1}{2\pi T_s} s_r[\omega_r(n)] \quad (17)$$

$$f_c(n) = \dfrac{1}{2\pi T_s} s_c[\omega_c(n)]. \quad (18)$$

| Name | Symbol | Equation |
|---|---|---|
| Respiratory phase | $\theta_{Resp}$ | $\theta_{Resp}(n-1) + f_s^{-1} * \omega^*$, where $\omega^* \in [\omega\_min, \omega\_max]$ |
| $\lambda = 880$ nm AC peak | $I_{\lambda_i}^{AC}$ | From FFT |
| $\lambda = 880$ nm DC | $pos_{\lambda_i}^{AC}$ | From FFT |
| $\lambda = 880$ nm p2p amplitude | $I_{\lambda_i}^{DC}$ | From Waveform analysis |
| $\lambda = 880$ nm rise time | $I_{\lambda_i}^{p2p}$ | From Waveform analysis |
| $\lambda = 880$ nm signal trend | $\tau_{\lambda_i}^{rise}$ | From Waveform analysis |
| $\lambda = 880$ nm Significance coefficient | $c_{\lambda_i}$ | From Waveform analysis |
| $\lambda = 880$ nm HRV | $T_{\lambda_i}^{HRV}$ | From Waveform analysis |
| $\lambda = 631$ nm AC peak | $I_{\lambda_i}^{AC}$ | From Fast Fourier Transformation ("FFT") |
| $\lambda = 631$ nm DC | $pos_{\lambda_i}^{AC}$ | From FFT |
| $\lambda = 631$ nm p2p amplitude | $I_{\lambda_i}^{DC}$ | From Waveform analysis |

TABLE 3-continued

| Name | Symbol | Equation |
|---|---|---|
| $\lambda$ = 631 nm rise time | $I_{\lambda_i}^{p2p}$ | From Waveform analysis |
| $\lambda$ = 631 nm signal trend | $\tau_{\lambda_i}^{rise}$ | From Waveform analysis |
| $\lambda$ = 631 nm Significance coefficient | $c_{\lambda_i}$ | From Waveform analysis |
| $\lambda$ = 631 nm HRV | $T_{\lambda_i}^{HRV}$ | From Waveform analysis |
| $\lambda$ = 1450 nm AC peak | $I_{\lambda_i}^{AC}$ | From FFT |
| $\lambda$ = 1450 nm DC | $pos_{\lambda_i}^{AC}$ | From FFT |
| $\lambda$ = 1450 nm p2p amplitude | $I_{\lambda_i}^{DC}$ | From Waveform analysis |
| $\lambda$ = 1450 nm rise time | $I_{\lambda_i}^{p2p}$ | From Waveform analysis |
| $\lambda$ = 1450 nm signal trend | $\tau_{\lambda_i}^{rise}$ | From Waveform analysis |
| $\lambda$ = 1450 nm Significance coefficient | $c_{\lambda_i}$ | From Waveform analysis |
| $\lambda$ = 1450 nm HRV | $T_{\lambda_i}^{HRV}$ | From Waveform analysis |
| $\lambda$ = 1550 nm AC peak | $I_{\lambda_i}^{AC}$ | From FFT |
| $\lambda$ = 1550 nm DC | $pos_{\lambda_i}^{AC}$ | From FFT |
| $\lambda$ = 1550 nm p2p amplitude | $I_{\lambda_i}^{DC}$ | From Waveform analysis |
| $\lambda$ = 1550 nm rise time | $I_{\lambda_i}^{p2p}$ | From Waveform analysis |
| $\lambda$ = 1550 nm signal trend | $\tau_{\lambda_i}^{rise}$ | From Waveform analysis |
| $\lambda$ = 1550 nm Significance coefficient | $c_{\lambda_i}$ | From Waveform analysis |
| $\lambda$ = 1550 nm HRV | $T_{\lambda_i}^{HRV}$ | From Waveform analysis |
| Best Ratio pH | $BR_{pH}$ | Device Calibration |
| Best Ratio pCO2 | $BR_{pCO2}$ | Device Calibration |
| Best Ratio pHCO3- | $BR_{pHCO3-}$ | Device Calibration |
| Acceleration magnitude | $I_{move}$ | From Accelerometer |
| GPS velocity | $|v|_{GPS}$ | From GPS |
| GPS altitude | $|alt|_{GPS}$ | From GPS |
| GPS acceleration | $|a|_{GPS}$ | From GPS |
| GPS incline | $|incline|_{GPS}$ | From GPS |

TABLE 4

Table 4 lists Y(n) = H(x(n)):

| Name | Symbol | Equation |
|---|---|---|
| Blood pH | pH | $6.1 + \log\left(\dfrac{pHCO_3^-}{0.03 pCO_2}\right)$ |
| Blood PCO2 | $pCO_2$ | $\dfrac{\epsilon_{Hb}^{CO_2} - \epsilon_{Hb}^{Hb} * I_{\lambda_{CO_2}}^{AC} * I_{\lambda_1}^{DC} / \left(I_{\lambda_1}^{AC} * I_{\lambda_{CO_2}}^{DC}\right)}{\epsilon_{Hb}^{CO_2} - \epsilon_{CO_2}^{CO_2} + \left(\epsilon_{CO_2}^{Hb} - \epsilon_{Hb}^{Hb}\right) * I_{\lambda_{CO_2}}^{AC} * I_{\lambda_1}^{DC} / \left(I_{\lambda_1}^{AC} * I_{\lambda_{CO_2}}^{DC}\right)}$ |
| Blood PO2 | $pO_2$ | $\dfrac{\epsilon_{Hb}^{O_2} - \epsilon_{Hb}^{Hb} * I_{\lambda_{O_2}}^{AC} * I_{\lambda_1}^{DC} / \left(I_{\lambda_1}^{AC} * I_{\lambda_{O_2}}^{DC}\right)}{\epsilon_{Hb}^{O_2} - \epsilon_{O_2}^{O_2} + \left(\epsilon_{O_2}^{Hb} - \epsilon_{Hb}^{Hb}\right) * I_{\lambda_{O_2}}^{AC} * I_{\lambda_1}^{DC} / \left(I_{\lambda_1}^{AC} * I_{\lambda_{O_2}}^{DC}\right)}$ |
| Blood PHCO3- | $pHCO_3^-$ | $\dfrac{\epsilon_{Hb}^{HCO_3^-} - \epsilon_{Hb}^{Hb} * I_{\lambda_{HCO_3^-}}^{AC} * I_{\lambda_1}^{DC} / \left(I_{\lambda_1}^{AC} * I_{\lambda_{HCO_3^-}}^{DC}\right)}{\epsilon_{Hb}^{HCO_3^-} - \epsilon_{HCO_3^-}^{HCO_3^-} + \left(\epsilon_{HCO_3^-}^{Hb} - \epsilon_{Hb}^{Hb}\right) * I_{\lambda_{HCO_3^-}}^{AC} * I_{\lambda_1}^{DC} / \left(I_{\lambda_1}^{AC} * I_{\lambda_{HCO_3^-}}^{DC}\right)}$ |
| Blood Glucose | $pC_6H_{12}O_6$ | As above |
| Cardiac Frequency | $f_{HR}$ | As in f(x(n)) |
| Point Blood Pressure | $P_{Point}$ | As in f(x(n)) |
| Respiratory Frequency | $f_{Resp}$ | As in f(x(n)) |
| GPS velocity | $|v|_{GPS}$ | As in f(x(n)) |
| GPS altitude | $|alt|_{GPS}$ | As in f(x(n)) |
| GPS acceleration | $|a|_{GPS}$ | As in f(x(n)) |
| GPS incline | $|incline|_{GPS}$ | As in f(x(n)) |

As illustrated in Tables 3 and 4, by generating energy at different wavelengths, one or more blood metrics may be determined from the detected energy. For example, cardiac frequency, cardiac phase, cardiac harmonic amplitude, cardiac pulse pressure, point blood pressure, respiratory frequency, respiratory phase, blood pH, blood $pCO_2$, blood $pHCO_{3-}$, or blood glucose, may be determined.

Figure 4:
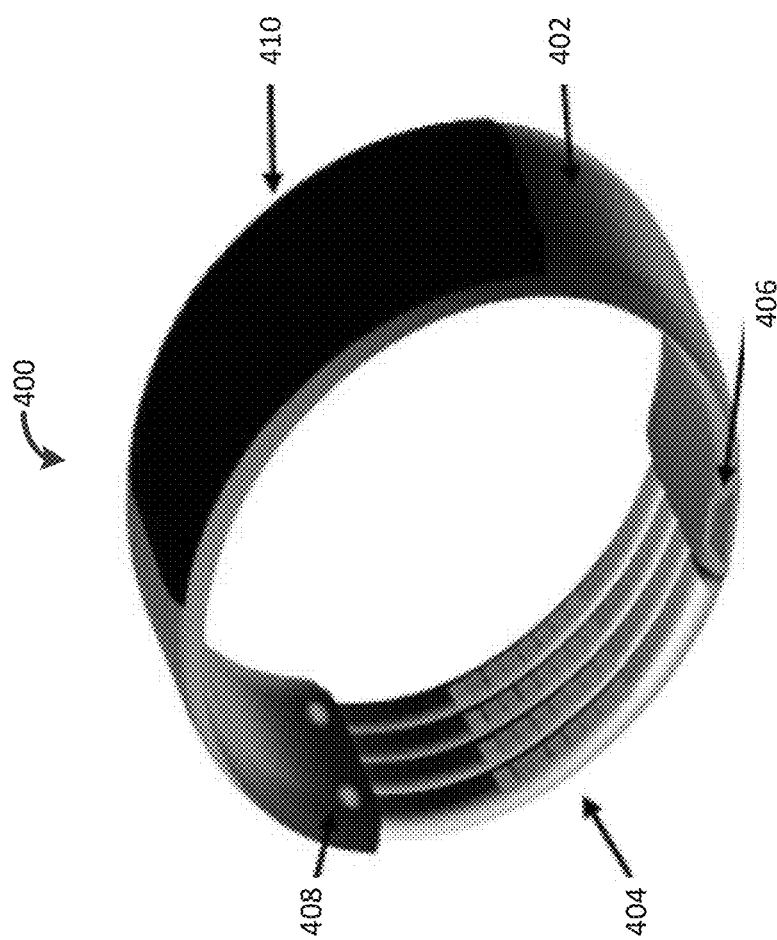
FIG. 4 illustrates an exemplary apparatus for measuring various blood metrics in accordance with an embodiment of the present application.

FIG. 4 illustrates an exemplary apparatus 400 for measuring various blood metrics in accordance with an embodiment of the present application. The apparatus 400 comprises a central unit 402, a sensor array 404, and a coupling means 408. The central unit 402 may be a wearable member made of elastic and/or flexible hypoallergenic wearable material.

In the illustrated example, the sensor array 404 is coupled to the central unit 402. The sensor array 404 may comprise any number of energy transmitters and/or energy receivers. The sensor array 404 may be detached from the central unit 402. In some embodiments, the sensor array 404 may be mechanically and electrically coupled to the central unit 402. The sensor array 404 comprises various illumination (e.g., near infra-red, infra-red, or short infra-red) and sensing array. The sensor array 404 may further comprise conductivity and/or capacity sensors. Different sensor array 404 may be provided to measure different blood metrics.

The central unit 402 may comprise an analyzer. In some embodiments, the central unit comprises an analyzer, one or more energy transmitter(s), and one or more energy receiver (s). The central unit 402 may further comprise a communication module and/or a battery compartment. The coupling means 408 are mounting screw holes in FIG. 4, however, it will be appreciated that coupling means may be optional. Further, coupling means 408 may include any kind of means including a clip, hook, switch, expanding fabric, adhesive, or the like. One of ordinary skill in the art would understand that other mounting means may be used.

The apparatus 400 further comprises a micro-USB port 406 to allow for communication with a digital device and a screen 410. Various user interfaces (e.g., lights, a display, touchscreen, or the like) may be displayed on the screen 410.

In some embodiments, the apparatus 400 may be or include the blood metrics measurement apparatus 200 described with regard to FIG. 2, or the blood metrics measurement apparatus 102 described with regard to FIG. 1.

Figure 5:
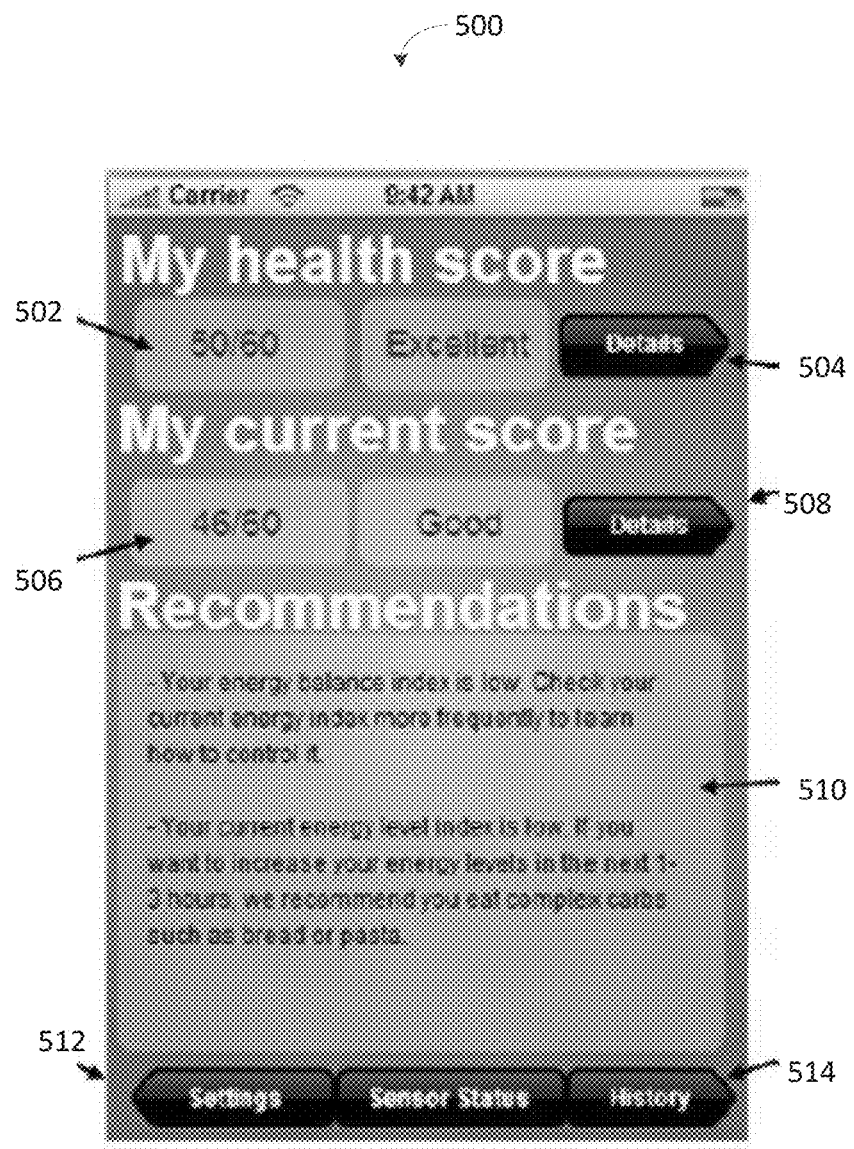
FIG. 5 illustrates a display of an assessment of a current health index derived from data collected from or with a multispectral blood metrics measurement apparatus in various embodiments.
Figure 6:
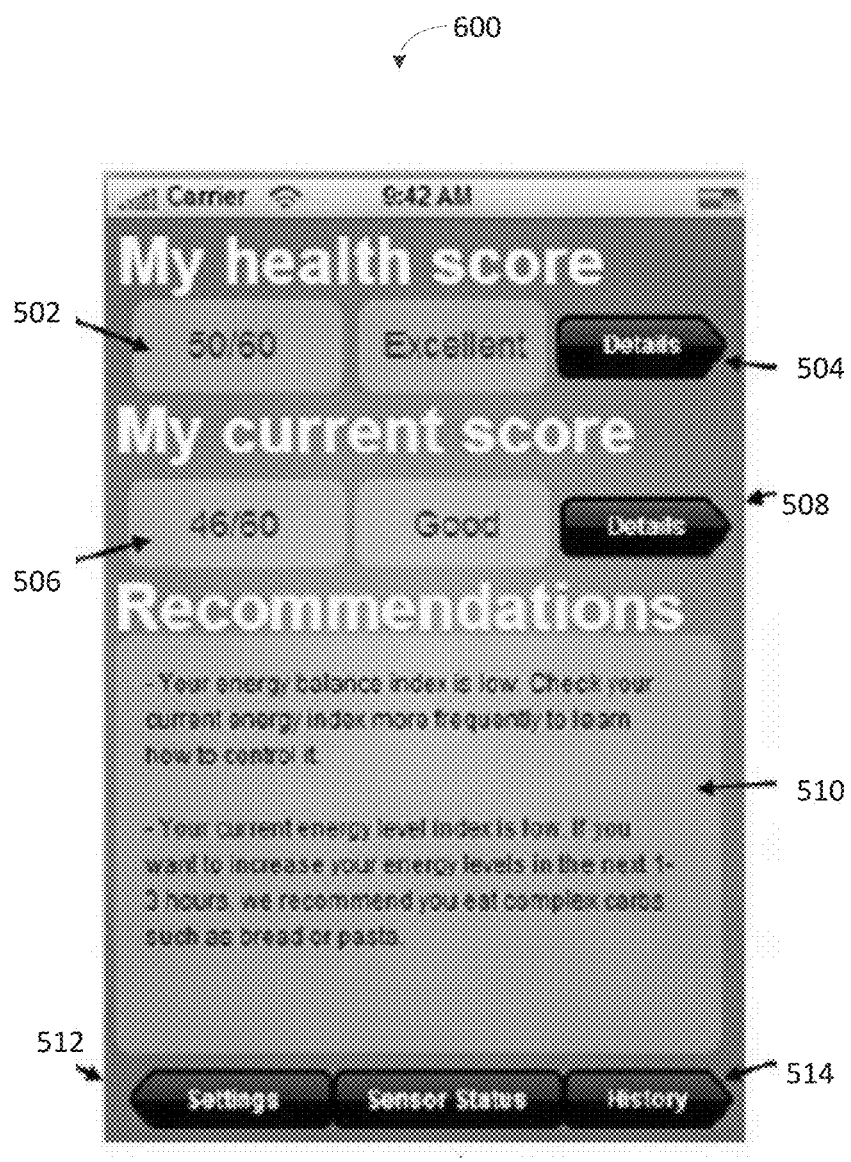
FIG. 6 illustrates a display of an assessment of an overall health index, derived from data collected from or with a multispectral blood metrics measurement apparatus in various embodiments.
Figure 7:
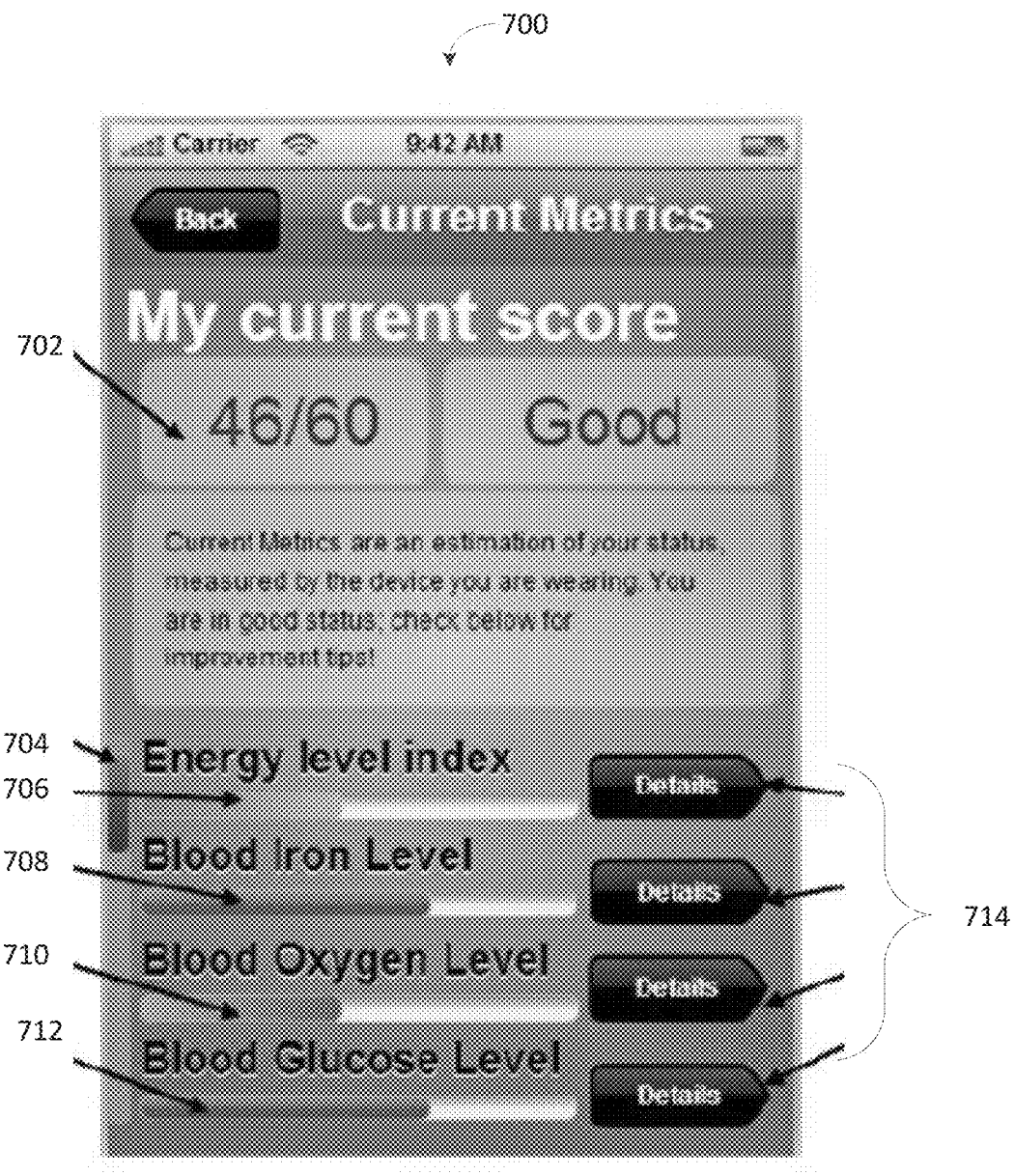
FIG. 7 illustrates a display of an assessment of an overall health index, derived from data collected from or with a multispectral blood metrics measurement apparatus in various embodiments.

FIGS. 5-7 are screenshots illustrating an example of presenting health analysis over a user interface in accordance with various embodiments. Various embodiments may store blood metrics and/or nutrient measurements. FIG. 5 illustrates a display 500 of an assessment of a current health index derived from data collected from or with a multispectral blood metrics measurement apparatus in various embodiments. The display may appear on the user's smartphone, for example. In various embodiments, the analyzer 202 or any digital device may analyze measurements collected over time to generate a health score that can be compared to a health threshold to provide qualitative and/or quantitative scoring. Similarly, the analyzer 202 or any digital device may analyze measurements recently collected to generate a current score that can be compared to a current health threshold to provide qualitative and/or quantitative scoring.

In some embodiments, a user interface may display a health score 502, an option for details regarding the health score 504, a current score 506, an option for details regarding the current score 508, a recommendation 510, a settings option 512, and a history of measurements 514. Options for details 504 and 506 may describe the metrics as well as the values of the metrics that went into the health score 504 and the current score 506, respectively.

In some embodiments, there is a recommendation engine configured to retrieve recommendations 510 based on the health score 504 and/or the current score 506. The settings option 512 may allow the user to configure metrics to be tracked and set alerts. In some embodiments, the user may utilize the settings options 512 to secure the information (e.g., encrypt the information and/or set passwords). The history of measurements option 514 may provide logged metrics and analysis information over time (e.g., as a chart).

It will be appreciated that the multispectral blood metrics measurement apparatus 200 and/or any digital device may generate reports based on the analysis, the metrics (e.g., blood metrics or metrics based on nutrients), historic measurements, historic analysis, or any other information. Further, alerts may be set by the multispectral blood metrics measurement apparatus 200 and/or any digital device.

It will be appreciated that the multispectral blood metrics measurement apparatus 200 may be taking many measurements over time (e.g., many measurements every minute) and may track health and changes in metrics over time and/or in the short term. In some embodiments, if a condition is of sufficient seriousness (e.g., heart rate shows erratic beats), the multispectral blood metrics measurement apparatus 200 or any digital device may provide an alert and request assistance (e.g., from emergency personnel via the communication network).

Various health and wellness predictors such as, but not limited to, energy level, blood iron level, blood oxygen level, and blood glucose level are displayed. FIG. 6 illustrates a display 600 of an assessment of an overall health index, derived from data collected from or with a multispectral blood metrics measurement apparatus in various embodiments.

In some embodiments, a user interface may display a current score 602, energy balance information 606, sleep quality information 608, blood metrics information 610, and body composition information 612 as well as other information accessible by slider 604. Additional details may be available through buttons 614. It will be appreciated that any amount of information may be provided. In some embodiments, the display 600 summarizes information while more detailed information recommendations, measurement data, analysis information, and the like may be available through the details buttons 614 or in other screens.

Recommendations to the user based on the current and previous measurements are provided. FIG. 7 illustrates a display 700 of an assessment of an overall health index, derived from data collected from or with a multispectral blood metrics measurement apparatus in various embodiments. In some embodiments, a user interface may display a current score 702, energy level information 706, blood iron level information 708, blood oxygen level information 710, and blood glucose level 712 as well as other information accessible by slider 704. Additional details may be available through buttons 714. It will be appreciated that any amount of information may be provided. In some embodiments, the display 700 summarizes information while more detailed information recommendations, measurement data, analysis information, and the like may be available through the details buttons 714 or in other screens.

Various embodiments track and analyze blood metrics. Health recommendations may be based on instantaneous blood metrics measurements and history blood metrics measurement. In addition, blood metrics and health condition of a user may be compared to health data of the general public. For example, a user's health condition may be compared to health condition of other similar users such as users of the same gender and age group, users of the same profession, friends of a user, etc.

Figure 8:
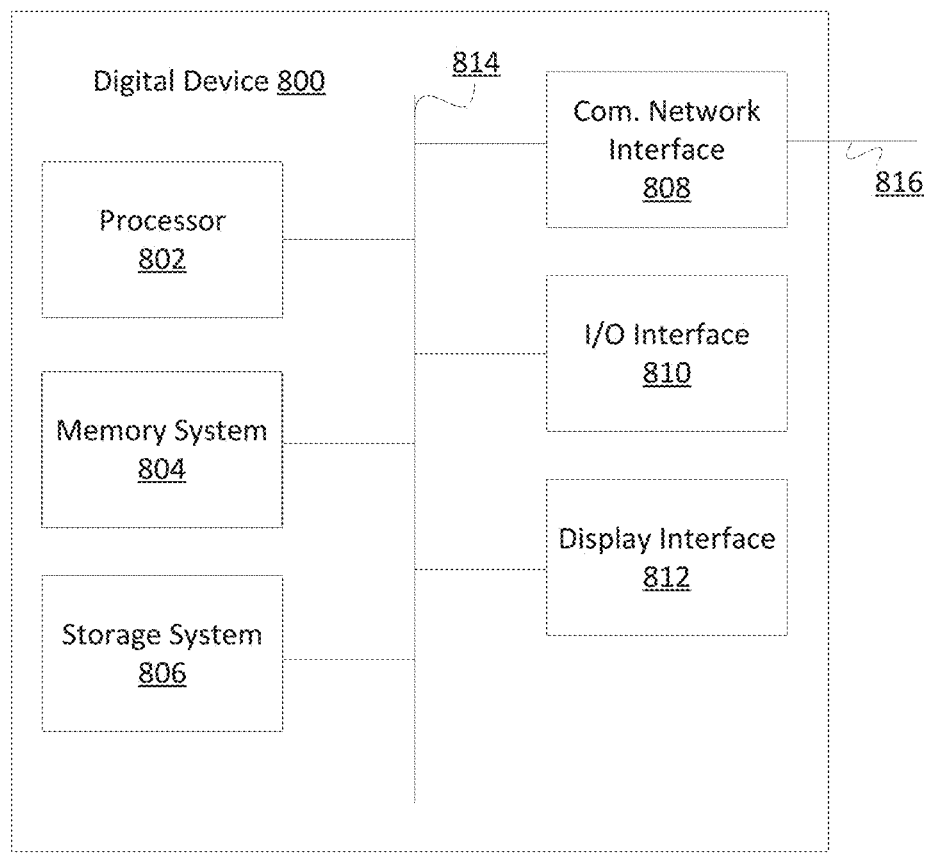
FIG. 8 is a block diagram illustrating an exemplary digital device that can be utilized in the implementation of various embodiments.

FIG. 8 is a block diagram of an exemplary digital device 800. The digital device 800 comprises a processor 802, a memory system 804, a storage system 806, a communication network interface 808, an I/O interface 810, and a display interface 812 communicatively coupled to a bus 814. The processor 802 is configured to execute executable instructions (e.g., programs). In some embodiments, the processor 802 comprises circuitry or any processor capable of processing the executable instructions.

The memory system 804 is any memory configured to store data. Some examples of the memory system 804 are storage devices, such as RAM or ROM. The memory system 804 can comprise the RAM cache. In various embodiments, data is stored within the memory system 804. The data within the memory system 804 may be cleared or ultimately transferred to the storage system 806.

The storage system 806 is any storage configured to retrieve and store data. Some examples of the storage system 806 are flash drives, hard drives, optical drives, and/or magnetic tape. In some embodiments, the digital device 800 includes a memory system 804 in the form of RAM and a storage system 806 in the form of flash data. Both the memory system 804 and the storage system 806 comprise computer readable media which may store instructions or programs that are executable by a computer processor including the processor 802.

The communications network interface (com.network interface) 808 can be coupled to a network (e.g., the computer network 104) via the link 816. The communication network interface 808 may support communication over an Ethernet connection, a serial connection, a parallel connection, or an ATA connection, for example. The communication network interface 808 may also support wireless communication (e.g., 802.11 a/b/g/n, WiMax). It will be appreciated that the communication network interface 808 can support many wired and wireless standards.

The optional input/output (I/O) interface 810 is any device that receives input from the user and output data. The optional display interface 812 is any device that is configured to output graphics and data to a display. In one example, the display interface 812 is a graphics adapter.

It will be appreciated that the hardware elements of the digital device 800 are not limited to those depicted in FIG. 8. A digital device 800 may comprise more or less hardware elements than those depicted. Further, hardware elements may share functionality and still be within various embodiments described herein. In one example, encoding and/or decoding may be performed by the processor 802 and/or a co-processor located on a GPU (i.e., Nvidia®).

Respiratory Rate Analysis

In various embodiments, respiratory rate (RR) may be measured along with other vital signs, such as heart rate, blood pressure, and body temperature. Respiratory rate may be an indicator of the performance of the various systems of the body, and may be a predictor of adverse events, such as cardiac arrest or sleep apnea. Unfortunately, the level of recordation of vital signs, especially respiration rate, in many environments (e.g., hospitals) may be poor or even non-existent.

Respiratory rate may be measured as the number of breaths per minute (BPM), and may typically be between 10-30 BPM in adults, although rates greater than 24 BPM, or other threshold level, may be an indicator of illness or adverse health event. In clinical settings, respiratory rate is typically measured using a capnometer that measures an amount of carbon dioxide passing through a tube inserted in to a user's body. Use of capnometers, however, may be invasive, uncomfortable, and otherwise unsuited for non-invasive continuous respiratory rate measurement.

Continuously measuring respiration rate, and tracking rate changes may help, for example, to identify or predict illness or other health event. Systems and methods are described herein that may provide non-invasive continuous respiratory rate measurement. Respiratory rate measurements, in some embodiments, may be calculated or estimated when a user is engaged in complex tasks, such as walking, running, working at a desk, carrying objects, and the like.

Multichannel signals may be obtained from a wearable device to accurately calculate respiration rate. A wearable device may be worn on the wrist or other part of the body. Signals acquired from the wrist, however, may be noisy. For example, high frequency noise may be associated with quantization, transmission line interference, and the like. High frequency noise (or, artifacts) may be removed or attenuated by applying low-pass filtering. In addition to, or instead of, high frequency noise, the signal received from a user's body may include low frequency (or, DC level) noise that may change depending on ambient light, skin type, or other factors. In some embodiments, the low frequency noise may be eliminated using high pass filters. Different filter parameters may be more effective than other filter parameters when calculating respiratory rate, and a respiratory rate classifier may be used to determine appropriate filter parameters.

Motion may add motion noise in the signal. For example, motion may introduce artifacts that may not be removed or attenuated using low pass and high pass filters. In some embodiments, spectrum extraction (or, estimation), as described further herein, may be used to remove or attenuate noise (e.g., motion related noise). In some embodiments, temporal filtering may be used to further reduce, remove, or attenuate signal noise.

In various embodiments, a blood metrics measurement apparatus may generate multichannel signals (e.g., PPG signals or pressure signals) which may be provided to a respiratory rate calculation system to calculate respiratory rate values (e.g., breaths per minute or "BPM"). The blood metrics measurement apparatus includes a pressure sensor for measuring pressure signals. The respiratory rate calculation system may pre-process (or, "filter") the multichannel signals (e.g., to remove noise from the signals), select (or, "extract") wave features from signal waves, and generate feature vectors based on the selected wave features. A respiratory rate classifier may be used to facilitate pre-processing of the multichannel signals.

In some embodiments, functionality of the systems and modules described herein may be performed similarly with respect to both optical signals (e.g., PPG signals) and non-optical signals (e.g., pressure signals). Accordingly, it will be appreciated that signals, as used herein, may include optical signals, non-optical signals, or both. Similarly, signals can include multichannel signals, as well as single channel signals.

Figure 9:
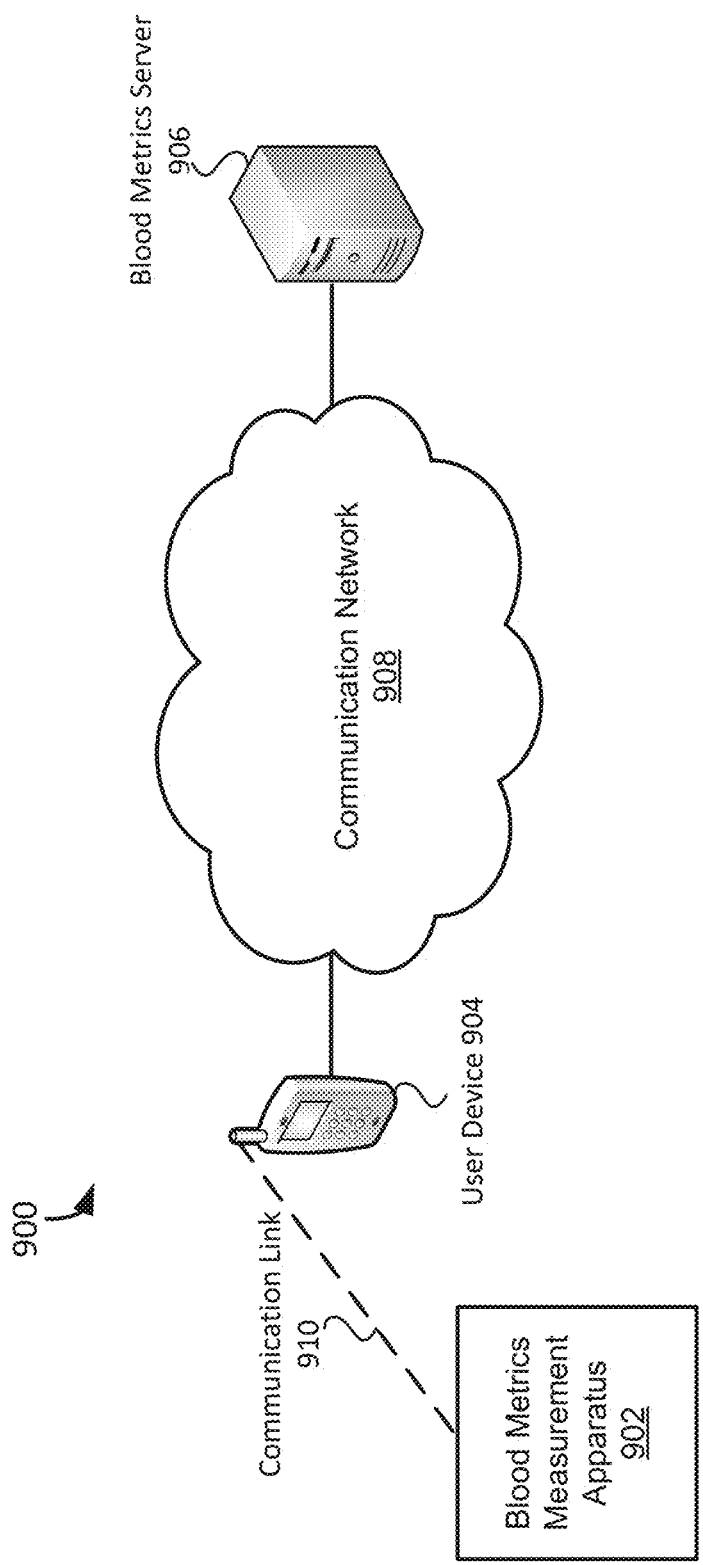
FIG. 9 depicts a block diagram of a system and environment for non-invasive respiratory rate measurement according to some embodiments.

FIG. 9 depicts a block diagram of a system and environment 900 for non-invasive respiratory rate measurement according to some embodiments. In some embodiments, the system and environment 900 includes a blood metrics measurement apparatus 902, a user device 904, a blood metrics server 906, a communication network 908, and a communication link 910.

The blood metrics measurement apparatus 902 may be configured to facilitate non-invasive measurement of a user's respiratory rate. In some embodiments, more particularly, the blood metrics measurement apparatus 902 facilitates non-invasive continuous measurement of a user's respiratory rate measurement. It will be appreciated that non-invasive continuous measurement may include measuring respiratory rate measurement in real-time without interruption and without inserting a device (e.g., a breathing tube) into to the user's body.

The blood metrics measurement apparatus 902 may project energy into tissue of a user (e.g., the wearer of the apparatus 902) and detect (or, "receive") energy reflected from and/or transmitted through tissue of the user. In some embodiments, the blood metrics measurement apparatus 902 may project energy at one or more wavelengths (e.g., 523 nm, 590 nm, 623 nm, 660 nm, 740 nm, 850 nm, 940 nm, etc.) from multiple light sources (e.g., light-emitting diodes). The detected energy may be a fraction (or, "portion") of the energy that is projected into the tissue. Energy at different wavelengths may be absorbed at a different rate that is related to a user's body state. The user's body state (e.g., respiratory rate measurement, heart rate, or the like) may determine the amount of absorbed energy. Accordingly, energy at different wavelengths may be absorbed at different levels by a user's body. The fraction of energy received (e.g., that is reflected by the tissue or transmitted through the tissue) may be used to generate signals, such as photoplethysmogram (or, "PPG") signals, at different levels. These signals may provide information of the user's body state. This information may be obtained by analyzing waveforms of the signal in a time domain and/or a frequency domain.

A user may comfortably wear the blood metrics measurement apparatus 902 over time. For example, the blood metrics measurement apparatus 902 may be worn without interrupting typical user activity (e.g., moving, walking, running, sleeping, etc.). The blood metrics measurement apparatus 902 may comprise lightweight components. The blood metrics measurement apparatus 902 may be made of hypoallergenic materials. The blood metrics measurement apparatus 902 may be flexibly built so that it may fit various body parts (e.g., wrist, earlobe, ankle, or chest) of a user. In some embodiments, the blood metrics measurement apparatus 902 may include some or all of the functionality of the user device 904. Alternately, the user device may include some or all of the functionality of the measurement apparatus 902.

In some embodiments, the blood metrics measurement apparatus 902 may be or include the apparatus 400 described with regard to FIG. 4, the blood metrics measurement apparatus 200 depicted with regard to FIG. 2, or the blood metrics measurement apparatus 102 described with regard to FIG. 1.

The user device 904 may include any digital device (e.g., mobile device) capable of executing an application related to measuring blood metrics, such as: calculating a respiratory rate measurement, presenting a user interface through a display, and/or communicating with various entities (e.g. communicating with entities over the communication network 908). For example, through the communication link 910, the user device 902 may receive one or more blood metric measurements (e.g., one or more signals) from the blood metrics measurement apparatus 902, track and store the blood metric measurements, analyze the blood metric measurements, and/or provide recommendations and/or messages based on the blood metric measurements. An application user interface may facilitate interaction between a user of the user device 904 and an application running on the user device 904. The user device 904 may be, include, or be a part of the user system 104 described with regard to FIG. 1.

In various embodiments, the user device 904 may perform analysis of measurements received from the blood metrics measurement apparatus 902 (e.g., calculate respiratory rate measurement values), display results, provide reports, display progress, display historic readings, track measurements, track analysis, provide alerts (or, messages), and/or the like.

The blood metrics server 906 may be configured to generate and/or store respiratory rate classifiers. For example, the blood metrics server 906 may comprise one or more server computers, desktop computers, mobile devices, and/or other digital device(s) which generate and/or store respiratory rate classifiers. In some embodiments, the blood metrics server 906 receives and processes user registration requests (e.g., user account registration requests, blood metrics measurement apparatus registration requests), provides respiratory rate classifiers to the user device 902 via the communication network 908, and/or the like.

Computing devices (e.g., digital devices) may include a mobile phone, a tablet computing device, a laptop, a desktop computer, personal digital assistant, a thin client, or any other type of network accessible user device known to those of skill in the art. Further, the blood metrics server 906 may comprise of one or more servers, which may be operating on or implemented using one or more cloud-based services (e.g., System-as-a-Service [SaaS], Platform-as-a-Service [PaaS], or Infrastructure-as-a-Service [IaaS]).

Each of the blood metrics measurement apparatus 902, the user device 904, and the blood metrics server 906 may be implemented using one or more digital devices. An example digital device is described in FIG. 8.

In some embodiments, the communication network 908 represents one or more communication network(s). The communication network 908 may provide communication between the blood metrics measurement apparatus 902, the user device 904, and/or the blood metrics server 906. In some examples, the communication network 908 comprises digital devices, routers, cables, and/or other network topology. In other examples, the communication network 908 may be wireless and/or wireless. In some embodiments, the communication network 908 may be another type of network, such as the Internet, that may be public, private, IP-based, non-IP based, and so forth.

In some embodiments, the communication link 910 represents one or more communication network connections. The communication link 910 may provide communication between the blood metrics measurement apparatus 902 and the user device 904. In some examples, the communication link 910 comprises a network connection of the communication network 908, and/or a separate communication network. In some embodiments, the communication link 910 comprises a wireless communication link, such as a Bluetooth communication link, Wi-Fi communication link, and/or the like.

Figure 10:
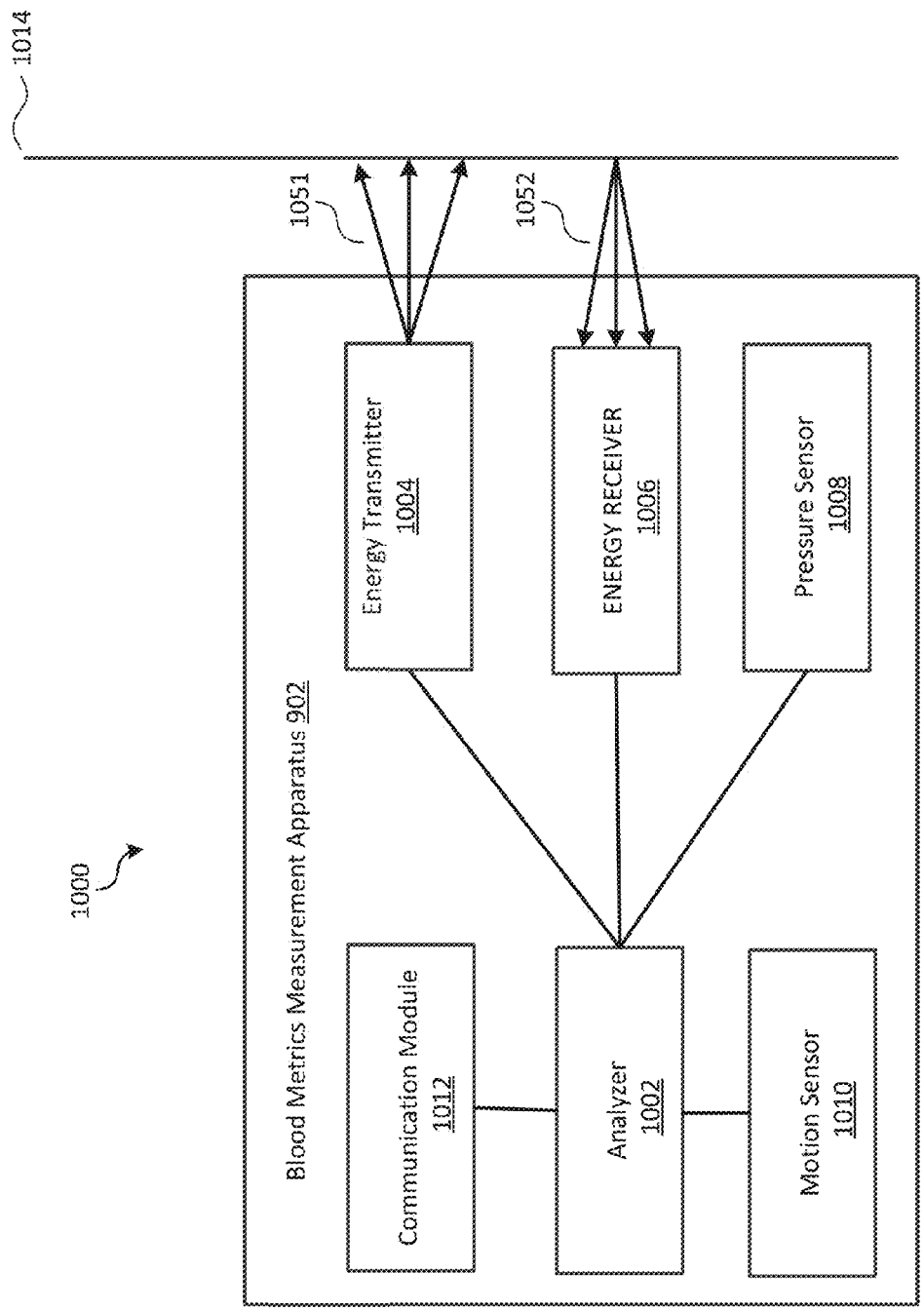
FIG. 10 depicts a block diagram of a blood metrics measurement apparatus 902 according to some embodiments.

FIG. 10 depicts a block diagram 1000 of a blood metrics measurement apparatus 902 according to some embodiments. The blood metrics measurement apparatus 902 comprises an analyzer 1002, an energy transmitter 1004, an energy receiver 1006, a pressure sensor 1008, a motion sensor 1010, and a communication module 1012. The blood metrics measurement apparatus 902 may be, include, or be a part of a wearable member. The wearable member may include, for example, a bracelet, glasses, necklace, ring, anklet, belt, broach, jewelry, clothing, or any other member of combination of members that allow the blood metrics measurement apparatus 902 to be close to or touch a body of the wearer. In some embodiments, the blood metrics measurement apparatus 902 may further comprise a driver (not shown) and a power source (not shown). The power source may be coupled to the energy transmitter 1004 via the driver. The blood metrics measurement apparatus 902 may also comprise an Analog-to-Digital Converter ("ADC") (not shown). In one example, the ADC may be coupled to the energy receiver 1006 and the analyzer 202.

The analyzer 1002 may be coupled to the energy transmitter 1004, the energy receiver 1006, the pressure sensor 1008, the motion sensor 1010, and the communication module 1012. The energy transmitter 1004 and the energy receiver 1006 may be secured to the wearable member such that the energy transmitter 1004 and the energy receiver 1006 may make contact or be in proximity with tissues (e.g., skin) of a user.

In various embodiments, the energy transmitter 1004 emits energy including, but not limited to, light, into the body of the user. The energy produced by the energy transmitter may be in the direction of entering tissues. For example, the energy produced by the energy transmitter 1004 is in a direction 1051 entering the tissue 1014. In some embodiments, the energy transmitter 1004 emits energy or light at different wavelengths. The energy transmitter 1004 may comprise any number of light emission diodes ("LEDs"). In some embodiments, the energy transmitter 1004 comprises at least two LEDs. Each LED may be configured to emit energy at one or more wavelengths. In another example, each LED may emit light with a peak wavelength centered around a wavelength. In one example, the energy transmitter 1004 may emit light with a peak wavelength centered around 500 nm to 1800 nm, although the wavelength may include a variety of spectrums (e.g., IR, near-IR, and the like).

Each wavelength may correspond to one or more blood metrics of interest and/or one or more nutrients. It will be appreciated that different components of the blood and/or different nutrients may absorb energy at different wavelengths. In various embodiments, a controller, driver, analyzer 1002, or the like may receive a blood metric or nutrient of interest (e.g., from a user of the blood metrics measurement apparatus 902 and/or a user device not shown). The controller, driver, analyzer 1002 or the like may associate the blood metric and/or nutrient of interest with one or more wavelengths and configure one or more of the LEDs to emit energy of at least one of the one or more wavelengths. For example, the analyzer 1002 may command the driver to deliver electric power to one LED that is configured to emit light at the desired wavelength.

The energy receiver 1006 may detect energy associated with the energy provided by the LEDs from tissues (e.g., skin) of the user. In this example, received and/or detected energy is in the direction 1052 that leaves from the tissue 1014. In various embodiments, the energy receiver 1006 may detect energy from the body of the user that is a fraction of the energy produced by the energy transmitter 1004.

The energy transmitter 1004 and the energy receiver 1006 may be configured such that the energy receiver 1006 detects reflected energy from tissues of the user of the multispectral blood metrics measurement apparatus 902. For example, the energy transmitter 1004 and the energy receiver 1006 may be configured to be disposed on one surface or side of a user's tissue. The energy transmitter 1004 and the energy receiver 1006 may be configured such that the energy receiver 1006 detects energy from the energy transmitter 1004 that passes through or reflects from the user's tissues. In some embodiments, the energy transmitter 1004 and the energy receiver 1006 may be configured to be disposed on different (e.g., opposite) surfaces or sides of a users' tissue.

The energy transmitter 1004 may be configured to generate energy at a set of wavelengths. In some embodiments, the energy transmitter 1004 generates energy at different wavelengths sequentially and/or periodically. For example, the energy transmitter 1004 may be configured to generate energy at each particular wavelength until energy at all wavelengths of the set is generated. The period of time for the energy transmitter 1004 to generate energy at all wavelengths of the set is a generation period. Subsequent to completion of the generation period, the energy transmitter 1004 may start a new generation period thereby allowing multiple measurements.

Energy detected from tissues of a user may be detected by the energy receiver 1006. The energy receiver 1006 may be configured to generate a signal in response to the detected energy. In some embodiments, the energy receiver 1006 may be triggered by the energy received to generate an output which may be dependent or partially dependent upon the amount of energy received. The energy receiver 1006 may be configured to generate a signal (e.g., an electric current, or an electric voltage) in response to the energy received from the tissues.

The signal generated by the energy receiver 1006 may be associated with one or more blood metrics and/or nutrients of interest. Energy at different wavelengths may be absorbed at a different rate that is related to a user's body state. The user's body state (e.g., heart rate, blood pressure, nutrient level, or the like) may determine the amount of energy absorbed by the body. Accordingly, energy from the user's body at different wavelengths may be detected at different levels thereby causing different responses of the energy receiver 1006. The energy receiver 1006 may, for example, output signals based on the level of the energy received.

The energy receiver 1006 may provide information associated with the user's body state. Blood metric information may be determined (e.g., by the analyzer 1002) from the output signal of the energy receiver 1006. In some embodiments, the energy receiver 1006 may comprise a set of photodetectors (e.g., a photo diode, or a photo transistor) which are configured to output a signal dependent upon photons or the like from the energy transmitter 1004 that passed through tissues of the user.

In various embodiments, the output signal of the energy receiver 1006 is a composite of multiple signals. Each signal of the composite may be associated with energy at a wavelength which may be a portion (or fraction) of the total energy emitted by the energy transmitter 1004.

The pressure sensor 1008 may be configured to generate, detect, and/or measure non-optical signals. For example, the pressure sensor 1008 may non-invasively and continuously generate, detect, and/or measure pressure pulse signals.

In some embodiments, the motion sensor 1010 may be configured to detect position and orientation of the blood metrics measurement apparatus 902, and detect motion of the blood metrics measurement apparatus 902. For example, the blood metrics measurement apparatus 902 may detect position, orientation, and motion along an x, y, or z-axis, and measured values may include velocity, acceleration, distance, and the like. In some embodiments, the motion sensor 1010 may include one or more accelerometers, gyroscope, global positioning systems, or the like. The motion sensor may be coupled to the analyzer 1002.

The communication module 1012 may be configured to send requests to and receive data from one or a plurality of systems. The communication module 1012 may send requests to and receive data from a systems through a network or a portion of a network. Depending upon implementation-specific or other considerations, the communication module 1012 may send requests and receive data through a connection (e.g., the communication link 910), all or a portion of which may be a wireless connection. The communication module 1012 may request and receive messages, and/or other communications from associated systems.

It will be appreciated that the analyzer 1002 may be or include a part of analyzer 202 described with regard to FIG. 2 or the central unit 402 described with regard to FIG. 4. The energy transmitter 1004 may be or include a part of energy transmitter 204 described with regard to FIG. 2 or the central unit 402 described with regard to FIG. 4. The energy receiver 1006 may be or include energy receiver 206 described with regard to FIG. 2 or the central unit 402 described with regard to FIG. 4.

Figure 11:
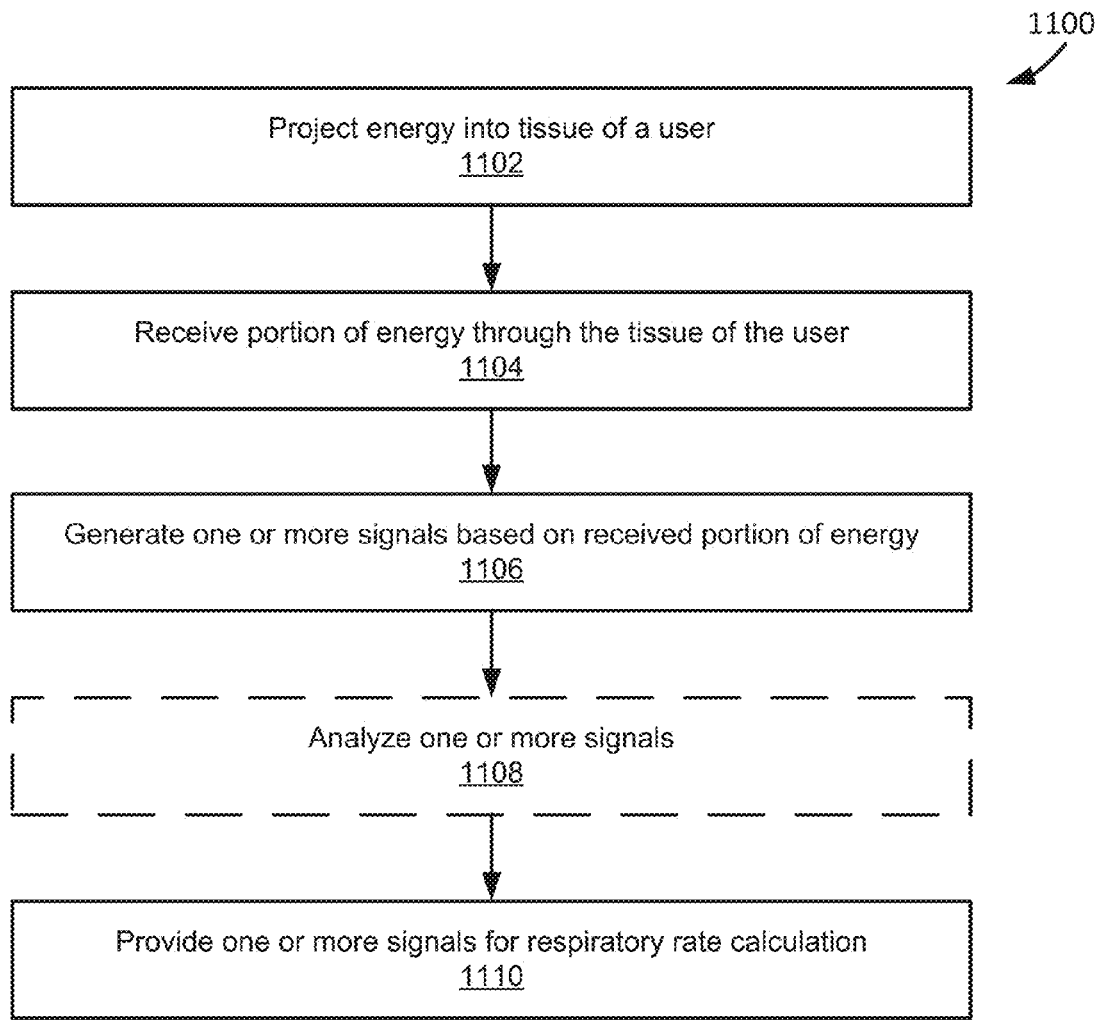
FIG. 11 depicts a flowchart of an example method of operation of a blood metrics measurement apparatus according to some embodiments.

FIG. 11 depicts a flowchart 1100 of an example method of operation of a blood metrics measurement apparatus (e.g., blood metrics measurement apparatus 902) according to some embodiments. In this and other flowcharts described herein, the flowchart illustrates by way of example a sequence of steps. It should be understood the steps may be reorganized for parallel execution, or reordered, as applicable. Moreover, some steps that could have been included may have been removed to avoid providing too much information for the sake of clarity and some steps that were included could be removed, but may have been included for the sake of illustrative clarity.

In step 1102, a blood metrics measurement apparatus projects energy into tissue of a user (e.g., the user wearing blood metrics measurement apparatus). The energy may be projected from an energy transmitter (e.g., energy transmitter 1004) comprising a plurality of light sources (e.g., LEDs). In some embodiments, a first light source (e.g., one or more LEDs) may project light energy at a plurality of different wavelengths, such as 523 nm, 590 nm, 623 nm, 660 nm, 740 nm, 850 nm, and 940 nm, and a second light source (e.g., one or more LEDs) may project energy at the same, or substantially similar, wavelength as one of the wavelengths projected by the first light source (e.g., 523 nm, 590 nm, 623 nm, 660 nm, 740 nm, 850 nm, or 940 nm). It will be appreciated that other configuration may be used (e.g., a greater number of light sources) a greater or lesser number of wavelengths projected from the lights sources, and so forth.

In step 1104, the blood metrics measurement apparatus receives (or, "detects) portions of energy through the tissue of the user. In some embodiments, an energy receiver (e.g., energy receiver 1006) detects a portion of the energy transmitted into the user's tissue by the energy transmitter. The energy receiver may generate a signal based on the portion of energy detected (e.g., based on the amount of the energy detected). For example, energy detected may be a portion of the energy projected at step 1102 reflected by the tissue. By way of further example, energy detected may be a portion of the energy projected at step 1102 that passes through the tissue (e.g., other undetected energy may be absorbed by tissue and/or otherwise blocked). In various embodiments, steps 1102 and 1104 are performed simultaneously or substantially simultaneously. That is, energy projection and detection may be performed approximately simultaneously.

In step 1106, the blood metrics measurement apparatus generates one or more signals based on the received portions of energy. In some embodiments, the energy receiver may generate a multichannel PPG signal (e.g., as mentioned above). The output (or, "generated") signal of the energy receiver may be an electric current or an electric voltage, of which the amplitude may be related to the amount of the energy detected.

In various embodiments, analysis of the signals from the energy receiver may identify abnormal measurements. For example, each of the measurements may be compared to a predetermined value. If the difference between the measurement and the predetermined value is above (or below) a threshold, then the measurement may be determined to be abnormal. An abnormal value may trigger additional analysis or an alert. In some embodiments, an abnormal value is ignored (e.g., as possibly effected by noise caused by movement of the energy transmitter and/or the energy receiver). In various embodiments, the abnormal value may be discounted (e.g., the weight of the value reduced). The degree of discount may be based, for example, on information from an accelerometer (e.g., a large acceleration may indicate that the abnormal value should be significantly discounted) and/or based on historical values. It will be appreciated that the degree of discount may be based on any number of factors.

In some embodiments, measurements may be averaged over a period of time. A Kalman filer (e.g., a nonlinear, unscented Kalman filter) may be applied to any number of measurements or averaged measurements. A motion measurement (e.g., a measurement by an accelerometer) may be considered. Upon determining a measurement is abnormal, the motion measurement for that time point may be inspected. A large measurement may indicate large vibrations or accelerations that corroborate that the measurement may be abnormal. Measurements collected in such situations are likely to have significant electrical noises.

At step 1108, the blood metrics measurement apparatus (e.g., blood metrics measurement apparatus 902) analyzes signals from the energy receiver analyzed in the frequency domain to determine blood metrics. Concentration of a nutrient in the blood may subsequently be determined. In some embodiments, signals may be provided to a bandpass filter that separates AC components from DC components. An AC component may represent signal variation at the cardiac frequency and a DC component may represent the average overall transmitted light intensity. In some embodiments, a heart rate and/or oxygen saturation, $SpO_2$ may be determined. The heart rate may be determined, for example, by averaging the maximum frequency to determine the rate of cardiac beats in a predetermined amount of time. The oxygen saturation $SpO_2$ may be determined according to Equation (1):

$$SpO_2 = 110 - 25 \times R \qquad (1),$$

where R is the ration of a red and infrared normalized transmitted light intensity. R may be determined according to Equation (2):

$$R = \frac{AC_R / DC_R}{AC_{IR} / DC_{IR}}, \qquad (2),$$

where the $AC_R$ is the AC component of the detected energy corresponding to a wavelength (e.g., red light), $DC_R$ is the DC component of the detected energy corresponding to the wavelength (e.g., red light), $AC_{IR}$ is the AC component of the detected energy corresponding to a different wavelength (e.g., infrared light), and $DC_{IR}$ is the DC component of the detected energy corresponding to the different wavelength (e.g., infrared light). In some embodiments, the AC component may be selected as the highest spectral line in the cardiac frequency band. Waveform analysis may be performed to determine the R-R interval defined by two successive AC components, an elapsed interval and the probation, if there is any.

It will be appreciated that analysis may be performed by the analyzer and/or any other digital device (e.g., user device or a blood metrics server such as a blood metrics server 906).

State space estimation and progression may be performed to determine blood metrics. A system may be modeled according to Equation (3):

$$x(n+1) = f[x(n)] + u(n)$$

$$y(n) = h[x(n)] + v(n) \qquad (3),$$

where x(n) represents the state of the system, u(n) is process noise, y(n) is the vector of the observed signals, and v(n) is the measurement noise.

Table 1 lists one or more parameters for x(n) as well as their initial value in some embodiments:

TABLE 1

| Parameter | Symbol | Initial Value |
|---|---|---|
| Cardiac frequency | $f_{HR}$ | 1 Hz |
| Cardiac phase | $\theta_{HR}$ | 0 |
| Cardiac harmonic amplitude | $1_{Harmonic}^{HR}$ | 0 |
| Cardiac Pulse Pressure | $P_{HR}$ | 1 |
| Point Blood Pressure | $P_{Point}$ | 1 |

TABLE 1-continued

| Parameter | Symbol | Initial Value |
|---|---|---|
| Respiratory frequency | $f_{Resp}$ | 0.3 Hz |
| Respiratory phase | $\theta_{Resp}$ | 0 |
| Wavelength i = 1 ... N AC peak amplitude | $I_{\lambda_i}^{AC}$ | 0.5 max_value |
| Wavelength i = 1 ... N AC peak location | $pos_{\lambda_i}^{AC}$ | Corresponding FFT bin to 1 Hz |
| Wavelength i = 1 ... N DC | $I_{\lambda_i}^{DC}$ | 0.5 max_value |
| Wavelength i = 1 ... N p2p amplitude | $I_{\lambda_i}^{p2p}$ | 1 ADC read |
| Wavelength i = 1 ... N rise time | $\tau_{\lambda_i}^{rise}$ | 0.1 sec |
| Wavelength i = 1 ... N Significance coefficient | $c_{\lambda_i}$ | 1 |
| Wavelength i = 1 ... N HRV | $T_{\lambda_i}^{HRV}$ | 1 sec |
| Best Ratio pH | $BR_{pH}$ | 2 |
| Best Ratio pCO2 | $BR_{pCO2}$ | 3 |
| Best Ratio pHCO3- | $BR_{pHCO3^-}$ | 4 |
| Acceleration magnitude | $I_{move}$ | 0 |
| GPS velocity | $|v|_{GPS}$ | 0 |
| GPS altitude | $|alt|_{GPS}$ | 0 |
| GPS acceleration | $|a|_{GPS}$ | 0 |
| GPS incline | $|incline|_{GPS}$ | 0 |
| Restfulness | Rest | 0 |
| Hydration | Hyd | 0 |
| Systolic Blood Pressure | SBP | 120 mmHg |
| Diastolic Blood Pressure | DBP | 80 mmHg |
| End tidal CO2 | ETCO2 | 40 mmHg |
| Blood Carbon Monoxide | SpCO | 0% |

Table 2 lists one or more parameters for y(n) as well as their initial value in some embodiments:

TABLE 2

| Parameter | Symbol | Initial |
|---|---|---|
| Blood pH | pH | 7.35 |
| Blood PCO2 | $pCO_2$ | 24 mmol |
| Blood PO2 | $pO_2$ | 24 mmol |
| Blood PHCO3- | $pHCO_3^-$ | 24 mmol |
| Blood Glucose | $pC_6H_{12}O_6$ | 3 mmol |
| Cardiac Frequency | $f_{HR}$ | 1 |
| Point Blood Pressure | $P_{Point}$ | 1 |
| Respiratory Frequency | $f_{Resp}$ | 0.3 |
| GPS velocity | $|v|_{GPS}$ | 0 |
| GPS altitude | $|alt|_{GPS}$ | 0 |
| GPS acceleration | $|a|_{GPS}$ | 0 |
| GPS incline | $|incline|_{GPS}$ | 0 |

Table 3 lists the state space model F(X(n)) between the parameters listed in Table 1 and Table 2 in some embodiments, where the energy wavelengths comprise 880 nm, 631 nm, 1450 nm, and 1550 nm:

TABLE 3

| Name | Symbol | Equation |
|---|---|---|
| Cardiac frequency | $f_{HR}$ | $bin\_to\_freq\left(\dfrac{\sum c_{\lambda_i} pos_{\lambda_i}^{AC}}{\sum c_{\lambda_i}}\right)$ |
| Cardiac phase | $\theta_{HR}$ | $\theta_{HR}(n-1) + f_s^{-1} * \omega^*$, where $\omega^* \in [\omega\_min, \omega\_max]$ |
| Cardiac harmonic amplitude | $I_{Harmonic}^{HR}$ | $\dfrac{\sum c_{\lambda_i} I_{\lambda_i}^{p2p}}{\sum c_{\lambda_i}}$ |
| Cardiac Pulse Pressure | $P_{HR}$ | $\left(\dfrac{\sum c_{\lambda_i} \tau_{\lambda_i}^{rise}}{\sum c_{\lambda_i}}\right)^{\wedge} - 1$ |
| Point Blood Pressure | $P_{Point}$ | $\tau_{\lambda_1}^{rise-1}$ |
| Respiratory frequency | $f_{Resp}$ | |

3) Respiratory and Heart Rate State Models: The fluctuations in the respiratory rate $\omega_r(n)$ and fluctuations in the heart rate $\omega_{ca}(n)$ that are not due to RSA are both modeled as a first-order autoregressive process with a mean and mild nonlinearity that limit the frequencies to know physiologic ranges $$\omega_r(n+1) = \bar{\omega}_r + \alpha_r\{s_r[\omega_r(n)] - \bar{\omega}_{cr}\} + u_{\omega_r}(n) \quad (15)$$

$$\omega_{ca}(n+1) = \bar{\omega}_c + \alpha_c\{s_c[\omega_{ca}(n)] - \bar{\omega}_r\} + u_{\omega_{ca}}(n) \quad (16)$$

where $\bar{\omega}_r$ and $\bar{\omega}_c$ are the a priori estimates of the expected respiratory and cardiac frequences, respectively; $\alpha_r$ and $\alpha_c$ control the bandwidth of the frequency fluctuations; and $u_{\omega_r}(n)$ and $u_{\omega_{ca}}(n)$ are white noise processes that model the random variation in the respiratory and cardiac frequencies, respectively.

The instantaneous respiratory and heart rates in units of Hz are then $$f_r(n) = \frac{1}{2\pi T_s} s_r[\omega_r(n)] \quad (17)$$

$$f_c(n) = \frac{1}{2\pi T_s} s_c[\omega_c(n)]. \quad (18)$$

| Name | Symbol | Equation |
|---|---|---|
| Respiratory phase | $\theta_{Resp}$ | $\theta_{Resp}(n-1) + f_s^{-1} * \omega^*$, where $\omega^* \in [\omega\_min, \omega\_max]$ |
| $\lambda$ = 880 nm AC peak | $I_{\lambda_i}^{AC}$ | From FFT |
| $\lambda$ = 880 nm DC | $pos_{\lambda_i}^{AC}$ | From FFT |
| $\lambda$ = 880 nm p2p amplitude | $I_{\lambda_i}^{DC}$ | From Waveform analysis |
| $\lambda$ = 880 nm rise time | $I_{\lambda_i}^{p2p}$ | From Waveform analysis |
| $\lambda$ = 880 nm signal trend | $\tau_{\lambda_i}^{rise}$ | From Waveform analysis |
| $\lambda$ = 880 nm Significance coefficient | $c_{\lambda_i}$ | From Waveform analysis |
| $\lambda$ = 880 nm HRV | $T_{\lambda_i}^{HRV}$ | From Waveform analysis |
| $\lambda$ = 631 nm AC peak | $I_{\lambda_i}^{AC}$ | From Fast Fourier Transformation ("FFT") |
| $\lambda$ = 631 nm DC | $pos_{\lambda_i}^{AC}$ | From FFT |
| $\lambda$ = 631 nm p2p amplitude | $I_{\lambda_i}^{DC}$ | From Waveform analysis |
| $\lambda$ = 631 nm rise time | $I_{\lambda_i}^{p2p}$ | From Waveform analysis |
| $\lambda$ = 631 nm signal trend | $\tau_{\lambda_i}^{rise}$ | From Waveform analysis |
| $\lambda$ = 631 nm Significance coefficient | $c_{\lambda_i}$ | From Waveform analysis |
| $\lambda$ = 631 nm HRV | $T_{\lambda_i}^{HRV}$ | From Waveform analysis |
| $\lambda$ = 1450 nm AC peak | $I_{\lambda_i}^{AC}$ | From FFT |
| $\lambda$ = 1450 nm DC | $pos_{\lambda_i}^{AC}$ | From FFT |
| $\lambda$ = 1450 nm p2p amplitude | $I_{\lambda_i}^{DC}$ | From Waveform analysis |
| $\lambda$ = 1450 nm | $I_{\lambda_i}^{p2p}$ | From Waveform analysis |

TABLE 3-continued

| Name | Symbol | Equation |
|---|---|---|
| $\lambda = 1450$ nm rise time | $\tau_{\lambda_i}^{rise}$ | From Waveform analysis |
| $\lambda = 1450$ nm signal trend Significance coefficient | $c_{\lambda_i}$ | From Waveform analysis |
| $\lambda = 1450$ nm HRV | $T_{\lambda_i}^{HRV}$ | From Waveform analysis |
| $\lambda = 1550$ nm AC peak | $I_{\lambda_i}^{AC}$ | From FFT |
| $\lambda = 1550$ nm DC | $pos_{\lambda_i}^{AC}$ | From FFT |
| $\lambda = 1550$ nm p2p amplitude | $I_{\lambda_i}^{DC}$ | From Waveform analysis |
| $\lambda = 1550$ nm rise time | $I_{\lambda_i}^{p2p}$ | From Waveform analysis |
| $\lambda = 1550$ nm signal trend | $\tau_{\lambda_i}^{rise}$ | From Waveform analysis |
| $\lambda = 1550$ nm Significance coefficient | $c_{\lambda_i}$ | From Waveform analysis |
| $\lambda = 1550$ nm HRV | $T_{\lambda_i}^{HRV}$ | From Waveform analysis |
| Best Ratio pH | $BR_{pH}$ | Device Calibration |
| Best Ratio pCO2 | $BR_{pCO2}$ | Device Calibration |
| Best Ratio pHCO3- | $BR_{pHCO3^-}$ | Device Calibration |
| Acceleration magnitude | $I_{move}$ | From Accelerometer |
| GPS velocity | $|v|_{GPS}$ | From GPS |
| GPS altitude | $|alt|_{GPS}$ | From GPS |
| GPS acceleration | $|a|_{GPS}$ | From GPS |
| GPS incline | $|incline|_{GPS}$ | From GPS |

TABLE 4

Table 4 lists Y(n) = H(x(n)):

| Name | Symbol | Equation |
|---|---|---|
| Blood pH | pH | $6.1 + \log\left(\dfrac{pHCO_3^-}{0.03 pCO_2}\right)$ |
| Blood PCO2 | $pCO_2$ | $\dfrac{\epsilon_{Hb}^{CO_2} - \epsilon_{Hb}^{Hb} * I_{\lambda_{CO_2}}^{AC} * I_{\lambda_1}^{DC}/(I_{\lambda_1}^{AC} * I_{\lambda_{CO_2}}^{DC})}{\epsilon_{Hb}^{CO_2} - \epsilon_{CO_2}^{CO_2} + (\epsilon_{CO_2}^{Hb} - \epsilon_{Hb}^{Hb}) * I_{\lambda_{CO_2}}^{AC} * I_{\lambda_1}^{DC}/(I_{\lambda_1}^{AC} * I_{\lambda_{CO_2}}^{DC})}$ |
| Blood PO2 | $pO_2$ | $\dfrac{\epsilon_{Hb}^{O_2} - \epsilon_{Hb}^{Hb} * I_{\lambda_{O_2}}^{AC} * I_{\lambda_1}^{DC}/(I_{\lambda_1}^{AC} * I_{\lambda_{O_2}}^{DC})}{\epsilon_{Hb}^{O_2} - \epsilon_{O_2}^{O_2} + (\epsilon_{O_2}^{Hb} - \epsilon_{Hb}^{Hb}) * I_{\lambda_{O_2}}^{AC} * I_{\lambda_1}^{DC}/(I_{\lambda_1}^{AC} * I_{\lambda_{O_2}}^{DC})}$ |
| Blood PHCO3- | $pHCO_3^-$ | $\dfrac{\epsilon_{Hb}^{HCO_3^-} - \epsilon_{Hb}^{Hb} * I_{\lambda_{HCO_3^-}}^{AC} * I_{\lambda_1}^{DC}/(I_{\lambda_1}^{AC} * I_{\lambda_{HCO_3^-}}^{DC})}{\epsilon_{Hb}^{HCO_3^-} - \epsilon_{HCO_3^-}^{HCO_3^-} + (\epsilon_{HCO_3^-}^{Hb} - \epsilon_{Hb}^{Hb}) * I_{\lambda_{HCO_3^-}}^{AC} * I_{\lambda_1}^{DC}/(I_{\lambda_1}^{AC} * I_{\lambda_{HCO_3^-}}^{DC})}$ |

TABLE 4-continued

Table 4 lists Y(n) = H(x(n)):

| Name | Symbol | Equation |
|---|---|---|
| Blood Glucose | $pC_6H_{12}O_6$ | As above |
| Cardiac Frequency | $f_{HR}$ | As in f(x(n)) |
| Point Blood Pressure | $P_{Point}$ | As in f(x(n)) |
| Respiratory Frequency | $f_{Resp}$ | As in f(x(n)) |
| GPS velocity | $|v|_{GPS}$ | As in f(x(n)) |
| GPS altitude | $|alt|_{GPS}$ | As in f(x(n)) |
| GPS acceleration | $|a|_{GPS}$ | As in f(x(n)) |
| GPS incline | $|incline|_{GPS}$ | As in f(x(n)) |

As illustrated in Tables 3 and 4, by generating energy at different wavelengths, one or more blood metrics may be determined from the detected energy. For example, cardiac frequency, cardiac phase, cardiac harmonic amplitude, cardiac pulse pressure, point blood pressure, respiratory rate or frequency, respiratory phase, blood pH, blood $pCO_2$, blood $pHCO_{3-}$, or blood glucose, may be determined.

In step 1110, the blood metrics measurement apparatus provides the generated one or more signals for respiratory rate calculation. In some embodiments, a communication module (e.g., communication module 1008) provides the one or more signals to, for example, a respiratory rate calculation system and/or user device.

Figure 12:
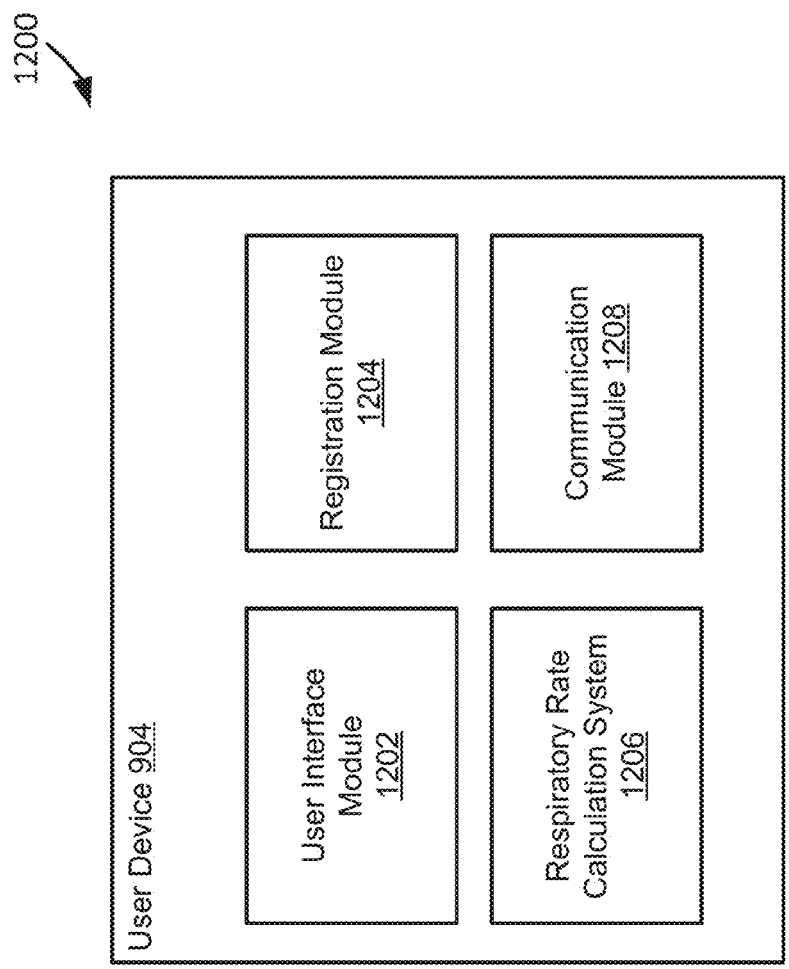
FIG. 12 depicts a block diagram of a user device according to some embodiments.

FIG. 12 depicts a block diagram 1200 of a user device 904 according to some embodiments. Generally, the user device 904 may be configured to display, or otherwise present respiratory rate values, messages, alerts, and/or the like. The user device 904 may also provide registration features allowing a user to register a blood metrics measurement device 902, create and/or update a user account, and communicate with other systems of the system and environment 900. In some embodiments, the user device 904 includes a user interface module 1202, a registration module 1204, a respiratory rate calculation system 1206, and a communication module 1208.

The user interface module 1202 may be configured to present images and/or audio corresponding to health data, such as respiratory rate values, messages, alerts, and the like. For example, the user interface module 1202 may display one or more graphical user interfaces (GUIs) to present a calculated respiratory rate to a user. Example user interfaces are described further with reference to FIG. 5-7, discussed above.

The registration module 1204 may be configured to generate registration requests to create, read, update, delete, or otherwise access, registration records associated with user accounts (e.g., a user account associated with a user of the user device 904 and/or the blood metrics measurement apparatus 902) and registration records associated with the blood metrics measurement apparatus 902. In some embodiments, a user inputs user account registration information and blood metrics measurement apparatus registration information via the user interface module 1202. For example, user account registration information may include geographic attributes, demographic attributes, psychographic attributes, and/or behavioristic attributes. Accordingly, user account registration information may include some or all of the following attributes:

User Account Identifier: Identifier that identifies a user account.

Password: Password, or other personal identifier, used to authenticate the user account. For example, it may an alphanumerical password, biometric data (e.g., fingerprint, etc.). In some embodiments, readings or measurements from the blood metrics measurement apparatus 902 may be used to authenticate the user account.

Device Identifier(s): Identifier(s) that identify one or more blood metric measurement apparatus' associated with the user account.

Name: A name of the user.

DOB: A date of birth of the user.

Age: An age of the user.

Gender: Gender of the user (e.g., female, male, transgender, or the like).

Weight: A weight of the user.

Height: A height of the user.

Skin color: A skin color of the user.

Activity Level: An activity level of the user (e.g., sedentary, lightly active, active, very active, and so forth).

Geographic location: A location of the user (e.g., as determined by a location service and/or specified by the user).

Respiratory Rate Profile

Blood Glucose Profile (e.g., Diabetes information)

Wrist circumference: Circumference of the user's wrist.

In some embodiments, the blood metrics measurement apparatus registration information includes some or all of the following attributes:

Apparatus Identifier: Identifier that identifies a blood metrics measurement apparatus.

User Account Identifier: Identifier that identifies a user account associated with the blood metrics measurement apparatus.

Geographic location: A current location of the blood metrics measurement apparatus (e.g., as determined by a location service and/or specified by the user).

Settings: One or more settings of the blood measurement metrics apparatus. For example, some or all of the settings may be automatically determined based on one or more user account attributes (e.g., height, weight, etc.) and/or by the user.

The respiratory rate calculation system 1206 may be configured to calculate respiratory rate values (e.g., BPM), and generate messages or alerts based on those values. An example of the respiratory rate calculation system 1206 is discussed further below with reference to FIG. 14.

The communication module 1208 may be configured to send requests to and receive data from one or a plurality of systems. The communication module 1208 may send requests to and receive data from a systems through a network or a portion of a network. Depending upon implementation-specific or other considerations, the communication module 1208 may send requests and receive data through a connection (e.g., the communication network 908, and/or the communication link 910), all or a portion of which may be a wireless connection. The communication module 1208 may request and receive messages, and/or other communications from associated systems.

Figure 13:
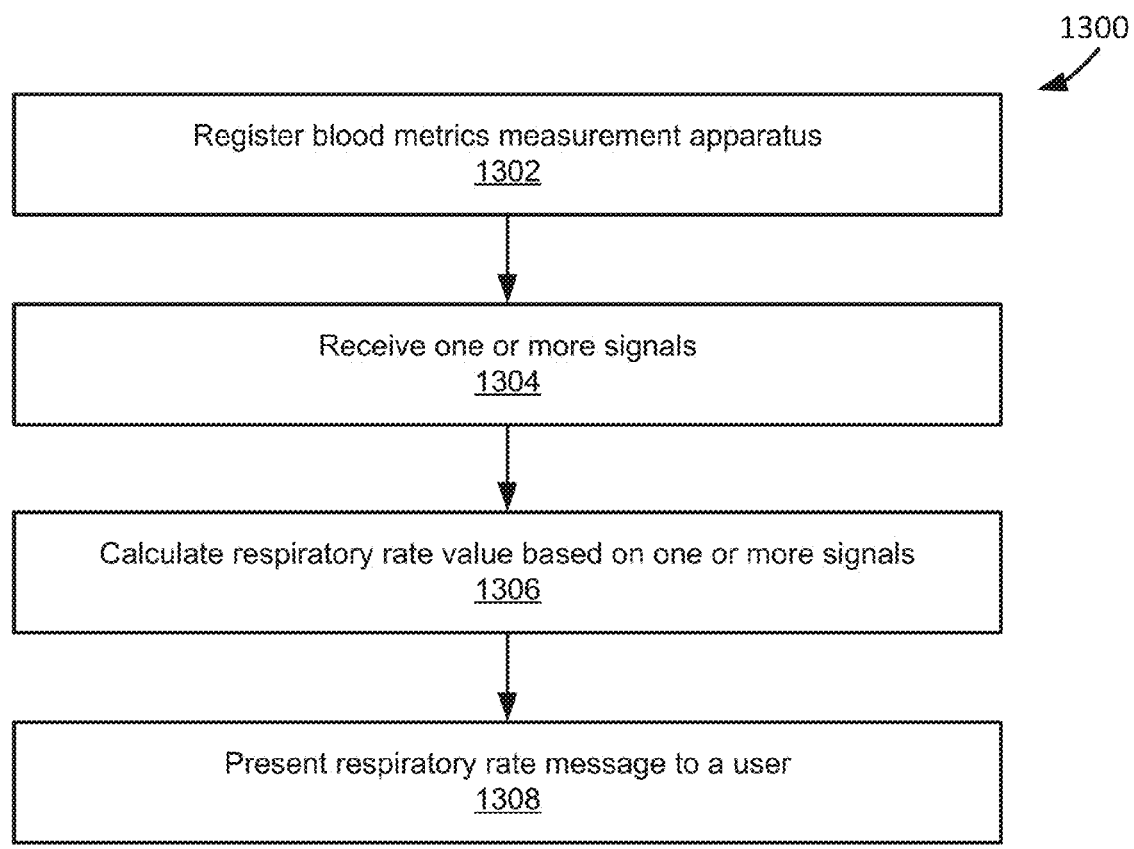
FIG. 13 depicts a flowchart of an example method of operation of a user device according to some embodiments.

FIG. 13 depicts a flowchart 1300 of an example method of operation of a user device (e.g., user device 904) according to some embodiments.

In step 1302, a user device registers a blood metrics measurement apparatus (e.g., blood metrics measurement apparatus 902). In some embodiments, input from a user is received by a user interface module (e.g., user interface module 1202) that triggers a registration module (e.g., registration module 1204) to generate a registration request to associate the blood metrics measurement apparatus with a user and/or the user device. The registration request may include, for example, one or more blood metrics measurement apparatus attributes. In some embodiments, a communication module (e.g., communication module 1208) provides the registration request to a blood metrics server (e.g., blood metrics server 906) for processing.

In step 1304, the user device receives one or more signals from the registered blood metrics measurement apparatus. In some embodiments, the one or more signals comprise optical signals and/or one or more non-optical signals. In some embodiments, the one or more signals may be received by the communication module.

In step 1306, the user device calculates one or more respiratory rate values (e.g., BPM values) based on the received one or more signals. In some embodiments, a respiratory rate calculation system calculates the one or more respiratory rate values. Although this example depicts the user device calculating the one or more respiratory rate values, it will be appreciated that one or more other systems having the functionality of a respiratory rate calculation system may perform the calculation. For example, in some embodiments, the blood metrics measurement apparatus and/or the blood metrics server may include such functionality and perform the calculation.

In step 1308, the user device presents a respiratory rate message to the user based on at least one of the one or more calculated respiratory rate values. For example, the message may include some or all of the respiratory rate values, alerts (e.g., high RR, low RR, and the like) based on one or more of the calculated values, and so forth. In some embodiments, the user device presents (e.g., via images, audio, vibrations, etc.) the respiratory rate message or alert to the user via the user interface module, or other feature of the user device.

Figure 14:
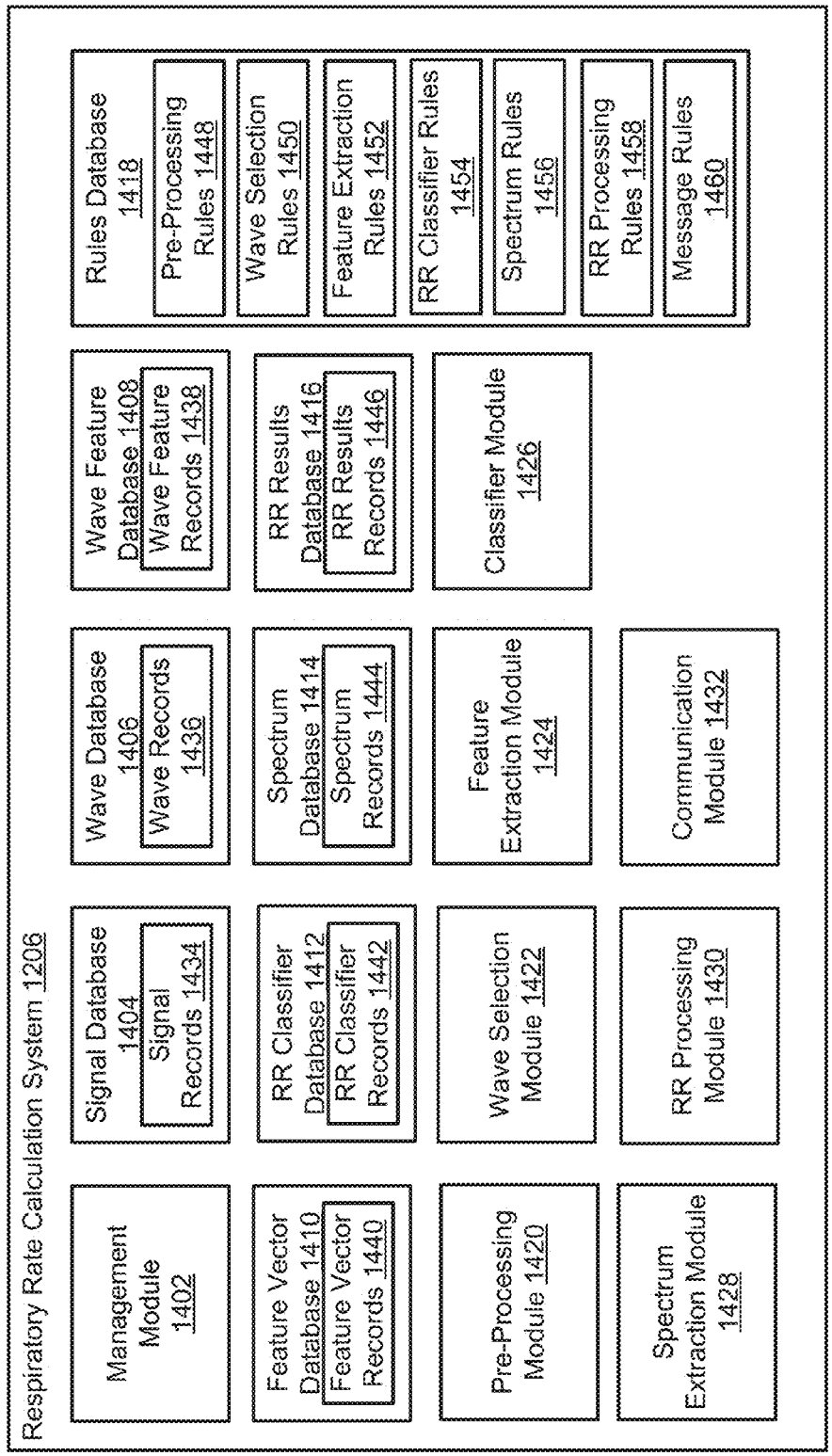
FIG. 14 depicts a block diagram of a respiratory rate calculation system according to some embodiments.

FIG. 14 depicts a block diagram 1400 of a respiratory rate calculation system 1206 according to some embodiments. Generally, the respiratory rate calculation system 1206 may be configured to calculate respiratory rate values of a user. The respiratory rate calculation system 1206 may also store calculated respiratory rate values (e.g., for health tracking, etc.), and communicate with other systems of the system and environment 900. In some embodiments, the respiratory rate calculation system 1206 includes a management module 1402, a signal database 1404, a wave database 1406, a wave feature database 1408, a feature vector database 1410, a respiratory rate classifier database 1412, a spectrum database 1414, a respiratory rate results database 1416, a rules database 1416, a pre-processing module 1420, a wave selection module 1422, a feature extraction module 1424, a respiratory rate processing module 1430, and a communication module 1432.

The management module 1402 may be configured to manage (e.g., create, read, update, delete, or access) signal records 1434 stored in the signal database 1404, wave records 1436 stored in the wave database 1406, wave feature records 1438 stored in the wave feature database 1408, feature vector records 1440 stored in the feature vector database 1410, respiratory rate classifier records 1442 stored in the respiratory rate classifier database 1412, spectrum records stored in spectrum database 1414, respiratory rate result records 1446 stored in the respiratory rate results database 1416, and/or rules 1448-1460 stored in rules database 1416. The management module 1402 may perform these operations manually (e.g., by an administrator interacting with a GUI) and/or automatically (e.g., by one or more of the modules 1420-1430). In some embodiments, the management module 1402 comprises a library of executable instructions which are executable by a processor for performing any of the aforementioned management operations. The databases 1404-1418 may be any structure and/or structures suitable for storing the records 1434-1446 and/or the rules 1448-1460 (e.g., an active database, a relational database, a table, a matrix, an array, a flat file, and the like).

The signal records 1434 may include a variety of signals, along with associated metadata. For example, the signals may comprise multichannel optical and/or non-optical signals. In some embodiments, the metadata may include information obtained from the signals, such as heart rate(s) of an associated user. For example, the signal records 1434 may store some or all of the following information:

Signal(s) Identifier: Identifier that identifies the stored signal(s).

Figure 19:
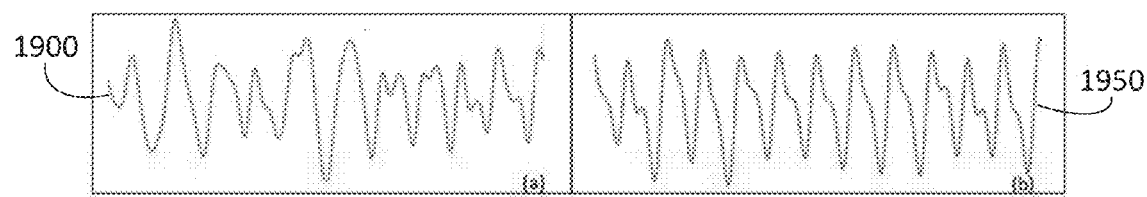
FIG. 19 depicts an example noisy PPG signal and an example filtered PPG signal according to some embodiments.

Signal(s): one or more signals. The signals may be raw signals (e.g., as detected by the associated respiratory rate measurement apparatus), filtered or pre-processed signals (e.g., to remove noise from the signals), and/or normalized signal values (e.g., between 0-1). An example "noisy" (i.e., unfiltered) PPG signal and an example filtered PPG signal are shown in FIG. 19. It will be appreciated that, a "signal," such as a PPG signal or pressure pulse signal, generally refers to a filtered signal, although in some embodiments, it may also refer to an unfiltered signal instead of, or in addition to, the filtered signal.

Set(s) of Waves: one or more sets of waves of a predetermined time series or window (e.g., 30 seconds) of the signal. The waves may include raw waves, filtered waves, and/or normalized wave values (e.g., between 0-1).

Apparatus Identifier: Identifier that identifies the blood metrics measurement apparatus that generated the signals.

User Account Identifier: Identifier that identifies a user account associated with the blood metrics measurement apparatus that generated the signals.

Metadata: Metadata obtained from the signals, such as heart rate or other biometric data. The metadata may also include other information of the user, such as gender, age, height, weight, skin color (e.g., obtained from the user's account information). Such metadata values may be used by the respiratory rate processing module 1430 (discussed below) to facilitate calculation of respiratory rate values. In some embodiments, metadata values may be provided to an respiratory rate classifier (discussed below) via sets of feature vectors (discussed below) and/or be provided separately to the classifier.

The wave records 1436 may include sets of waves of a signal (e.g., a signal stored in the signal database 1404). In some embodiments, the wave records 1436 may store some or all of the following information:

Signal Identifier: Identifier that identifies an associated signal.

Wave Identifier(s): Identifiers for waves of the associated signal.

Apparatus Identifier: Identifier that identifies the blood metrics measurement apparatus that generated the signals.

User Account Identifier: Identifier that identifies a user account associated with the blood metrics measurement apparatus that generated the signals.

The wave feature records 1438 may include wave features of associated waves of a signal. For example, wave features may include wave peaks, wave valleys, wave edges, optical ratios, heart rate, signal level and range, signal metrics, energy in different frequency ranges, and/or the like. In some embodiments, the wave feature records 1438 may store some or all of the following information:

Signal Identifier: Identifier that identifies an associated signal.

Wave Identifier(s): Identifiers for the subsets of waves of the associated signal.

Wave Features: one or more features obtained from the waves. The wave features may be stored as normalized wave values (e.g., between 0-1).

Apparatus Identifier: Identifier that identifies the blood metrics measurement apparatus that generated the signals.

User Account Identifier: Identifier that identifies a user account associated with the blood metrics measurement apparatus that generated the signals.

The feature vector records 1440 may include sets of features generated based on the wave features of associated waves of a signal. In some embodiments, the feature vector records 1440 may store some or all of the following information:

Signal Identifier: Identifier that identifies an associated signal.

Wave Identifier(s): Identifier(s) for wave(s) of the associated signal.

Figure 21:
FIG. 21 depicts an example feature vector according to some embodiments.

Set(s) of Feature Vectors: one or more sets of feature vectors, each feature vector comprising features extracted from a wave. The values of a feature vector may include measurement values and metric values. For example, the measurement values may correspond to amplitude or location points of a particular wave, and the metric values may be generated from metric functions that use at least one of the measurement values. The values of a feature vector may comprise normalized values (e.g., between 0-1). An example feature vector 2100 is shown in FIG. 21.

Apparatus Identifier: Identifier that identifies the blood metrics measurement apparatus that generated the signals.

User Account Identifier: Identifier that identifies a user account associated with the blood metrics measurement apparatus that generated the signals.

The respiratory rate classifier records 1442 may include one or more respiratory rate classifiers. In some embodiments, respiratory rate classifiers may comprise a machine learning algorithm (e.g., a Support Vector Machine (SVM) or Random Forests algorithm). In some embodiments, respiratory rate classifiers may facilitate determining filter parameters for filtering signals during pre-processing. The classifiers may include various types of respiratory rate classifiers. For example, a first type may be a "non-specific" classifier which does not require calibration in order to be used to calculate respiratory rate values. A second type may be a "specific" classifier which requires calibration in order to be used to calculate respiratory rate values. For example, classifiers of the second type may require information about the user, such age, weight, height, gender, skin color, and/or the like. In some embodiments, the respiratory rate records 1442 may store some or all of the following information:

Classifier Identifier: Identifies an respiratory rate classifier.

Classifier Type: Identifies a type of classifier (e.g., non-specific or specific).

Classifier Parameters: Various classifier parameters used to determine filter parameters for filtering signals during pre-processing based on feature vectors.

Apparatus Identifier(s): Identifier(s) that identify one or more blood metrics measurement apparatus' using the respiratory rate classifier.

User Account Identifier(s): Identifier(s) that identify one or more user account(s) associated with the blood metrics measurement apparatus that use the respiratory rate classifier.

The spectrum records 1436 may include determined or estimated spectrums of a signal (e.g., a signal stored in the signal database 1404). In some embodiments, the spectrum records 1436 may store some or all of the following information:

Signal Identifier: Identifier that identifies an associated signal.

Spectrum Identifier(s): Identifiers for spectrums of the associated signal.

Apparatus Identifier: Identifier that identifies the blood metrics measurement apparatus that generated the signals.

User Account Identifier: Identifier that identifies a user account associated with the blood metrics measurement apparatus that generated the signals.

The respiratory rate results records 1446 may include one or more calculated respiratory rate values. In some embodiments, the respiratory rate results records 1446 may store some or all of the following information:

Respiratory Rate Result Identifier: Identifies a set of one or more calculated respiratory rate values.

Respiratory Rate Values: one or more calculated respiratory rate values.

Date: A date and/or time the respiratory rate was calculated.

Messages: Message identifier and/or messages generated based on the calculated respiratory rate values.

Signal Identifier: Identifier that identifies an associated signal.

Wave Identifier(s): Identifiers for the waves of the associated signal.

Feature Vectors Identifier(s): Identifiers for the one or more sets of feature vectors used to calculate select, configure, and/or train an associated classifier.

Apparatus Identifier: Identifier that identifies the blood metrics measurement apparatus that generated the signals.

User Account Identifier: Identifier that identifies a user account associated with the blood metrics measurement apparatus that generated the signals.

Pre-Processing Rules 1448

The pre-processing rules 1448 define attributes and/or functions for filtering signals. For example, a signal may be corrupted with noise from various sources (e.g., high frequency ambient noise, electronic noise, and the like). In some embodiments, the signal may be signal from a photodiode, output of a pressure sensor, output of an accelerometer, output of a gyroscope, or the like. The signal may be filtered to remove corrupting noise, as well as enhance a strength of the signal.

Typically, respiration is a slowly varying signal, often not more than 40 BPM (or 0.67 Hz), and the signal may need to be measured over longer durations (e.g., relative to pulse rate, which can usually be measured at an interval of 1 second) before a respiratory rate can be determined. For example, a 30 second window may be used over a PPG window, sampled upwards of 50 Hz. In some embodiments, the respiration signal may include information less than 1 Hz, and it can be decimated up to 2 Hz before processing (e.g., for computational efficiency). In some embodiments, pre-processing may apply a high pass filter (e.g., at cut-off 0.1 Hz) to eliminate, reduce, remove and/or attenuate (or, collectively, "remove") low frequency drift inherit to signals. In some embodiments, the high pass filter may have a narrow transition band (e.g., 0.05 Hz). In some embodiments, Savitzky-Golay filtering may be both computationally efficient and effective in eliminating low-frequency drift. In some embodiments, if the filter order is high, it may also eliminate some useful high frequency components of the signal. In some embodiments, a classifier may be used to determine appropriate or optimized filter parameters.

Figure 22:
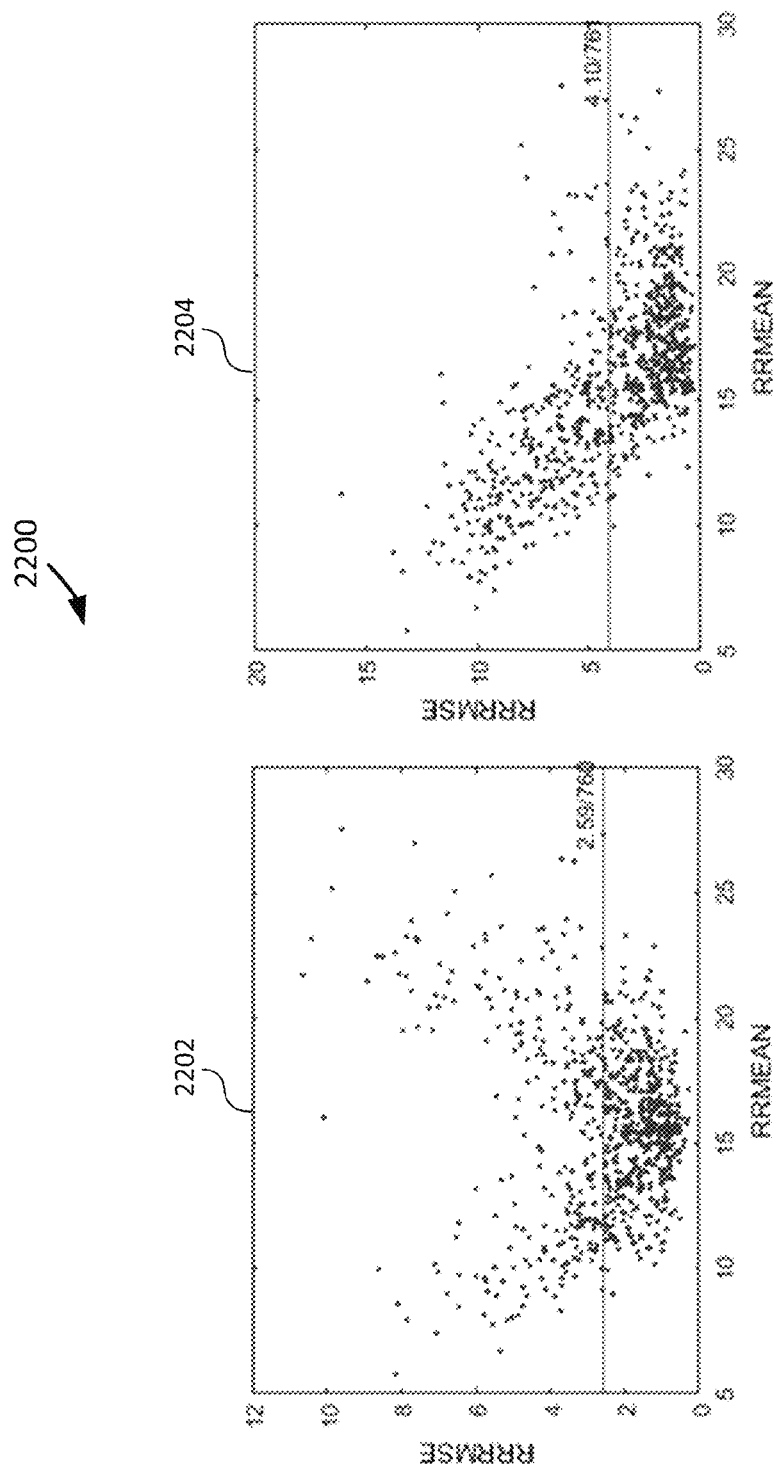
FIG. 22 depicts example error distribution plots of respiration rate estimation for two different set of filter parameters according to some embodiments

In some embodiments, filter parameters are determined based on a true respiration rate. Accordingly, a classifier may be generated or trained to identify categories of respiration rate (e.g., low and high) based on signal data. In some embodiments, the classifier may be applied to determine filter parameters for filtering during pre-processing (e.g., using low pass, high pass, or other filters). Example error distribution plots 2202 and 2204 of respiration rate estimation for two different set of filter parameters are shown in FIG. 22.

The pre-processing module 1420 may be configured to execute the pre-processing rules 1448. Thus, for example, the pre-processing module 1420, using some or all of the associated signals and/or values stored in the signal records 1434, may filter signals and store the resulting filtered signals. The wave database 1406 may be configured to store the signals filtered by the pre-processing module 1420.

Wave Selection Rules 1450

The wave selection rules 1450 define attributes and/or functions for selecting (or, "extracting") one or more waves or sets of waves from a signal. For example, waves of a predetermined time series (e.g., 30 seconds) may be extracted from a signal. The wave selection module 1422 may be configured to execute the wave selection rules 1442. Thus, for example, the wave selection module 1422, using some or all of the associated waves and/or values stored in the signal records 1434, may extract waves over or from a predetermined time series. The wave database 1406 may be configured to store the extracted waves.

Feature Extraction Rules 1452

The feature extraction rules 1452 define attributes and/or functions for identifying (or, "extracting") features of waves of a signal. In some embodiments, features may be concatenated or combined to form feature vectors. Once the features are extracted, they may be used with ground truth data to train respiratory rate classifiers. Examples features are described below, although it will be appreciated that like the other examples in this paper, these are non-limiting examples.

In some embodiments, features may include, but are not limited to, pulse transit time (PTT) features, reflection features, signal level and range features, signal metric features, optical ratio features, heart rate features, wave width and derivative features, user information features, and/or pressure features. PTT features may include a transit time feature, joint entropy feature, and/or wave type feature. Pulse transit time may be measured as the time taken for the pulse pressure wave to propagate along the length of the arterial tree. For example, this may be the difference in time between the onset of the R-wave on ECG, and the pulse wave peak on the finger. In other embodiments, the transit time may be measured as the time taken for blood to travel from one LED-PD system to another LED-PD system, which may be separated from each other by a predetermined distance (e.g., 15 mm). Sampling at a very high rate (>2 KHz) may help resolve features in both LED-PD systems. In some embodiments, the transit time may be measured as (1) the distance between the valleys in the corresponding waves in respective LED-PD systems at the start of the systolic cycle, and/or (2) the distance between the peaks in first derivatives between the two LED-PD systems. The transit time may be expressed in any units (e.g., milliseconds).

The joint entropy feature may be a measurement of similarity between fast channels of respective LED-PD systems. High pulse pressure may correlate with low entropy or high mutual information shared between the fast LED channels. The joint entropy feature may be expressed in bytes.

Wave type features may include different types of waves. For example, different types of waves may include slow type waves and fast type waves. The wave types feature may quantify a relative position of the systolic peak within the wave (0<WaveType<1) for each of the fast channels in respective LED-PD systems, where small values correspond to a slow type waves and larger values correspond to fast type waves.

A pulse decomposition may track a pulse pressure wave. As the pressure wave travels in the arterial systems, it may encounter branching points where the diameter of arteries may decrease rapidly. The pressure wave may bounce on such branching points and send reflection waves in different (e.g., opposite) directions. In some embodiments, the original pressure wave plus the reflections may form the observed pressure pulse, which in turn may be observed in a signal (e.g., PPG signal). Multiple reflections (e.g., four reflections), in some embodiments, may be used to identify multiple features and amplitudes (e.g., four features and four amplitudes). The time of occurrence of the systolic peak from the start of the systolic cycle (i.e., systolic peak time) may also be included as a feature. A ratio between the second derivatives at the bottom and peak of the systolic cycle may be used as a feature. This feature has been correlated with arterial stiffness. Ten features may be individually identified for each LED channel.

The signal level and range features comprise the mean value and range of a signal (e.g., PPG signal) determined for each of the channels. In some embodiments, the signal metrics features include Hjorth parameters, perfusion, kurtosis, and energy. Hjorth parameters may describe activity, mobility and complexity of the signal, and are commonly used tools in EEG analysis. Perfusion may be measured as the ratio between the AC and DC components of the signal (i.e. the range of the signal and the mean). Kurtosis may be measured over the signal analysis window. Energy may the variance of the signal measured over the analysis window. In some embodiments, optical ratio features may be calculated as the ratio of the range of the LEDs (measured in pairs across wavelengths) after normalization of the respective signals, and heart rate features may be an actual user heart rate or a default heart rate.

In various embodiments, if two LEDs at the same wavelength are positioned at different locations of the same artery, a phase shift may be obtained between the measured signals (e.g., due to blood flow). This may facilitate calculation of pulse wave velocity (PWV) and/or pulse transit time (PTT), both of which may be included in a feature vector, and/or otherwise provided to the empirical respiratory rate model used to calculate respiratory rate values.

The user information features such as a user's gender, age, skin color, height and/or weight may be included in a feature vector, and/or otherwise provided to the empirical respiratory rate model used to calculate respiratory rate values. In some embodiments, pressure features may include the mean value of the pressure signal over the analysis window (or "baseline mean") and range of the pressure signal over the analysis window (or, "AC").

The feature extraction module 1424 may be configured to execute the feature extraction rules 1452. Thus, for example, the feature extraction module 1422, using some or all of the associated subsets of waves and/or values stored in the wave records 1436, may identify one or more feature of the waves within the subsets of waves, and generate corresponding sets of feature vectors. An example of a feature vector 2100 is shown in FIG. 21. The wave feature database 1408 may be configured to store the wave features identified by the feature extraction module 1424, and the feature vector database 1410 may be configured to store the generated sets of feature vectors.

Respiratory Rate Classifier Rules 1454

The respiratory rate classifier rules 1454 define attributes and/or functions for generating, selecting, and/or training respiratory rate classifiers for determining filter parameters for use during signal pre-processing. In some embodiments, the respiratory rate classifier rules 1454 may define input values for a respiratory rate classifiers. For example, input values may comprises sets of features vectors and ground truth data.

In some embodiments, respiratory rate classifiers may be trained using machine learning. For example, features may extracted from individual waves as well as the signal window from which it is extracted. Features may be grouped by optical ratios, heart rate, signal level and range (e.g., mean value, range of signals), signal metrics (e.g., Hjorth parameters, Perfusion, Kurtosis, Interquartile range (IQR)), zero-crossings, and/or energy of spectrum in different frequency ranges. Features from some or all of the groups may be concatenated or combined to form feature vectors, and may be used for classifier learning and feature selection processes. In some embodiments, a particular subset of features may be used (e.g., Hjorth parameters, IQR and the energy measured from the high frequency range of the spectrum) to form feature vectors.

In some embodiments, ground truth data may be collected (e.g., by a Masimo device) and stored, and the wave feature vectors may be used to train a classifier (e.g., a Support Vector Machine (SVM)). Performance metrics may be used to assess a particular classifier and select which classifier to use for particular situations and environments. For example, the performance metrics may include a confusion matrix, receiver operation curve (ROC), area under curve (AUC), and F-1 score. The trained classifier may be used in conjunction with the respiration rate analysis to determine filter parameters.

The classifier module 1426 may be configured to execute the classifier rules 1454. For example, the classifier module 1422, using one or more classifiers stored in the classifier records 1442 and associated ground truth data and feature vectors, may define a set of filter parameters for pre-processing signals (e.g., by the pre-processing module 1420).

Spectrum Rules 1456

The spectrum rules 1456 define attributes and/or functions for extracting (or, "estimating") a spectrum of a signal. Typically, signal based respiration rate estimation techniques typically use a single channel (e.g., one LED and photodetector pair) measurement obtained on a digit (e.g., finger pulse), and the signal is typically acquired under clinical conditions where the user is generally not in a state of motion. Additionally signals measured on the finger may be much stronger relative to signals measured on the wrist.

For example, when a user wears a measurement device on the wrist, the signal may be relatively weak (e.g., compared to finger pulse). In some embodiments, the spectrum rules 1456 may compensate for weak signals by causing multiple LEDs, configured at the same or different wavelengths, to each produce a signal of the same width concurrently (i.e., time multiplexed). In various embodiments, a pre-processed pressure sensor signal and accelerometer signals may also be used for spectrum estimation (i.e., sensor fusion). The pressure sensors may be less sensitive to motion artifacts than optical sensors, and data fusion may be effective in obtaining more accurate spectrum estimation.

The spectrum rules 1456 may define non-parametric and/or parametric spectrum extraction functions for determining the spectrum of the multichannel signal. In some embodiments, non-parametric spectrum extraction estimates power spectral density of a signal over a frequency content of the signal, and may be used to identify key frequencies in periodic signals. Parametric spectrum extraction may use autoregressive modeling that describe a series output as a weighted sum of its previous outputs.

The spectrum module 1428 may be configured to execute the spectrum rules 1456. Thus, for example, the spectrum module 1428, using one or more signals stored in the signal records 1434, may extract or estimate a respiratory rate spectrum of a signal.

Respiratory Rate Processing Rules 1458

Figure 23:
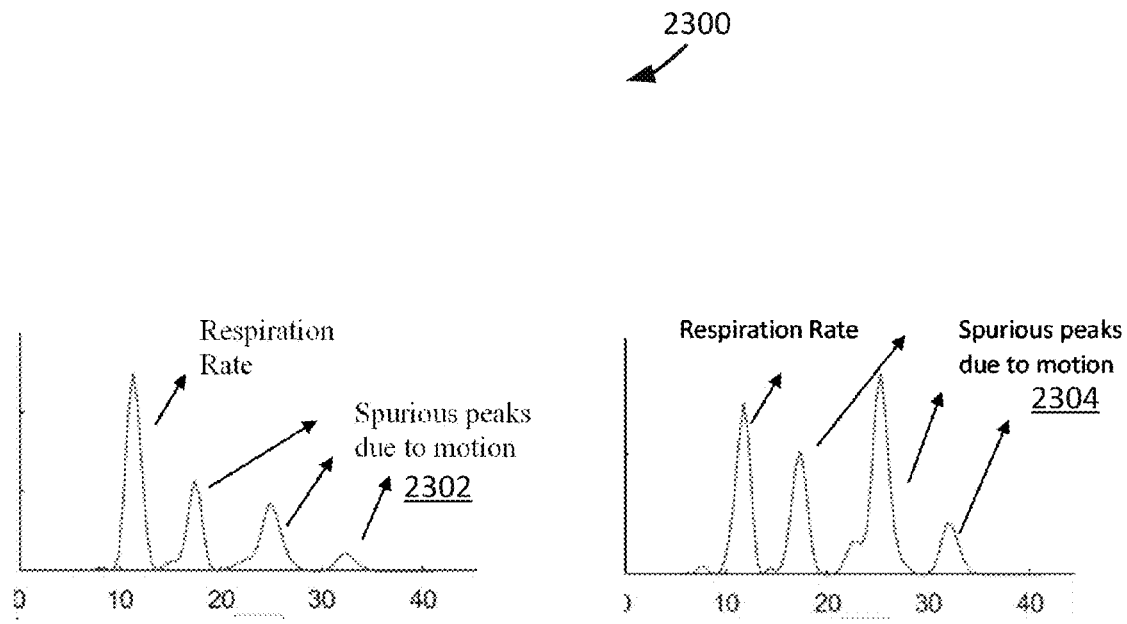
FIG. 23 depicts example estimated spectrums of a multichannel signal according to some embodiments.

The respiratory rate processing rules 1458 define attributes and/or functions for removing signal noise (e.g., motion related noise) and calculating respiratory rate values of a user. In some embodiments, the respiratory rate processing rules 1458 may calculate respiratory rates based on a strongest peak with harmonics in the spectrum in noise-free situations. Harmonics may be apparent at integer multiples of the respiratory rate. For example, if true respiratory rate is 11 BPM, then harmonics at 22 BPM and 33 BPM may be detected. These harmonics usually have weaker amplitudes than true respiratory rate and may be detected and distinguished from the respiratory rate peak. Ambient noise and motion related may introduce other peaks stronger than respiratory rate peak (e.g., as shown in FIG. 23) or may amplify high frequency harmonics of respiratory rate. Accordingly, false estimates may be measured.

The respiratory rate processing rules 1458 define a temporal filter (e.g., a Kalman filter) to compensate for false estimates. In the some embodiments, the temporal filter may be a linear quadratic estimation that uses a series of noisy measurements and the information related to previous time points, which may produce more precise estimates than can be achieved using a single measurement. The temporal filter may assume the true state at time k may be evolved from the state k−1. For example, the linear formulae of the temporal filter at time k may be $x_k = F_k x_{k-1} + B_k u_k + w_k$, where $F_k$ is the state transition matrix, $B_k$ control-input model, $x_k$ the state matrix, $u_k$ control input and $w_k$ the process noise, drawn from a zero mean multivariate Gaussian distribution with covariance $Q_k$. In some embodiments, ARIMA models or auto-regressive (AR) models may be used.

In various embodiments, the temporal filter may comprise $z_k = H_k x_k + v_k$, where $H_k$ is the observation matrix, $z_k$ observation vector, and $v_k$ the measurement noise vector, again drawn from a zero mean multivariate Gaussian distribution with covariance $R_k$. The temporal filter may, in some embodiments, operate in two phases (e.g., a first phase (or, a "predict" phase) and a second phase (or, an "update" phase)). In the predict phase, the state vector and the estimate covariance matrix may be predicted using the state vector from previous time point. In the update phase, the predictions and measurements may be incorporated to calculate a Kalman Gain and update the state vector. In some embodiments, if an observation is not available, the update phase may be skipped and the predict phase may be performed multiple times. Similarly, the update phase may be repeated multiple times if multiple observations are available at time k. In some embodiments, the formulae for the predict and update phases may be as follows:

Predict:

$$\hat{x}_{k|k-1} = F_k \hat{x}_{k-1|k-1} + B_k u_k$$

$$P_{k|k-1} = F_k P_{k-1|k-1} F_k^T + Q_k$$

Update:

$$y_{k|k-1} = z_k - H_k \hat{x}_{k-1|k-1}$$

$$S_k = H_k P_{k|k-1} H_k^T + R_k$$

$$K_k = P_{k|k-1} H_k^T S_k^{-1}$$

$$\hat{x}_{k|k} = \hat{x}_{k|k-1} + K_k y_k$$

$$P_{k|k} = (I - K_k H_k) P_{k|k-1}$$

The respiratory processing rules 1458 may define a non-linear model adapted for the measurement and state-space models (e.g., an extended Kalman filter).

In some embodiments, noise statistics of the measurements, $R_k$, may be provided to the temporal filter. For example, a noise reference may be obtained from the estimated spectrum of the measured signals (e.g., by the module 1428 executing rules 1456). The noise reference may comprise a ratio of the captured harmonic to the next strongest peak after the captured harmonic. The temporal filter may extract some or all of the possible peaks with harmonics that can correspond to respiration rate. Spurious peaks (e.g., due to motion) may be mistakenly captured by the temporal filter. The rules 1458, may compensate using the noise reference and/or one or more previous estimates of the respiration rate scaled by empirically obtained AR coefficients. Accordingly, the true respiration rate peak may be emphasized, while spurious peaks (e.g., due to motion) may be deemphasized.

The respiratory rate processing module 1430 may be configured to execute the respiratory rate processing rules 1458. Thus, for example, the respiratory rate processing module 1430, using an respiratory rate classifier stored in the respiratory rate classifier database 1412, along with some or all of the associated sets of feature vectors and/or values stored in the feature vector records 1446, may calculate one or more respiratory rate values. The respiratory rate results database 1416 may be configured to store the respiratory rate values calculated by the respiratory rate processing module 1430.

Message Rules 1460

The message rules 1460 define attributes and/or functions for generating messages and/or alerts based on respiratory rate values. In some embodiments, the message rules 1460 may define rules that cause the respiratory rate calculation system 1206 to provide calculate respiratory rate values to a user. In some embodiments, the message rules 1460 may include threshold values and/or conditions that when exceeded and/or satisfied, trigger a message or alert. For example, a threshold value (or value range) and/or threshold condition may be associated with varying respiratory rate levels, and a calculated respiratory rate value which satisfies a corresponding threshold condition or value may trigger a message or alert (e.g., indicating the corresponding respiratory rate level).

In some embodiments, the communication module 1432 may be configured to execute the message rules 1460. Thus, for example, the communication module 1422, using some or all of the respiratory rate values stored in the respiratory rate results records 1446, may generate one or more messages. The communication module 1432 may be configured to provide those messages to a user.

In some embodiments, the communication module 1432 may be configured to send requests to and receive data from one or a plurality of systems. The communication module 1432 may send requests to and receive data from a systems through a network or a portion of a network. Depending upon implementation-specific or other considerations, the communication module 1432 may send requests and receive data through a connection (e.g., the communication network 908, and/or the communication link 910), all or a portion of which may be a wireless connection. The communication module 1432 may request and receive messages, and/or other communications from associated systems.

Figure 15A:
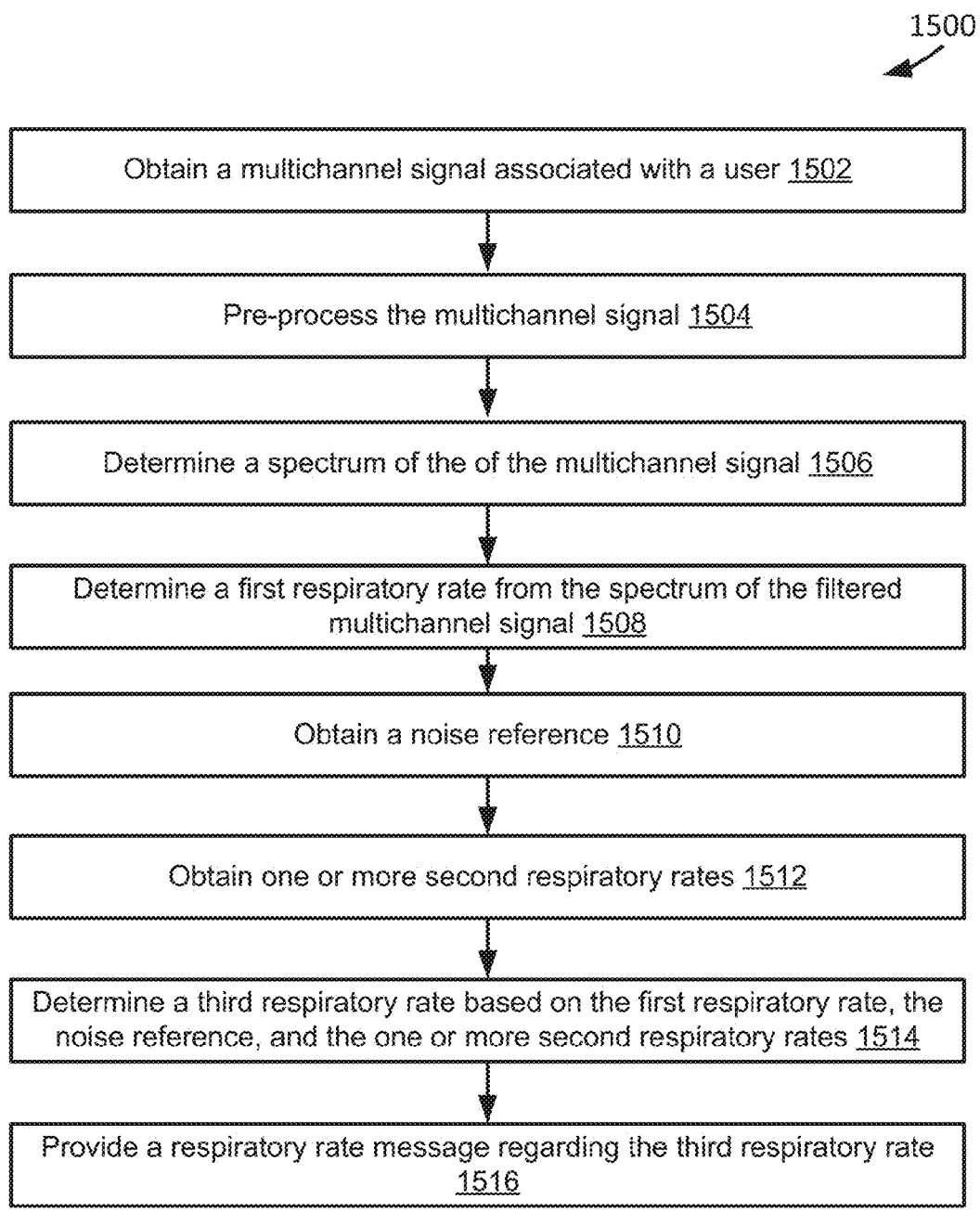
FIG. 15A depicts a flowchart of an example method of operation of a respiratory rate calculation system according to some embodiments.

FIG. 15A depicts a flowchart 1500 of an example method of operation of a respiratory rate calculation system (e.g., respiratory rate calculation system 1206) according to some embodiments.

In step 1502, a respiratory rate calculation system obtains a signal. For example, the signal may comprise a multichannel PPG signal generated from light energy emitted at the same or different wavelengths (e.g., 523 nm, 590 nm, 623 nm, 660 nm, 740 nm, 850 nm, or 940 nm) from one or more light sources (e.g., multiple LEDs) in the tissue of a user. Multichannel signals and/or different light sources may help ensure, for example, that good quality signals may be obtained in a variety of circumstances (e.g., a user moving, walking, running, sleeping, and so forth). In some embodiments, the signal may be obtained from a blood metrics measurement apparatus (e.g., apparatus 906) worn on the wrist of a user.

In step 1504, the respiratory rate calculation system pre-processes (e.g., filters) the multichannel signals. In some embodiments, a pre-processing module (e.g., pre-processing module 1420) executes pre-processing rules (e.g., rules 1448) to filter the multichannel signal.

In step 1506, the respiratory rate calculation system determines a spectrum of the multichannel signal. In some embodiments, spectrum rules (e.g., rules 1456) are executed by a spectrum module (e.g., module 1428) to determine the spectrum of the multichannel signal.

In step 1508, the respiratory rate calculation system determines a first respiratory rate from the spectrum of the signal. For example, the first respiratory rate may comprise a noisy respiratory rate which may not accurately reflect an actual respiratory rate. In some embodiments, respiratory rate processing rules (e.g., rules 1458) may be executed by a respiratory rate processing module (e.g., module 1430) to determine the first respiratory rate.

In step 1510, the respiratory rate calculation system obtains a noise reference. For example, the noise reference may be obtained from the estimated spectrum determined in step 1506. In some embodiments, the respiratory rate processing module obtains the noise reference.

In step 1512, the respiratory rate calculation system obtains one or more second respiratory rates. In some embodiments, the one or more second respiratory rates may be previously determined respiratory rates of the user. For example, the one or more second respiratory rates have been obtained within a predetermined amount of time of the current respiratory rate calculation (e.g., the respiratory rates from with 10 seconds of any of the steps 1502-1512).

In step 1514, the respiratory rate calculation system determines a third respiratory rate based on the first respiratory rate, the noise reference, and the one or more second respiratory rates. In some embodiments, the respiratory rate processing module determines the third respiratory rate.

In step 1516, the respiratory rate calculation system provides a respiratory rate message regarding the third respiratory rate. In some embodiments, a communication module (e.g., communication module 1432) provides the message to the user.

Figure 15B:
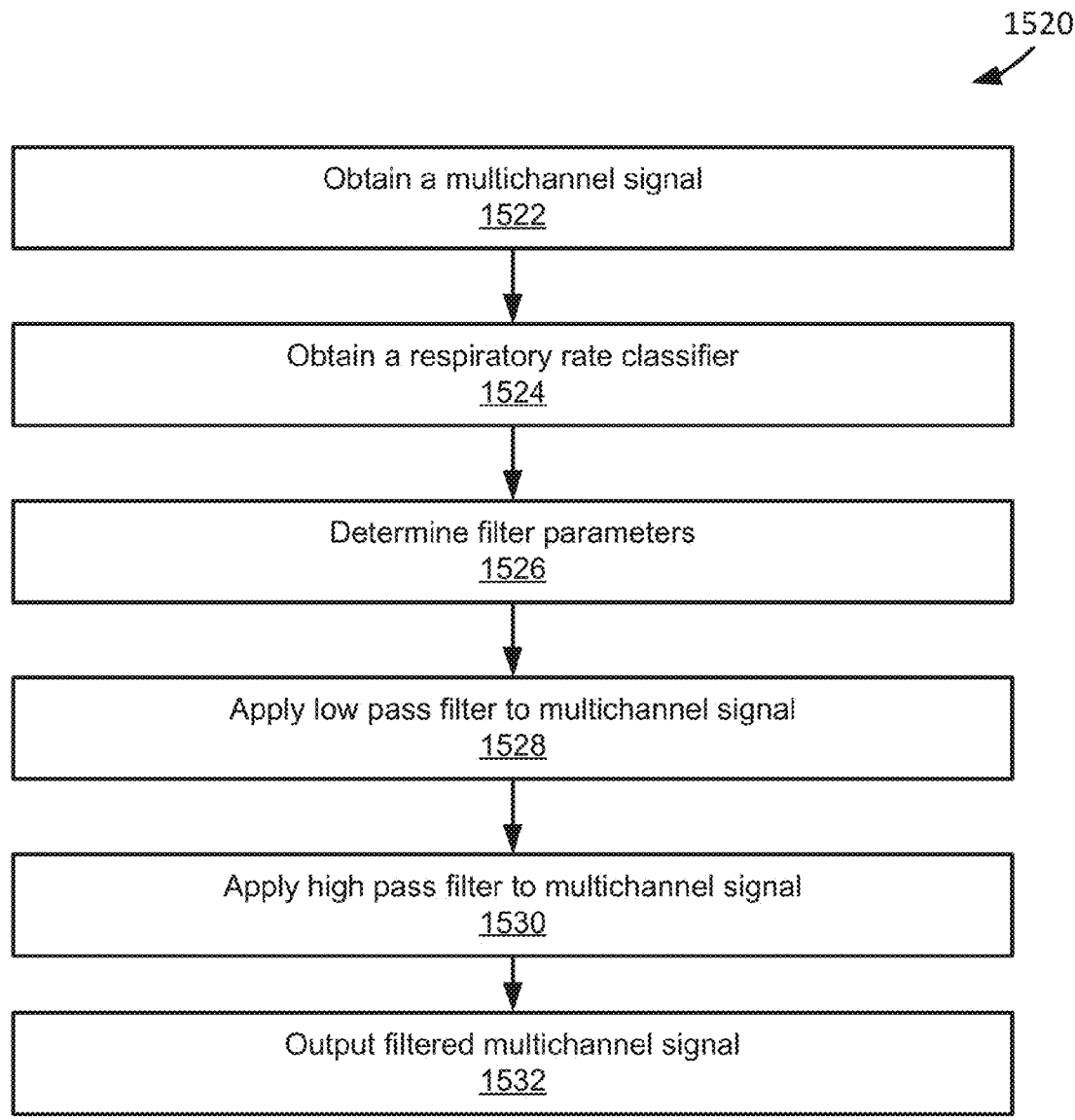
FIG. 15B depicts a flowchart of an example method of operation of a respiratory rate calculation system for filtering multichannel signals according to some embodiments.

FIG. 15B depicts a flowchart 1520 of an example method of operation of a respiratory rate calculation system (e.g., respiratory rate calculation system 1206) for filtering multichannel signals according to some embodiments.

In step 1522, a respiratory rate calculation system obtains a multichannel signal. In some embodiments, the signal may be obtained from a blood metrics measurement apparatus worn on the wrist of a user.

In step 1524, the respiratory rate calculation system obtains a respiratory rate classifier. In some embodiments, a classifier module (e.g., module 1426) executes classifier rules (e.g., rules 1454) to obtain the respiratory rate classifier.

In step 1526, the respiratory rate calculation system determines one or more filter parameters. In some embodiments, the classifier module executes the classifier rules to determine the parameters.

In step 1528, the respiratory rate calculation system applies a low pass filter to the multichannel signal. In some embodiments, the low pass filter is configured using some or all of the one or more filter parameters. In some embodiments, a pre-processing module (e.g., module 1420) configures and/or applies the low pass filter.

In step 1530, the respiratory rate calculation system applies a high pass filter to the multichannel signal. In some embodiments, the high pass filter is configured using some or all of the one or more filter parameters. In some embodiments, the pre-processing module configures and/or applies the high pass filter.

In step 1532, the respiratory rate calculation system outputs a filtered multichannel signal. In some embodiments, the pre-processing module outputs the filtered multichannel signal.

Figure 16:
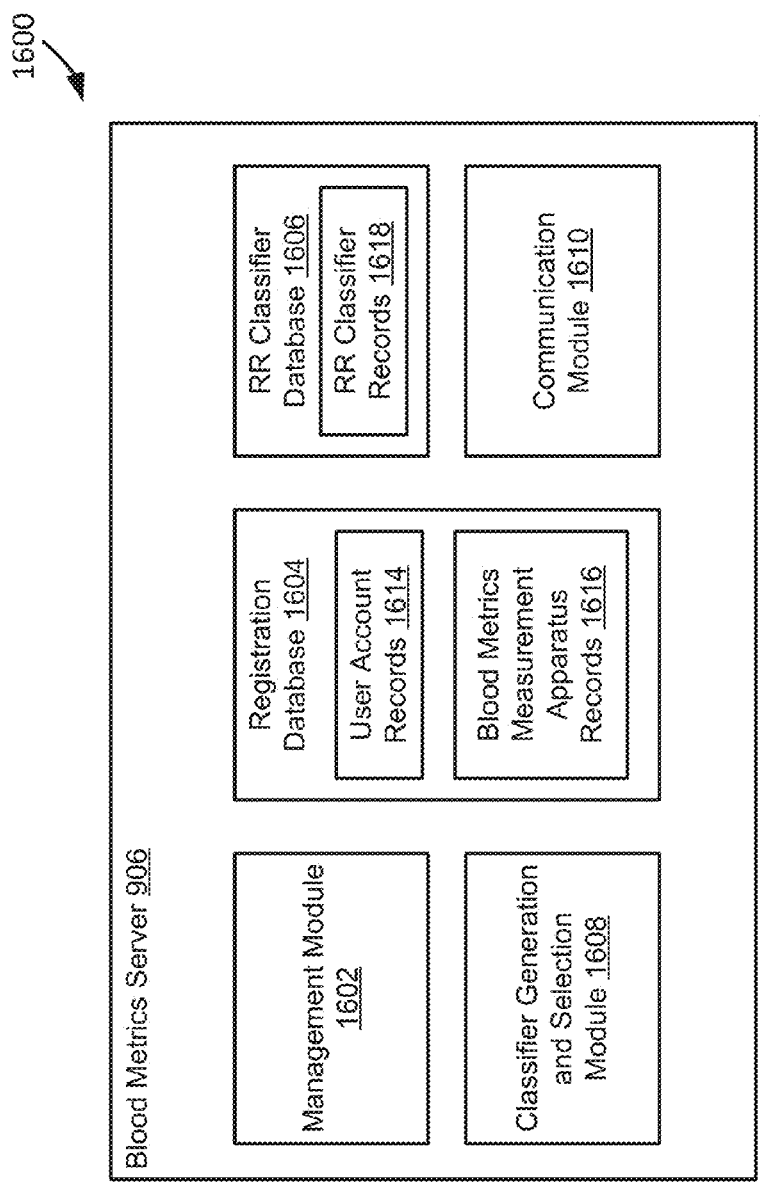
FIG. 16 depicts a block diagram of a blood metrics server according to some embodiments.

FIG. 16 depicts a block diagram 1600 of a blood metrics server 906 according to some embodiments. Generally, the blood metrics server 906 may be configured to generate and/or store respiratory rate classifiers, provide respiratory rate classifiers to a respiratory rate calculation system, register user account and blood metrics measurement apparatus', and communicate with other systems of the system and environment 900. In some embodiments, the blood metrics server 906 includes a management module 1602, a registration database 1604, a respiratory rate database 1606, a classifier generation and selection module 1608, and a communication module 1610.

The management module 1602 may be configured to manage (e.g., create, read, update, delete, or access) user account records 1614 and blood metrics measurement apparatus records 1616 stored in the registration database 1604, and respiratory rate classifier records 1618 stored in the respiratory rate classifier database 1606. The management module 1402 may perform these operations manually (e.g., by an administrator interacting with a GUI) and/or automatically (e.g., by one or more of the modules 1608 or

1610). In some embodiments, the management module 1602 comprises a library of executable instructions which are executable by a processor for performing any of the aforementioned management operations. The databases 1604 and 1606 may be any structure and/or structures suitable for storing the records 1614-1618 (e.g., an active database, a relational database, a table, a matrix, an array, a flat file, and the like).

The user account records 1614 may include a variety of information associated with users, user accounts, associated blood metrics measurement apparatus' and/or associated user devices. For example, the user account records 1614 may store some or all of the following information:

User Account Identifier: Identifier that identifies a user account.

Password: Password, or other personal identifier, used to authenticate the user account. For example, it may an alphanumerical password, biometric data (e.g., fingerprint, etc.). In some embodiments, readings or measurements from the blood metrics measurement apparatus 902 may be used to authenticate the user account.

Device Identifier(s): Identifier(s) that identify one or more blood metrics measurement apparatus' associated with the user account and/or user device.

Name: A name of the user.

DOB: A date of birth of the user.

Age: An age of the user.

Gender: Gender of the user (e.g., female, male, transgender, or the like).

Weight: A weight of the user.

Height: A height of the user.

Skin color: A skin color of the user.

Activity Level: An activity level of the user (e.g., sedentary, lightly active, active, very active, and so forth).

Geographic location: A location of the user (e.g., as determined by a location service and/or specified by the user).

Respiratory Rate Profile

Blood Glucose Profile (e.g., Diabetes information)

Wrist circumference: Circumference of the user's wrist.

The blood metrics measurement apparatus registration records 1616 may include a variety of information associated with users, user accounts, associated blood metrics measurement apparatus' and/or associated user devices. For example, the blood metrics measurement apparatus registration records 1616 may store some or all of the following information:

Apparatus Identifier: Identifier that identifies a blood metrics measurement apparatus.

User Account Identifier: Identifier that identifies a user account and/or user device associated with the blood metrics measurement apparatus.

Geographic location: A current location of the blood metrics measurement apparatus (e.g., as determined by a location service and/or specified by the user).

Settings: One or more settings of the blood measurement metrics apparatus.

For example, some or all of the settings may be automatically determined based on one or more user account attributes (e.g., height, weight, etc.) and/or by the user.

The respiratory rate classifier database 1606 may include one or more respiratory rate classifier records 1618. The classifiers may include various types of respiratory rate classifiers. For example, a first type may be a non-specific classifier which does not require calibration in order to be used to calculate respiratory rate values. A second type may be a specific classifier which requires calibration in order to be used to calculate respiratory rate values. For example, classifiers of the second type may require information about the user, such age, weight, height, gender, skin color, and/or the like. In some embodiments, the respiratory rate records 1618 may store some or all of the following information:

Classifier Identifier: Identifies an respiratory rate classifier.

Classifier Type: Identifies a type of classifier (e.g., non-specific or specific).

Classifier Parameters: Various classifier parameters (e.g., decision node parameters) and tree structures used to calculate the respiratory rate values based on the sets of feature vectors and/or other related information (e.g., gender, age, weight, height, skin color, etc.). Example tree structures are shown in FIG. 26.

Apparatus Identifier(s): Identifier(s) that identify one or more blood metrics measurement apparatus' using the respiratory rate classifier.

User Account Identifier(s): Identifier(s) that identify one or more user account(s) associated with the blood metrics measurement apparatus that use the respiratory rate classifier.

The classifier generation and selection module 1608 may be configured to generate respiratory rate classifiers and/or identify an respiratory rate classifiers stored in the records 1618 to provide to a respiratory rate calculation system. For example, an respiratory rate classifier may be identified in response to a request from a user device or a respiratory rate calculation system. In various embodiments, the classifier generation and selection module 1608 identifies a non-specific respiratory rate classifier which does not require further calibration prior to being used by a respiratory rate calculation system to calculate respiratory rate values. In some embodiments, the classifier generation and selection module 1608 includes some or all of the functionality of a wave selection module, feature extraction module, respiratory rate processing module, along with associated features and/or functionality (e.g., a signal database, wave database, and so forth).

In some embodiments, the communication module 1610 may be configured to send requests to and receive data from one or a plurality of systems. The communication module 1610 may send requests to and receive data from a systems through a network or a portion of a network. Depending upon implementation-specific or other considerations, the communication module 1610 may send requests and receive data through a connection (e.g., the communication network 908, and/or the communication link 910), all or a portion of which may be a wireless connection. The communication module 1610 may request and receive messages, and/or other communications from associated systems.

Figure 17:
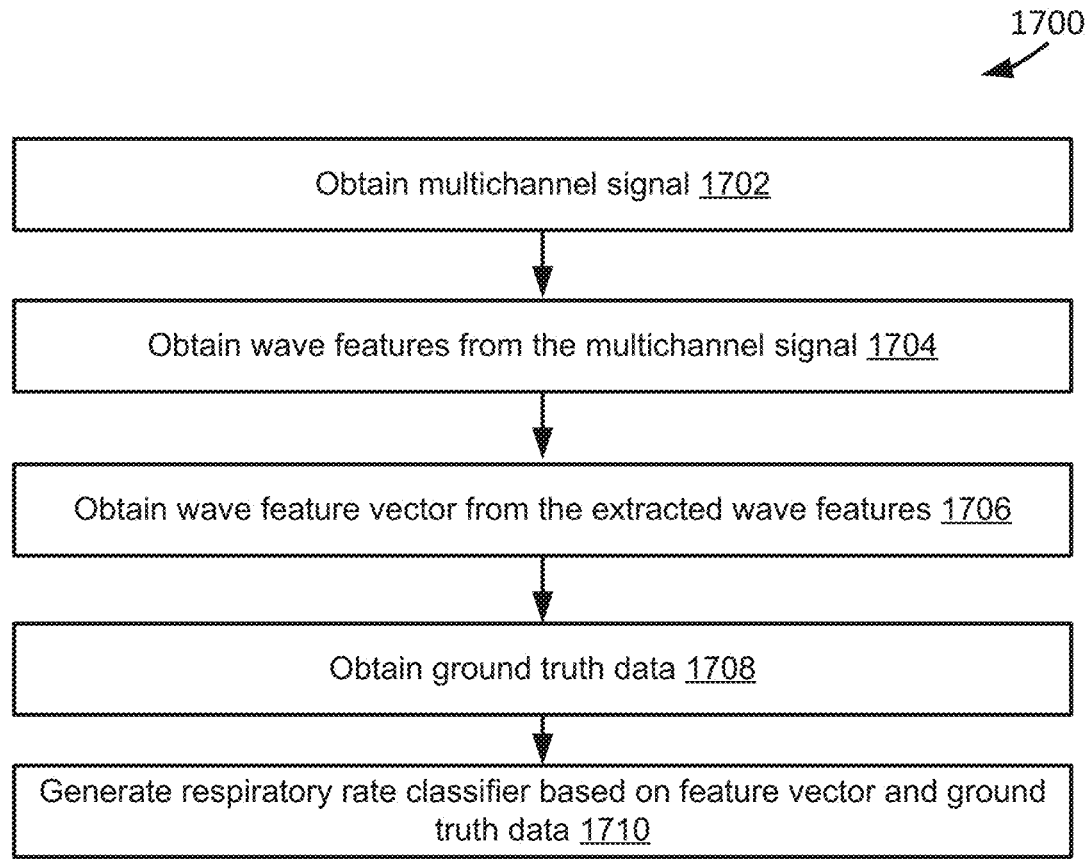
FIG. 17 depicts a flowchart of an example method of training a respiratory rate classifier according to some embodiments.

FIG. 17 depicts a flowchart 1700 of an example method of training a respiratory rate classifier according to some embodiments.

In step 1702, a blood metrics server (e.g., blood metrics server 906) obtain a multichannel signal. For example, the signal may comprise a multichannel PPG signal generated from light energy emitted at the same or different wavelengths (e.g., 523 nm, 590 nm, 623 nm, 660 nm, 740 nm, 850 nm, or 940 nm) from one or more light sources (e.g., multiple LEDs) in the tissue of a user. Multichannel signals and/or different light sources may help ensure, for example, that good quality signals may be obtained in a variety of circumstances (e.g., a user moving, walking, running, sleeping, and so forth). In some embodiments, a classifier generation and selection module (e.g. module 1608) obtains the signal from a blood metrics measurement apparatus (e.g., blood metrics measurement apparatus 906) worn on the wrist of a user.

In step 1704, the blood metrics server obtains wave features from the multichannel signal. In some embodiments, the classifier generation and selection module obtains the waves features from the blood metrics measurement apparatus.

In step 1706, the blood metrics server obtains wave feature vectors from the wave features. In some embodiments, the classifier generation and selection module obtains the wave feature vectors from the blood metrics measurement apparatus.

In step 1708, the blood metrics server obtains ground truth data. In some embodiments, the classifier generation and selection module obtains ground truth data. In some embodiments, the blood metrics server obtains the ground truth data from a database of the blood metrics server and/or a remote server.

In step 1710, the blood metrics server generates and/or trains a respiratory rate classifier based on the feature vector and the ground truth data. In some embodiments, the classifier generation and selection module generates and/or trains the respirator rate classifier.

Figure 18:
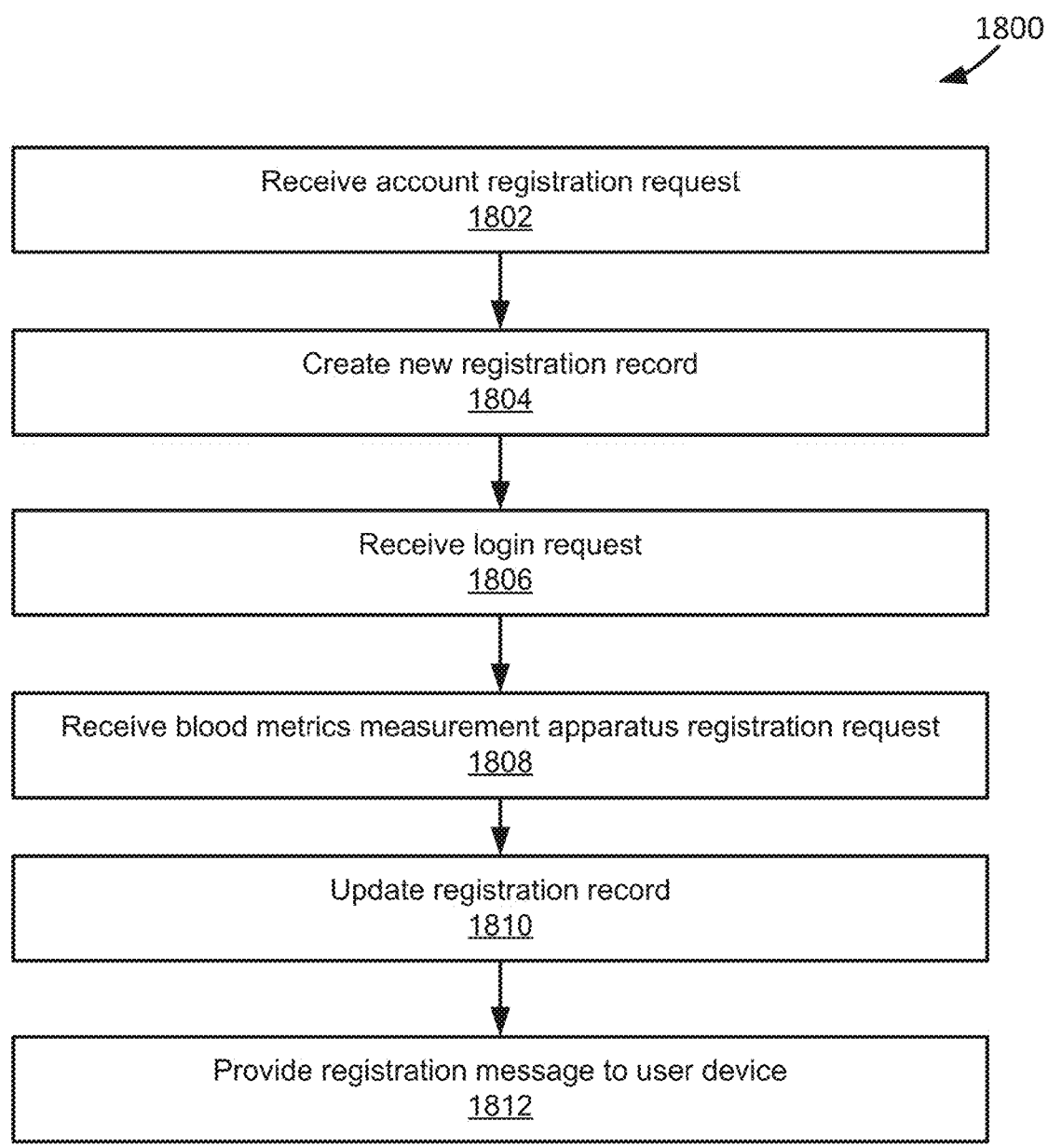
FIG. 18 depicts a flowchart of an example method of operation of a blood metrics server according to some embodiments.

FIG. 18 depicts a flowchart 1800 of an example method of operation of a blood metrics server (e.g., blood metrics server 906) according to some embodiments.

In step 1802, the blood metrics server receives a user account registration request from a user device (e.g., user device 904) via a communication network (e.g., communication network 908). The user account registration request may include, for example, a username (e.g., "jsmith2015), password, full name (e.g., "John Smith"), birthdate, gender, physical characteristics (e.g., height, weight, etc.), and so forth. In some embodiments a communication module (e.g., communication module 1610) receives the user account registration request.

In step 1804, if the blood metrics server approves the registration request, the blood metrics server may create a new user account registration record (e.g., user account registration record 1614) in a registration database (e.g., registration database 1604) and/or an account for the user. In some embodiments, a management module (e.g., management module 1602) creates the user account registration record.

In step 1806, the blood metrics server receives a log-in request from the user device. The log-in request may include, for example, the username and password. If the log-in credentials are correct, the blood metrics server logs the user account into the user device. In some embodiments the communication module receives the log-in request.

In step 1808, the blood metrics server receives a blood metrics measurement apparatus registration request from the user device. The blood metrics measurement apparatus registration request may include, for example, an apparatus identifier that identifies the blood metrics measurement apparatus, and a user account identifier associated the user account and/or user device. The apparatus identifier may be obtained by the user device by a variety of methods (e.g., scanning a physical feature such as a tag, code, or the like) of the blood metrics measurement apparatus, entering the identifier manually via the user device, and/or the like. In some embodiments the communication module receives the blood metrics measurement apparatus registration request.

In step 1810, the blood metrics server updates the registration database with the blood metrics measurement apparatus registration request by either creating a new record or, if the apparatus identifier is already stored in one of the records, updating that particular record. In some embodiments, the management module updates the registration database.

In step 1812, the blood metrics server provides a registration success message to the user device when the registration database has been updated. In some embodiments the communication module provides the message.

FIG. 19 depicts an example noisy PPG signal 1900 and an example filtered PPG signal 1950 according to some embodiments.

Figure 20:
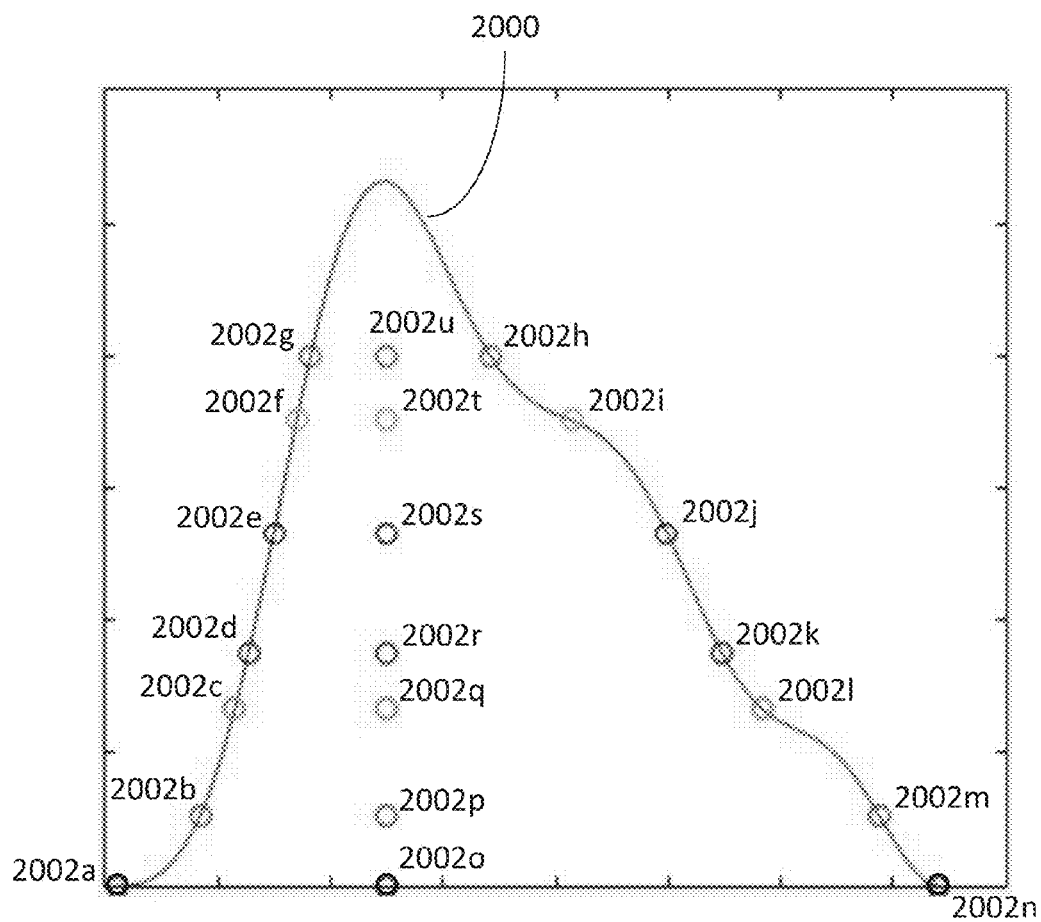
FIG. 20 depicts example feature points of a wave according to some embodiments.

FIG. 20 depicts example feature points 2002a-u of a wave 2000 according to some embodiments. For example, the feature points 2002a-u may comprise location points and/or amplitudes. In some embodiments, some or all of the features points 2002a-u may correspond to measurement values which may be used by one or more metric functions.

FIG. 22 depicts example error distribution plots 2202 and 2204 of respiration rate estimation for two different set of filter parameters according to some embodiments. More specifically a respiratory rate root-mean-square error (RRRMSE) calculates the square root of mean-squared difference between the ground truth data. A classifier may be used to distinguish signal data into two categories (e.g., low and high respiration rate), and the classifier can apply different filter parameters based on the category associated with signal data.

It will be appreciated that a "user device," "apparatus," "server," "module," "system," and/or "database" may comprise software, hardware, firmware, and/or circuitry. In one example, one or more software programs comprising instructions capable of being executable by a processor may perform one or more of the functions of the user devices, servers, modules, systems, and/or databases described herein. In another example, circuitry may perform the same or similar functions. Alternative embodiments may comprise more, less, or functionally equivalent user devices, apparatus, servers, modules, systems, and/or databases, and still be within the scope of present embodiments. In some embodiments, functionality of the devices, apparatus, servers, modules, systems, and/or databases may be performed by one or of the other devices, apparatus, servers, modules, systems, and/or databases. For example, the blood metrics measurement apparatus 902 may include some or all of the functionality of the user device 904 and the blood metrics server 906.

The present invention(s) are described above with reference to example embodiments. It will be appreciated that various modifications may be made and other embodiments may be used without departing from the broader scope of the present invention(s). Therefore, these and other variations upon the example embodiments are intended to be covered by the present invention(s).

The invention claimed is:

1. A system comprising:
   a wearable member including:
      an energy transmitter configured to project energy into tissue of a user; and
      an energy receiver configured to generate a multichannel signal based on a first received portion of the energy, the first received portion of the energy being received through the tissue of the user; and
   a respiratory rate calculation system including:
      a pre-processing module configured to filter noise from the multichannel signal;
      a spectrum module configured to determine a spectrum of the multichannel signal;

a respiratory rate processing module configured to:
   determine a first respiratory rate from the spectrum of the multichannel signal;
   obtain a noise reference;
   obtain one or more second respiratory rates; and
   determine a third respiratory rate based on the first respiratory rate, the noise reference, and the one or more second respiratory rates; and
a communication module configured to provide a message including or being based on the third respiratory rate.

2. The system of claim 1, wherein the energy transmitter includes a first light source and a second light source, the first light source configured to project the energy at a first wavelength, and the second light source configured to project the energy at a second wavelength.

3. The system of claim 2, wherein the energy projected by the first light source and the energy projected by the second light source each have the same wavelength.

4. The system of claim 1, wherein the pre-processing module is configured to filter the noise from the multichannel signal using a trained respiratory rate classifier configured to determine filter parameters for the pre-processing module.

5. The system of claim 4, wherein the trained respiratory rate classifier comprises a respiratory rate classifier trained using ground truth data and one or more feature vectors generated from the multichannel signal.

6. The system of claim 5, wherein the one or more feature vectors include a set of features extracted from the multichannel signal, the set of features including any of optical ratio features, heart rate, signal level and range features, and signal metric features.

7. The system of claim 1, wherein the spectrum module determines the spectrum of the multichannel signal based on a spectral density of the multichannel signal.

8. The system of claim 1, wherein the one or more second respiratory rates comprise one or more previously obtained respiratory rates associated with the user.

9. The system of claim 1, wherein the multichannel signal comprises a multichannel photoplethysmogram (PPG) signal.

10. A method comprising:
   projecting, by a wearable member, energy into tissue of a user;
   generating, by the wearable member, a multichannel signal based on a first received portion of the energy, the first received portion of the energy being received through the tissue of the user;
   filtering, by a respiratory calculation system, noise from the multichannel signal;
   determining, by the respiratory calculation system, a spectrum of the multichannel signal;
   determining, by the respiratory calculation system, a first respiratory rate from the spectrum of the multichannel signal;
   obtaining, by the respiratory calculation system, a noise reference;
   obtaining, by the respiratory calculation system, one or more second respiratory rates;
   determining, by the respiratory calculation system, a third respiratory rate based on the first respiratory rate, the noise reference, and the one or more second respiratory rates; and
   providing, by the respiratory calculation system, a message including or being based on the third respiratory rate.

11. The method of claim 10, wherein the energy is projected using a first light source and a second light source, the first light source configured to project the energy at a first wavelength, and the second light source configured to project the energy at a second wavelength.

12. The method of claim 11, wherein the energy projected by the first light source and the energy projected by the second light source each have the same wavelength.

13. The method of claim 10, wherein the noise is filtered from the multichannel signal using a trained respiratory rate classifier configured to determine filter parameters for the respiratory calculation system.

14. The method of claim 13, wherein the trained respiratory rate classifier comprises a respiratory rate classifier trained using ground truth data and one or more feature vectors generated from the multichannel signal.

15. The method of claim 14, wherein the one or more feature vectors include a set of features extracted from the multichannel signal, the set of features including any of optical ratio features, heart rate, signal level and range features, and signal metric features.

16. The method of claim 10, wherein the spectrum is determined based on a spectral density of the multichannel signal.

17. The method of claim 10, wherein the one or more second respiratory rates comprise one or more previously obtained respiratory rates associated with the user.

18. The method of claim 10, wherein the multichannel signal comprises a multichannel photoplethysmogram (PPG) signal.

19. A system comprising:
   a processor; and
   memory storing instructions that, when executed by the processor, cause the processor to:
      control an energy transmitter to project energy into tissue of a user;
      generate a multichannel signal based on a first received portion of the energy, the first received portion of the energy being received through the tissue of the user;
      filter noise from the multichannel signal;
      determine a spectrum of the multichannel signal;
      determine a first respiratory rate from the spectrum of the multichannel signal;
      obtain a noise reference;
      obtain one or more second respiratory rates;
      determine a third respiratory rate based on the first respiratory rate, the noise reference, and the one or more second respiratory rates; and
      provide a message including or being based on the third respiratory rate.

* * * * *